United States Patent
Raedt et al.

(10) Patent No.: US 12,293,295 B2
(45) Date of Patent: May 6, 2025

(54) HISTOLOGICAL IMAGE ANALYSIS

(71) Applicant: OSLO UNIVERSITETSSYKEHUS, Oslo (NO)

(72) Inventors: Sepp De Raedt, Oslo (NO); Ole-Johan Skrede, Oslo (NO); Håvard Emil Greger Danielsen, Oslo (NO); Tarjei Sveinsgjerd Hveem, Oslo (NO); Andreas Kleppe, Oslo (NO); Knut Liestøl, Oslo (NO)

(73) Assignee: OSLO UNIVERSITETSSYKEHUS (NO)

( * ) Notice: Subject to any disclaimer, the term of this patent is extended or adjusted under 35 U.S.C. 154(b) by 70 days.

(21) Appl. No.: 17/753,931

(22) PCT Filed: Sep. 18, 2020

(86) PCT No.: PCT/EP2020/076090
§ 371 (c)(1),
(2) Date: Mar. 18, 2022

(87) PCT Pub. No.: WO2021/053135
PCT Pub. Date: Mar. 25, 2021

(65) Prior Publication Data
US 2024/0037747 A1    Feb. 1, 2024

(30) Foreign Application Priority Data
Sep. 20, 2019   (GB) ...................................... 1913616

(51) Int. Cl.
*G06N 3/084*      (2023.01)
*A61B 5/00*       (2006.01)
(Continued)

(52) U.S. Cl.
CPC ............ *G06N 3/084* (2013.01); *A61B 5/4848* (2013.01); *A61B 34/10* (2016.02); *G06T 7/0016* (2013.01);
(Continued)

(58) Field of Classification Search
None
See application file for complete search history.

(56) References Cited

U.S. PATENT DOCUMENTS

| | | | |
|---|---|---|---|
| 2017/0161891 A1 | 6/2017 | Madabhushi et al. | |
| 2019/0156159 A1 | 5/2019 | Kopparapu | |
| 2021/0271847 A1* | 9/2021 | Courtiol | ............... G06V 20/698 |

FOREIGN PATENT DOCUMENTS

| | | |
|---|---|---|
| CN | 107886127 A | 4/2018 |
| CN | 110023994 A | 7/2019 |

(Continued)

OTHER PUBLICATIONS

Campanella, et al., Campanella, G., Hanna, M.G., Geneslaw, L. et al. Clinical-grade computational pathology using weakly supervised deep learning on whole slide images. Nat Med 25, 1301-1309 (2019). https://doi.org/10.1038/s41591-019-0508-1.

(Continued)

*Primary Examiner* — Leon Flores
(74) *Attorney, Agent, or Firm* — Billion & Armitage

(57) ABSTRACT

A computer implemented system for determining an overall-classifier for one or more source-histological-images. The system comprising: a first tile generator (204) configured to generate a plurality of first-tiles (206; 306) from the one or more source-histological-image (202; 302); and a second tile generator (205) configured to generate a plurality of second-tiles (207; 307) from the one or more source-histological-images (202; 302). The first-area of the first-tiles (206; 306) is larger than the second-area of the second-tiles (207; 307);

(Continued)

and the second-resolution of the second-tiles (207; 307) is higher than the first-resolution of the first-tiles (206; 306). The system also includes a machine-learning network (211; 311) configured to process the plurality of first-tiles (206; 306) in order to determine a first-classifier (218; 318); a machine-learning network (215; 311) configured to process the plurality of second-tiles (207; 307) in order to determine a second-classifier (219; 319); and a classifier combiner configured to combine the first-classifier (218; 318) and the second-classifier (219; 319) to determine the overall-classifier (232; 332).

23 Claims, 31 Drawing Sheets

(51) Int. Cl.

| | | |
|---|---|---|
| *A61B 34/10* | (2016.01) | |
| *G06T 7/00* | (2017.01) | |
| *G06V 10/26* | (2022.01) | |
| *G06V 10/44* | (2022.01) | |
| *G06V 10/70* | (2022.01) | |
| *G06V 10/774* | (2022.01) | |
| *G06V 10/776* | (2022.01) | |
| *G06V 10/80* | (2022.01) | |
| *G06V 10/82* | (2022.01) | |
| *G06V 20/69* | (2022.01) | |
| *G06V 20/70* | (2022.01) | |
| *G06V 30/24* | (2022.01) | |
| *G16H 50/20* | (2018.01) | |

(52) U.S. Cl.
CPC ............ *G06V 10/26* (2022.01); *G06V 10/454* (2022.01); *G06V 10/774* (2022.01); *G06V 10/776* (2022.01); *G06V 10/80* (2022.01); *G06V 10/82* (2022.01); *G06V 10/87* (2022.01); *G06V 20/695* (2022.01); *G06V 20/698* (2022.01); *G06V 20/70* (2022.01); *G06V 30/2504* (2022.01); *G16H 50/20* (2018.01); *G06T 2207/20021* (2013.01); *G06T 2207/20081* (2013.01); *G06T 2207/20084* (2013.01); *G06T 2207/30024* (2013.01); *G06V 2201/03* (2022.01)

(56) References Cited

FOREIGN PATENT DOCUMENTS

| | | |
|---|---|---|
| CN | 105027165 | 2/2021 |
| JP | 2019148473 A | 9/2019 |

OTHER PUBLICATIONS

Das, et al., "Classifying histopathology whole-slides using fusion of decisions from deep convolutional network on a collection of random multi-views at multi-magnification," 2017 IEEE 14th (ISBI 2017), 2017, pp. 1024-1027, doi: 10.1109/ISBI.2017.7950690.
Das, et al., K. Das et al., "Multiple instance learning of deep convolutional neural networks for breast histopathology whole slide classification," 2018 IEEE 15th (ISBI 2018), 2018, pp. 578-581, doi: 10.1109/ISBI.2018.8363642.
Hou, et al., L. Hou et al. "Patch-Based Convolutional Neural Network for Whole Slide Tissue Image Classification," 2016 IEEE Conference on CVPR, 2016, pp. 2424-2433 doi: 10.1109/CVPR. 2016.266.
Kraus, et al., Oren Z. Kraus, Jimmy Lei Ba, Brendan J. Frey, Classifying and segmenting microscopy images with deep multiple instance learning, Bioinformatics, vol. 32, Issue 12, Jun. 15, 2016, pp. i52-i59, https://doi.org/10.1093/bioinformatics/btw252.
Mobadersany, et al., Mobadersany et al., "Predicting cancer outcomes from histology and genomics using convolutional networks", Proceedings of the National Academy of Sciences, Mar. 27, 2018 National Academy of Sciences—ISSN 0027-8424, http://dx.doi.org/10.1073/pnas.1717139115.
Skrede, et al., "Deep learning for prediction of colorectal cancer outcome: a discovery and validation study" The Lancet, vol. 395, No. 10221, Jan. 30, 2020 (Jan. 30, 2020), pp. 350-360, XP086024041, https://doi.org/10.1016/S0140-6736(19)32998-8.
International Search Report and Written Opinion for PCT/EP2020/076090, mailed Dec. 11, 2020.
"Comparison of fluorouracil with additional levamisole, higher-dose folinic acid, or both, as adjuvant chemotherapy for colorectal cancer: a randomised trial", QUASAR Collaborative Group, The Lancet, vol. 355., May 6, 2000, 1588-1596.
Bejnordi, et al., "Diagnostic Assessment of Deep Learning Algorithms for Detection of Lymph Node Metastases in Women With Breast Cancer", 2017 American Medical Association, JAMA. 2017;318(22):2199-2210. doi:10.1001/jama.2017.14585.
Bychkov, et al., "Deep learning based tissue analysis predicts outcome in colorectal cancer", Scientific Reports, 2018, DOI:10. 1038/s41598-018-21758-3, www.nature.com/scientificreports/.
Coudray, et al., "Classification and mutation prediction from non-small cell lung cancer histopathology images using deep learning", Nature Medicine, https://doi.org/10.1038/s41591-018-0177-5, www.nature.com/naturemedicine.
Couture, et al., "Multiple Instance Learning for Heterogeneous Images: Training a CNN for Histopathology", Springer Nature Switzerland AG 2018, A. F. Frangi et al. (Eds.): MICCAI 2018, LNCS 11071, pp. 254-262, 2018. https://doi.org/10.1007/978-3-030-00934-2_29.
Danielsen, et al., "Prognostic markers for colorectal cancer: estimating ploidy and stroma", Annals of Oncology 29: 616-623, 2018, doi:10.1093/annonc/mdx794, Dec. 27, 2017, 616-623.
Gray, et al., "Validation Study of a Quantitative Multigene Reverse Transcriptase-Polymerase Chain Reaction Assay for Assessment of Recurrence Risk in Patients With Stage II Colon Cancer", American Society of Clinical Oncology, vol. 29, No. 35, Dec. 10, 2011, www.jco.org., 4611-4619.
Karapetis, et al., "K-ras Mutations and Benefit from Cetuximab in Advanced Colorectal Cancer", The New England Journal of Medicine, Massachusetts Medical Society., Oct. 23, 2008, 1757-1765.
Kather, et al., "Predicting survival from colorectal cancer histology slides using deep learning: A retrospective multicenter study", PLoS Med 16(1): e1002730. https://doi.org/10.1371/journal.pmed. 1002730.
Kerr, et al., "Tailoring treatment and trials to prognosis", Nat. Rev. Clin. Oncol. 10, 429-430 (2013); published online Jun. 11, 2013; doi:10.1038/nrclinonc.2013.97, Aug. 2013, 429-430.
La Thangue, et al., "Predictive biomarkers: a paradigm shift towards personalized cancer medicine", Nature Review, Clinical Oncology, vol. 8, Oct. 2011, pp. 589-596.
Liu, et al., "Detecting Cancer Metastases on Gigapixel Pathology Images", arXiv:1703.02442v2 [cs.CV] Mar. 8, 2017.
Sinicrope, "DNA mismatch repair and adjuvant chemotherapy in sporadic colon cancer", Nat. Rev. Clin. Oncol. 7, 174-177 (2010): doi:10.1038/nrclinonc.2009.235, Mar. 2010, 174-177.
Tong, et al., "Improving Classification of Breast Cancer by Utilizing the Image Pyramids of Whole-Slide Imaging and Multi-Scale Convolutional Neural Networks", 2019 IEEE 43rd Annual Computer Software and Applications Conference (COMPSAC), DOI 10.1109/COMPSAC.2019.00105.
Andre et al., "Adjuvant Fluorouracil, Leucovorin, and Oxaliplatin in Stage II to III Colon Cancer: Updated 10-Year Survival and Outcomes According to BRAF Mutation and Mismatch Repair Status of the MOSAIC Study", Journal of Clinical Oncology, vol. 33 No. 34, Dec. 10, 2015.
Andre, et al., "Improved Overall Survival With Oxaliplatin, Fluorouracil, and Leucovorin As Adjuvant Treatment in Stage II or III Colon Cancer in the MOSAIC Trial", Journal of Clinical Oncology, vol. 27 No. 19, Jul. 1, 2009.

(56) References Cited

OTHER PUBLICATIONS

Gray, et al., "Adjuvant chemotherapy versus observation in patients with colorectal cancer: a randomised study", Lancet 2007; 370: 2020-29.

Hutchins, et al., "Value of Mismatch Repair, KRAS, and BRAF Mutations in Predicting Recurrence and Benefits From Chemotherapy in Colorectal Cancer", Journal of Clinical Oncology, vol. 29 No. 10, Apr. 1, 2011.

Moscow, et al., "The evidence framework for precision cancer medicine", Nature Reviews | Clinical Oncology; vol. 15; Mar. 2018.

Mouradov, et al., "Survival in stage II/III colorectal cancer is independently predicted by chromosomal and microsatellite instability, but not by specific driver mutations", The American Journal of Gastroenterology, 2013.

Salazar et al., "Gene Expression Signature to Improve Prognosis Prediction of Stage II and III Colorectal Cancer", Journal of Clinical Psychology; vol. 29, No. 1; Jan. 1, 2011.

Tokunaga, Hiroki, et al., "Adaptively Weighting Multi-scale FCN", IPSJ SIG Technical Report, vol. 2018-CVIM No. 24 May 10, 2018.

Van Allen, et al., "Whole-exome sequencing and clinical interpretation of formalin-fixed, paraffin-embedded tumor samples to guide precision cancer medicine", Nature Medicine; vol. 20, No. 6; Jun. 2014.

\* cited by examiner

A)

B)

C)

D)

E)

F)

A)

B)

A)

B)

HISTOLOGICAL IMAGE ANALYSIS

FIELD OF THE INVENTION

This invention relates to analysis of histological images. It relates in particular to using a machine-learning algorithm to perform such analysis and also to training the machine-learning algorithm to perform the analysis.

BACKGROUND OF THE INVENTION

Biomarkers are being used increasingly to match anticancer therapy to specific tumor genotypes, protein and RNA expression profiles, usually in patients with advanced disease (La Thangue & Kerr, Nat Rev Clin Oncol, 2011; 8: 587-96; Van Allen et al., Nat Med, 2014; 20: 682-8; Moscow et al., Nat Rev Clin Oncol 2018; 15: 183-92).

One example of this is selection of KRAS-wild-type colorectal cancers (CRCs) for treatment with epidermal growth factor receptor inhibitors (Karapetis et al., N Engl J Med, 2008; 359: 1757-65). However, in the adjuvant setting for CRC, the primary question is binary, whether to offer treatment at all, and subsequent selection of drugs, dose and schedule is predominantly driven by stage rather than by the existence of companion diagnostics. If it were possible to further refine prognostic models this would allow a more targeted approach by defining a subgroup in whom the absolute benefits of adjuvant chemotherapy are minimal, relative to surgery alone, and at the other end of the spectrum, patients who might benefit from prolonged combination chemotherapy (Kerr & Shi, Nat Rev Clin Oncol, 2013; 10: 429-30; Hutchins et al., J Clin Oncol, 2011; 29: 1261-70; Salazar et al., J Clin Oncol, 2011; 29: 17-24; Gray et al., J Clin Oncol, 2011; 29: 4611-9).

More than two decades of adjuvant trials in patients with early stage CRC using fluropyrimidines, in combination with cytotoxic agents like oxaliplatin, have yielded an improved overall survival (OS) of around 3-5% for patients with stage II or IIIA CRC, the great majority (about 80%) of whom are cured by surgery alone. Around 20% will recur despite adjuvant chemotherapy, there is likely to be a chemotherapy-associated death rate of 0.5-1%, and 20% of patients will suffer significant side-effects. The risk-benefit ratio is rather marginal, but could potentially be much lower if it were possible to define a subgroup at higher risk of recurrence and cancer-specific death (Group Q C, Lancet, 2000; 355: 1588-96; Quasar Collaborative G, Gray R, Barnwell J, et al., Lancet, 2007; 370: 2020-9; Andre et al., J Clin Oncol, 2009; 27: 3109-16; Andre et al., J Clin Oncol, 2015; 33: 4176-87).

Although clinically validated prognostic biomarkers would facilitate adjuvant therapeutic decisions, very few have been sufficiently robustly validated for routine clinical application. A case can be made for routine assessment of mismatch repair (MMR) status (Sinicrope, Nat Rev Clin Oncol, 2010; 7: 174-7; Mouradov et al., Am J Gastroenterol, 2013; 108: 1785-93), as those patients with MMR-deficient tumors tend to have a good prognosis. We have recently reported that measurement of tumor cellular DNA content (ploidy) in combination with stromal fraction can stratify stage II patients into very good, intermediate and poor prognostic groups (Danielsen et al., Ann Oncol, 2018; 29: 616-23). Interestingly, analysis of driver mutations and RNA signatures has shown them to be individually weak prognostic markers and unable to guide clinical decision making (Grey et al, 2011, supra; Mouradov et al., 2013, supra).

Accordingly, there is a need to provide improved means of assessing biomarkers in biological material, and to further develop the ability to provide useful and efficient means to classify biological material, such as for prognostic and diagnostic approaches.

Deep learning has already been shown to be suitable for detection and delineation of some tumor types (Ehteshami Bejnordi et al., JAMA, 2017; 318: 2199-210), and various cancer classifications have been reported (Coudray et al., Nat Med, 2018; 24: 1559-67). However, we have not yet seen validated systems for directly predicting the outcome of a patient based on histological images.

The aim of the present study is to advance the use of deep learning and digital analysis to develop a fully-automated system for histological image analysis. This has been tested and validated in the prediction of prognosis in primary CRC patients using conventional whole slide images (WSIs).

As used herein, a "histological image" refers to an image showing the microscopic structure of biological material. A "histological feature of interest" means a feature of this microscopic structure. The feature may be of interest for prognostic, diagnostic or therapeutic purposes, or for scientific research, for instance.

Histological specimens are typically used to review the structure to determine the diagnosis or to try determine a prognosis.

In the case where the histological images relate to pathologies, the term "histopathological image" may be used.

At the microscopic scale, many of the interesting features of cells are not naturally visible, because they are transparent and colourless. To reveal these features, specimens are commonly stained with one or more markers before being imaged under a microscope. The marker includes one or more colorants (dyes or pigments) that are designed to bind specifically to particular components of the cell structure, thus revealing the histological feature of interest.

One commonly used staining system is called H&E (Haematoxylin and Eosin). H&E contains the two dyes haematoxylin and eosin. Eosin is an acidic dye—it is negatively charged. It stains basic (or acidophilic) structures red or pink. Haematoxylin can be considered as a basic dye. It is used to stain acidic (or basophilic) structures a purplish blue.

DNA (heterochromatin and the nucleolus) in the nucleus, and RNA in ribosomes and in the rough endoplasmic reticulum are both acidic, and so haematoxylin binds to them and stains them purple. Some extracellular materials (i.e. carbohydrates in cartilage) are also basophilic. Most proteins in the cytoplasm are basic, and so eosin binds to these proteins and stains them pink. This includes cytoplasmic filaments in muscle cells, intracellular membranes, and extracellular fibres.

Those skilled in the art will be aware of a number of alternative stains that may be used, examples of which are further discussed in the present application.

Such histological images may be used in particular for evaluating tissues that may be diseased, for example tissues that may be cancerous. Accordingly, the images may be histopathological images. It is useful to be able to classify a histological (e.g. histopathological) image to determine an expected outcome, for example for the purposes of the diagnosis, prognosis and/or stratification of the subject from which a histological image was obtained, to make treatment decisions for the subject and/or to assess the effect of treatments that are and/or have been received by the subject.

Conventionally, histological features of interest are identified in histological images by histopathologists—specialist medical experts trained in the interpretation of these images.

However, experiments have been carried out and the classification by histopathologists has been shown to be inconsistent and in many cases of limited prognostic value, both when comparing the identifications of different histopathologists and even when presenting the same images to the same histopathologist on different occasions. Such inconsistencies and inter and intra observer variability can have serious implications.

There is accordingly a need for improved automated histopathological image analysis methods and apparatus.

SUMMARY OF THE INVENTION

The invention is defined by the claims.

There is disclosed a computer implemented system for determining an overall-classifier for one or more source-histological-images, the system comprising:
  a first tile generator configured to generate a plurality of first-tiles from the one or more source-histological-image, wherein each of the plurality of first-tiles comprises a plurality of pixels that represents a region of the one or more source-histological-images having a first-area and a first-resolution;
  a second tile generator configured to generate a plurality of second-tiles from the one or more source-histological-images, wherein each of the plurality of second-tiles comprises a plurality of pixels that represents a region of the one or more source-histological-images having a second-area and a second-resolution, wherein:
    the first-area of the first-tiles is larger than the second-area of the second-tiles; and
    the second-resolution of the second-tiles is higher than the first-resolution of the first-tiles;
  a machine-learning network configured to process the plurality of first-tiles in order to determine a first-classifier for the one or more source-histological-images;
  a machine-learning network configured to process the plurality of second-tiles in order to determine a second-classifier for the one or more source-histological-images; and
  a classifier combiner configured to combine the first-classifier and the second-classifier to determine the overall-classifier for the one or more source-histological-images.

The classifier combiner may be configured to:
apply a thresholding function to the first-classifier in order to determine a thresholded-first-classifier;
apply a thresholding function to the second-classifier in order to determine a thresholded-second-classifier; and
combine the thresholded-first-classifier and the thresholded-second-classifier to determine the overall-classifier.

The machine-learning network may be configured to process the plurality of first-tiles in order to determine a plurality of first-classifiers for the one or more source-histological-images. The machine-learning network may be configured to process the plurality of second-tiles in order to determine a plurality of second-classifiers for the one or more source-histological-images.

The classifier combiner may be configured to:
apply a statistical function to the plurality of first-classifiers in order to determine a combined-first-classifier;
apply a statistical function to the plurality of second-classifiers in order to determine a combined-first-classifier;
combine the combined-first-classifier and the combined-second-classifier to determine the overall-classifier.

The classifier combiner may be configured to perform a logical combination of the first-classifier and the second-classifier to determine the overall-classifier for the one or more source-histological-images.

There is also disclosed a computer implemented method of processing histological images, the method comprising:
  receiving one or more source-histological-images;
  generating a plurality of first-tiles from the one or more source-histological-images, wherein each of the plurality of first-tiles comprises a plurality of pixels that represents a region of the one or more source-histological-images having a first-area and a first-resolution;
  generating a plurality of second-tiles from the source-histological-image, wherein each of the plurality of second-tiles comprises a plurality of pixels that represents a region of the one or more source-histological-images having a second-area and a second-resolution, wherein:
    the first-area of the first-tiles is larger than the second-area of the second-tiles; and
    the second-resolution of the second-tiles is higher than the first-resolution of the first-tiles;
  applying a machine-learning network to the plurality of first-tiles in order to determine a first-classifier for the one or more source-histological-images;
  applying a machine-learning network to the plurality of second-tiles in order to determine a second-classifier for the one or more source-histological-images; and
  combining the first-classifier and the second-classifier to determine the overall-classifier for the one or more source-histological-images.

There is also disclosed a computer implemented system for determining a classifier of one or more source-histological-images, the system comprising:
  a tile generator configured to generate a plurality of tiles from the one or more source-histological-images, wherein each of the plurality of tiles comprises a plurality of pixels that represents a region of the one or more source-histological-images;
  a first-neural-network configured to process the plurality of tiles in order to determine a tile-feature for each of the plurality of tiles;
  a pooling-function configured to combine subsets of the tile-features to generate a bag-feature for each of the subsets; and
  a second-neural-network configured to process the bag-features in order to determine a classifier for the one or more source-histological-images. The second-neural-network may be a classification network.

The system may further comprise:
a loss-function configured to:
  compare the classifier that is determined by the second-neural-network with a ground-truth that is represented by truth-data, and
  set trainable parameters for the first-neural-network, the pooling-function, and the second-neural-network based on the result of the comparison.

The system may further comprise:
a segmentation block that is configured to apply an image segmentation method to a whole-slide-image-histological image in order to provide a source-histological-image.

There is also disclosed a computer implemented method of processing histological images, the method comprising:
receiving one or more source-histological-images;
generating a plurality of tiles from the one or more source-histological-images, wherein each of the plurality of tiles comprises a plurality of pixels that represents a region of the source-histological-image;
applying a first-neural-network to the plurality of tiles in order to determine a tile-feature for each of the plurality of tiles;
combining subsets of the tile-features to generate a bag-feature for each of the subsets; and
applying a second-neural-network to the bag-features in order to determine a classifier for the one or more source-histological-images. The second-neural-network may be a classification network.

There is also disclosed a computer implemented system for determining an overall-classifier of one or more source-histological-images, the system comprising:
a first tile generator configured to generate a plurality of first-tiles from the one or more source-histological-images, wherein each of the plurality of first-tiles comprises a plurality of pixels that represents a region of the one or more source-histological-images having a first-area and a first-resolution;
a second tile generator configured to generate a plurality of second-tiles from the one or more source-histological-images, wherein each of the plurality of second-tiles comprises a plurality of pixels that represents a region of the one or more source-histological-images having a second-area and a second-resolution, wherein:
the first-area of the first-tiles is larger than the second-area of the second-tiles; and
the second-resolution of the second-tiles is higher than the first-resolution of the first-tiles;
a machine-learning network configured to process the plurality of first-tiles in order to determine a first-classifier for the one or more source-histological-images, wherein the machine-learning network comprises:
a first-neural-network configured to process the plurality of first-tiles in order to determine a tile-feature for each of the plurality of first-tiles;
a pooling-function configured to combine subsets of the tile-features to generate a bag-feature for each of the subsets; and
a second-neural-network configured to process the bag-features in order to determine a first-classifier for the one or more source-histological-images, wherein the second-neural-network is a classification network;
a machine-learning network configured to process the plurality of second-tiles in order to determine a second-classifier for the one or more source-histological-images, wherein the machine-learning network comprises:
a first-neural-network configured to process the plurality of second-tiles in order to determine a tile-feature for each of the plurality of second-tiles;
a pooling-function configured to combine subsets of the tile-features to generate a bag-feature for each of the subsets; and
a second-neural-network configured to process the bag-features in order to determine a second-classifier for the one or more source-histological-images, wherein the second-neural-network is a classification network; and
a classifier combiner configured to combine the first-classifier and the second-classifier to determine the overall-classifier for the one or more source-histological-images.

There is also disclosed a computer implemented method of determining an overall-classifier for one or more source-histological-images, the method comprising:
generating a plurality of first-tiles from the one or more source-histological-images, wherein each of the plurality of first-tiles comprises a plurality of pixels that represents a region of the one or more source-histological-images having a first-area and a first-resolution;
generating a plurality of second-tiles from the one or more source-histological-images, wherein each of the plurality of second-tiles comprises a plurality of pixels that represents a region of the one or more source-histological-images having a second-area and a second-resolution, wherein:
the first-area of the first-tiles is larger than the second-area of the second-tiles; and
the second-resolution of the second-tiles is higher than the first-resolution of the first-tiles;
applying a machine-learning network to the plurality of first-tiles in order to determine a first-classifier for the one or more source-histological-images, wherein applying the machine-learning network comprises:
applying a first-neural-network to the plurality of first-tiles in order to determine a tile-feature for each of the plurality of first-tiles;
combining subsets of the tile-features to generate a bag-feature for each of the subsets; and
applying a second-neural-network to the bag-features in order to determine a first-classifier for the one or more source-histological-images (the second-neural-network may be a classification network);
applying a machine-learning network to the plurality of second-tiles in order to determine a second-classifier for the one or more source-histological-images, wherein applying the machine-learning network comprises:
applying a first-neural-network to the plurality of second-tiles in order to determine a tile-feature for each of the plurality of second-tiles;
combining subsets of the tile-features to generate a bag-feature for each of the subsets; and
applying a second-neural-network to the bag-features in order to determine a second-classifier for the one or more source-histological-images (the second-neural-network may be a classification network); and
combining the first-classifier and the second-classifier to determine the overall-classifier for the one or more source-histological-images.

Any first tile generator and second tile generator disclosed herein may be configured to generate their respective tiles independently of one another.

Any system disclosed herein may further comprise:
a segmentation block that is configured to apply an image segmentation method to a whole-slide-image-histological image in order to provide a plurality of source-histological-images.

Any first-neural-network disclosed herein may have been trained using training-histological-images and associated ground-truths. Any second-neural-network disclosed herein may have been trained using training-histological-images and associated ground-truths.

Any machine-learning network disclosed herein may have been trained using training-histological-images and associated ground-truths.

Any method disclosed herein may be a method of producing a diagnostic and/or prognostic determination for a subject,
wherein the method comprises receiving one or more source-histological-images obtained from one or more histological samples obtained from the subject, and wherein the method comprises:
determining a classifier for the one or more source-histological-images (102) according to any appropriate method disclosed herein; and/or determining the overall-classifier for the one or more source-histological-images according to any disclosed appropriate method disclosed herein, and
attributing a diagnostic and/or prognostic evaluation to the classifier and/or overall-classifier.

The subject may be a human.

The subject may have, have been diagnosed as having, be suspected of having, be being treated for, have previously been treated for, and/or may have previously had, a pathological condition.

The or each histological sample obtained from the subject may be obtained from the part of the subject's body that has, is suspected of having, is being treated for, has been treated for, and/or has previously had, a pathological condition.

The pathological condition may be cancer, for example a cancer selected from the group consisting of carcinoma, sarcoma, myeloma, leukemia, lymphoma and a mixed type of cancer.

The cancer may be a colorectal cancer.

The method may comprise assessing a plurality of source-histological-images obtained from a plurality of histological samples obtained from the subject in order to determine a plurality of classifiers and/or overall-classifiers, and:
optionally attributing the diagnostic and/or prognostic evaluation to the plurality of classifiers and/or overall-classifiers; and/or
optionally wherein the subject has, has been diagnosed as having, is suspected of having, is being treated for, has previously been treated for, and/or has previously had, a pathological condition, such as cancer, for example a cancer selected from the group consisting of carcinoma, sarcoma, myeloma, leukemia, lymphoma and a mixed type of cancer, and optionally wherein the cancer is a colorectal cancer.

The method may comprise assessing one or more further diagnostic and/or prognostic markers for the pathological condition, and
wherein the step of attributing a diagnostic and/or prognostic evaluation to the classifier and/or overall-classifier may include an assessment of the or each of the results of the assessment of the or each further diagnostic and/or prognostic markers.

The method may further comprise making a treatment decision for the subject on the basis of the diagnostic and/or prognostic evaluation,
optionally wherein the treatment decision is in respect of a diagnosed or prognosed pathological condition, such as cancer, for example a cancer selected from the group consisting of carcinoma, sarcoma, myeloma, leukemia, lymphoma and a mixed type of cancer, and optionally wherein the cancer is a colorectal cancer.

There is also disclosed a method of treating a subject in need thereof, wherein a diagnostic and/or prognostic evaluation has been attributed to the subject by any appropriate method disclosed herein, the method comprising treating the subject by a method of surgery and/or non-surgical therapy;
optionally wherein the treatment for the diagnosed or prognosed pathological condition is for the treatment of cancer, for example a cancer selected from the group consisting of carcinoma, sarcoma, myeloma, leukemia, lymphoma and a mixed type of cancer, and optionally wherein the cancer is a colorectal cancer.

The subject may be a human. In some examples, the subject:
(a) has, has been diagnosed as having, is suspected of having, is being treated for, has previously been treated for, and/or has previously had, a pathological condition; and/or
(b) wherein a diagnostic and/or prognostic evaluation of a pathological condition has been attributed to the subject by any appropriate method disclosed herein.

The pathological condition may be cancer, for example a cancer selected from the group consisting of carcinoma, sarcoma, myeloma, leukemia, lymphoma and a mixed type of cancer, and optionally wherein the cancer is a colorectal cancer.

The method may comprise adapting one or more parameters of the surgery and/or non-surgical therapy in view of the diagnostic and/or prognostic evaluation that has been attributed to the subject by any appropriate method disclosed herein, and optionally
wherein the one or more parameters of the surgery and/or non-surgical therapy are selected from the group consisting of the nature of the surgery and/or non-surgical therapy, the timing of the surgery and/or non-surgical therapy, period of the surgery and/or non-surgical therapy, the dosage of the therapy, the route of administration of the non-surgical therapy, and the site(s) in the body that is targeted by the surgery and/or non-surgical therapy.

The diagnostic and/or prognostic evaluation of the subject may include the assessment of the effect on the subject of an earlier, or ongoing, treatment by surgery and/or non-surgical therapy,
for example, in order to monitor the progress and/or effect of such treatment, and further optionally
wherein the method includes the step of making a further treatment decision, such as the cessation, continuation, repetition or modification an earlier, or ongoing, treatment and/or the implementation of a different treatment modality, and optionally,
implementing that further treatment decision in respect of the subject; optionally wherein:
the diagnostic and/or prognostic evaluation, the treatment and/or the treatment decision is in respect of a pathological condition, such as cancer, for example a cancer selected from the group consisting of carcinoma, sarcoma, myeloma, leukemia, lymphoma and a mixed type of cancer, and optionally wherein the cancer is a colorectal cancer.

There may be provided a computer program, which when run on a computer, causes the computer to configure any apparatus, including a system, block or module disclosed herein or perform any method disclosed herein. The computer program may be a software implementation, and the computer may be considered as any appropriate hardware, including a digital signal processor, a microcontroller, and an implementation in read only memory (ROM), erasable programmable read only memory (EPROM) or electronically erasable programmable read only memory (EEPROM), as non-limiting examples. The software may be an assembly program.

The computer program may be provided on a computer readable medium, which may be a physical computer readable medium such as a disc or a memory device, or may be embodied as a transient signal. Such a transient signal may be a network download, including an internet download.

BRIEF DESCRIPTION OF THE DRAWINGS

The invention will now be described by way of example with reference to the accompanying drawings, in which.

DETAILED DESCRIPTION

Figure 1:
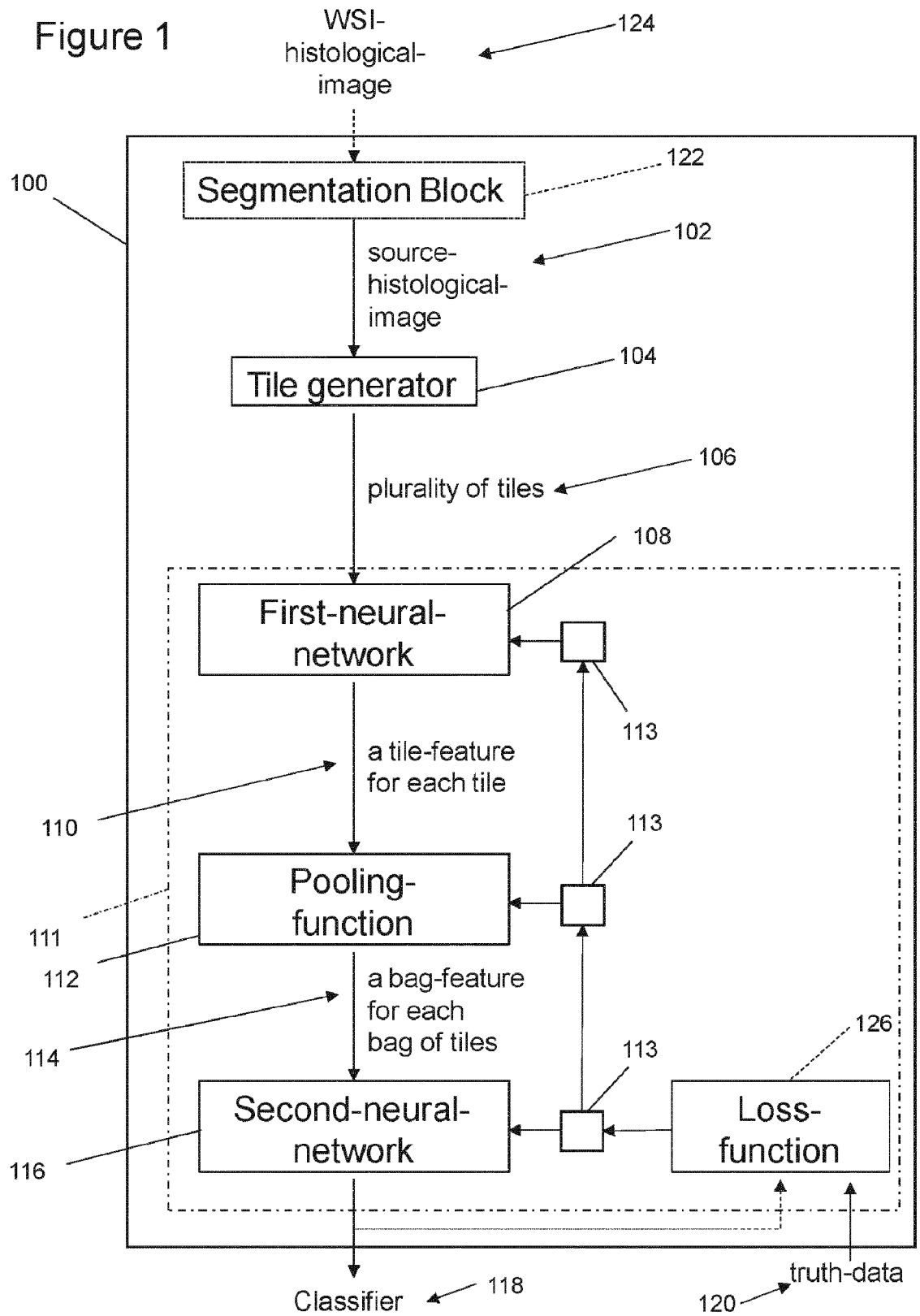
FIG. 1 shows a computer implemented system for determining a classifier of a source-histological-image, such as a source-histopathological-image.

1. Computer Systems of the Present Disclosure 1.1 A First Example Computer System FIG. 1 shows a computer implemented system 100 for determining a classifier 118 of one or more source-histological-images 102, such as a source-histopathological-images.

As will be discussed below, the system 100 includes a network architecture 111 that applies a machine learning algorithm that includes two neural networks 108, 116. When the system 100 is being trained, the received source-histological-images 102 comprise training-histological-images, such as training-histopathological-images, and the system 100 also processes received truth-data 120 that represents a known outcome ("ground-truth") associated with the training-histological-images. For training purposes, the purpose of applying the system 100 is to appropriately configure various trainable parameters (including those associated with the two neural networks 108, 116), which will be used to accurately classify subsequently received source-histological-images 102, such as source-histopathological-images.

As also discussed below, the system 100 can be used to process one or more source-histological-images 102, such as source-histopathological-images, for which the outcome ("ground-truth") is not known. In which case the system can apply the neural networks 108, 116 that were configured using the training-histological-images (such as the training-histopathological-images), such that the output of the system 100 is a classifier 118 for the received source-histological-image 102.

The specific description in sections 1.1 and 1.2 (and other sections) of this document describe an application where a single source-histological-image is divided into a plurality of tiles, such that each tile is a subset of the pixels of the single source-histological-image. In other examples, a plurality of source-histological-images can be processed, such that a tile can be an entire source-histological-image or a subset of the pixels of a source-histological-image. Optionally, a plurality of source-histological-images are processed, such that each source-histological-image is divided into a plurality of tiles, and each tile is a subset of the pixels of each single source-histological-image.

For example, and without limitation, the plurality of source-histological-images may be from the same histological specimen, and/or from different histological specimens obtained from the same biological source. For example, a plurality of source-histological-images may be from different histological specimens obtained from the same organism; in which case, those different histological specimens may, for example, be from the same tissue or from different tissues within the same organism, from the same organ or from different organs within the same organism, or from the same structure or from different structures within the same organism.

By processing a plurality of source-histological-images, the system can take into account features that are present in different locations in a single biological source. Such locations may, optionally, be representative of different planes (for example, parallel or substantially parallel planes, or intersecting planes), present in a single biological source. Such an approach may, therefore, be used to generate information about different locations within a single biological source. One such example is to use images from multiple parallel or substantially parallel planes to generate 3-dimensional information related to that biological source. Such information can be considered as a 'three-dimensional source-histological image', and can also be taken into account in the practice of the present invention as one optional form of source-histological image.

Optionally, a three-dimensional source-histological image can be constructed from multiple physically separate (typically, consecutive parallel or essentially parallel) sections of biological material obtained from a biological source, e.g. as discussed in section 2.4 of this application. Another means of obtaining a three-dimensional source-histological image is to use a selective focussing technique to obtain multiple histological images from a 'thick' histological section, e.g. as discussed further below in section 2.4 of this application.

Another such example is to generate information about multiple discrete locations within a single biological source, for example in order to determine tumour heterogeneity. Further details of such processing are provided below.

1.1.1 Training the Machine Learning Algorithm:

This section relates to training the machine learning algorithm of the system 100 of FIG. 1.

The system 100 includes a tile generator 104, which receives the one or more source-histological-images 102, such as one or more source-histopathological-images. When the system is being trained, a source-histological-image 102 can be referred to as a training-histological-image. When the system is being trained using one or more source-histopathological-images 102, each image can be referred to as a training-histopathological-image. Various examples of source-histological-images are described herein, and it will be appreciated that the system 100 can process any type of histological image including, without limitation, any type of histopathological image. In some examples the, or each, of the one or more source-histological-images 102 may have been segmented before being provided to the tile generator 104. For instance, as will be described in detail below with reference to FIG. 3, an optional segmentation block 122 may process a WSI-histological image 124, such as a WSI-histopathological image, in order to provide the source-histological-image 102. (WSI stands for whole slide image.) The segmentation block 122 may itself be a neural network in some examples.

The tile generator 104 generates a plurality of tiles 106 from the one or more source-histological-images 102, such as one or more source-histopathological-images. Each of the plurality of tiles 106 comprises a plurality of pixels that represents a region of the source-histological-image 102. In some examples, the plurality of tiles may be rectangular and can correspond to adjacent regions of the one or more source-histological-images 102. In some examples, pixels of the, or each, source-histological-image 102 are included in only a single tile. Optionally, the tiles may be spaced apart from each other, contiguous with each other, or may be overlapping with each other. In some applications, some of the pixels from the, or each, source-histological-image 102 may not be included in any tile—for instance if there are insufficient pixels that are positioned to form a complete tile at the periphery of the source-histological-image 102.

The tile generator 104 (or another component of the system 100) then allocates subsets of the plurality of tiles 106 to a 'bag' as is known in multiple instance learning. The tiles may be randomly allocated to a bag. In one example, the tiles can be drawn uniformly at random without replacement. If the bag can fit all tiles in an image, then all tiles would be sampled sequentially. If not, then a sampling scheme could be applied that gives more weight to some tiles than other based on some criteria (which could change during training).

Each bag represents a subset of the plurality of tiles 106. The collection of all tiles in an image is denoted L A collection of tiles from the same image is called a bag, and a collection of bags is called a batch (or mini-batch). None of the individual tiles are assigned a ground-truth (label), instead the bag of tiles inherits the ground-truth of the image from where it originates. We will denote a bag as a collection of tiles, $B \subseteq I$.

The first-neural-network 108, a pooling-function 112 and the second-neural-network 116 can together be considered as a network architecture 111 for applying a machine learning algorithm using multiple instance learning. One update step of the training is summarised below and then discussed in more detail in the subsequent description:

1. A batch of bags are input to the network architecture 111;
2. The first-neural-network (a representation network) maps each tile 106 to a representation of the tile (a tile-feature 110);
3. Tile-features 100 are aggregated by the pooling-function 112;
4. The second neural-network (a classification network) takes pooled tile-features (bag-features 114) as inputs and produces a prediction (classifier 18);
5. This prediction (classifier 118) is compared with a reference classification (truth-data 120) using some loss function;
6. Derivatives of the loss function with respect to the parameters of the network is used to update respective parameters of the network architecture 111. The first-neural-network 108 (the representation network), the pooling function 112, and the second-neural-network 116 (classification network), all can have trainable parameters that are updated based on the derivatives of the loss function. The entire network 111 can be trained end-to-end.

In the rest of the description, we will ignore the batch dimension (and implicitly assume a batch size of one). Extending to a batch size larger than one works like one would expect in a regular deep learning setting with neural networks.

The first-neural-network 108 processes at least some of the plurality of tiles 106 in order to determine a tile-feature 110 for those tiles 106. The tile-features 110 are representations of the associated input tiles 106. The first-neural-network 108 can also be referred to as a representation network, and can include a relatively lightweight neural network that is applied to each of the plurality of tiles 106. In one application, the first-neural-network 108 is implemented using the known MobileNetV2 network, as described further herein (for example, in section 1.3.4 of the present application). It will be appreciated that any neural network that can extract a feature from a tile 106 can be used as the first-neural-network 108. For instance, any convolutional network can be used, albeit the choice of network can contribute to the overall classification performance. Well-known examples of networks that can be used as the first-neural-network 108 include the VGG family, the Inception family, and ResNet.

The mechanism for training the first-neural-network 108, for example by adjusting weighting values (or other trainable parameters) in the first-neural-network 108, will be described below. In this example, the output of the first-neural-network 108 is not directly compared with truth-data 120 that represents the ground-truth (i.e. known true outcome) that is associated with the source-histological-image 102.

The first-neural-network (which may also be referred to as a representation network) is a function $f_r: \mathbb{R}^{m \times n \times c} \to \mathbb{R}^s$ that maps a tile x with shape m×n×c to some feature representation of the tile $f_r(x; \theta_r)$ with size s. This function can for example be a regular convolutional neural network. The trainable parameters associated with the representation network are denoted $\theta_r$.

In this example, the first-neural-network 108 is applied on all tiles in a bag B, producing a bag of representations $R = \{f_r(x, \theta_r): x \in B\}$. Note that within the same update, all tiles in a bag, and all bags in a batch uses the exact same first-neural-network 108 with the same values of $\theta_r$. All representations within a batch can be computed, and stored, before the next step.

The tile-features 110 for each of the plurality of tiles 106, which are output by the first-neural-network 108, are provided to a pooling-function 112. The pooling-function 112 can combine the tile-features 110 that are associated with the tiles of a bag of tiles to provide a bag-feature 114 for each of the bags.

The pooling function 112 can reduce the set of tile-features R 110 to a single representation for one bag B, and is typically a function $f_p: \mathbb{R}^{b \times s} \to \mathbb{R}^t$ where b is the number of tiles in a bag. Since this function potentially is dependent on the final representations of all tiles in a bag, it may not be computed before all those representations are computed. This function can also have trainable parameters, the collection of which is denoted $\theta_p$.

These bag-features 114 are suitable for processing by a downstream multiple-instance learning (MIL) algorithm. In one application, the pooling-function 112 can apply the known noisy-AND pooling function to generate the bag-features 114. In other examples, the pooling-function 112 can apply any reducing function, such as the sum, mean, median, etc., to the tile-features 110 (which can be considered as input tile representations). Other, more sophisticated examples that can be used include Noisy- or, ISR, generalised mean, LSE.

The second-neural-network 116 processes each of the bag-features 114 in order to determine the classifier 118 for the one or more source-histological-images 102, such as one or more source-histopathological-images. The second-neural-network 116 can be referred to as a classification network. In some examples, the second-neural-network 116 can be provided as a fully-connected neural network The function of the second-neural-network 116 (the classification network) can be represented as $f_c: \mathbb{R}^t \to \mathbb{R}^k$, where k is the number of classes. This function can be parameterised with its own set of trainable parameters $\theta_c$, and the output range is typically [0,1] such that the sum over all k classes $\Sigma_{i=1}^{k} f_c(x; \theta_c)_i = 1$ for all fitting inputs $x \in \mathbb{R}^t$. With this, the output of this function can be interpreted as a prediction probability over the possible output classes, conditioned on the input. Note that all tiles in a bag contribute to one single prediction per bag, and therefore the network 111 does not provide a per-tile prediction, but a per-bag prediction as the classifier 118 that is shown in FIG. 1.

During the training phase, the system 100 also receives the truth-data 120. The truth-data 120 represents the ground-truth (i.e. known true outcome) that is associated with the, or each, source-histological-image 102, such as a source-histopathological-image. For example, and without limitation, in the event that the training phase involves the use of a plurality of source-histological-images from the same histological specimen, and/or from different histological specimens obtained from the same biological source, then the truth-data 120 may represent the same ground-truth (i.e. the same known true outcome) associated with the same biological source from which the, or each, histological specimen has been obtained.

The function of the full network 111 can be represented as $f: \mathbb{R}^{b \times m \times n \times c} \to \mathbb{R}^k$, which produces a classifier 118 that represents a prediction $f(B; \theta r, \theta p, \theta c)$ for each bag of tiles B. A loss-function L 126 compares the classifier 118 with the truth-data. In the following description, we assume that the loss function is sufficiently differentiable to be optimized using a gradient-based optimization method. This is represented graphically in FIG. 1 by the processing blocks 113 that process the output of the loss-function 126 and update the trainable parameters $\theta_r, \theta_p, \theta_c$ of each of the first-neural-network 108, the pooling-function 112 and the second-neural-network 116. One or more of the trainable parameters may also be referred to as weighting values.

Ideally, one would like the tiles in a bag to span the entire image, but this can be limited by hardware constraints in some applications, which often necessitates subsampling. In principle, one can sample tiles from an image in many different ways, but assuming no prior knowledge, a uniform random sampling without replacement is sufficient. With a random subsampling of tiles, it is unlikely that an image will be represented by the same configuration of tiles each time. This could have a regularizing effect on the training, and beneficially help generalization.

As indicated above, a bag is given the label of its origin image, and if the tiles in a bag do not span the entire image, this assignment may not be entirely justified. However, it has been found that that the error caused by assigning the image label to a bag of tiles is smaller than assigning the image label to a single tile. Implicit in this assumption is that the approximation error decreases with an increasing area represented by the tiles in a bag, ranging from a bag with one single tile to a bag containing all tiles in an image.

It can be desirable to use as many tiles as possible to represent an image during the training of the network 111, and for large images, the number of tiles per bag can be limited by the memory of the hardware the method runs on. The first-neural-network 108 (representation network) can be the largest consumer of memory in this framework. In the forward propagation, all tiles in a bag can be processed by the first-neural-network, but only representations of the tiles (i.e. the tile-features 110) are used further in the forward propagation. Storing and processing the tile-features 110 can require considerably less memory than storing and processing the associated tile images 106.

A gradient-based optimization method can make use of intermediate representations of each tile "within" the network 111 to update the parameters of the network. This means that these intermediate representations (including the tile-features 110) are stored until the relevant gradients are computed based on the output of the loss-function 126. By reducing the number of tiles used in the backpropagation, the memory footprint can be significantly reduced. Therefore, in one application, the network 111 can use the entire bag B in the forward propagation of the second-neural-network 116, but only a subset G⊆B of the bag in the backward propagation. Note that in such an application, it may be only the second-neural-network that employs this truncation of gradient contributions. All tile-features 110 from a bag can be used by the pooling function 112 and therefore by the second-neural-network 116, and the update of parameters ($\theta_p$, $\theta_c$) associated with the pooling function 112 and the first-neural-network 108 is not affected with the truncation in the first-neural-network.

All trainable parameters in the network 111 can be updated iteratively with this feedback mechanism.

As will be described in detail below, the system can apply a plurality of iterations around the training loop in order to select final weighting values or other trainable parameters that will be used as part of the machine-learning algorithm 108. The purpose of applying the network 111 for training, as described above, is therefore to appropriately configure the network 111 so that it can be used to accurately classify subsequently received source-histological-images 102, such as source-histopathological-images, for which the outcome ("ground-truth") is not known.

In some examples, the training phase may involve processing data from one or more training cohorts. It will be appreciated that using larger training cohorts can result in a better system 100 for subsequently determining a classifier 118 for source-histological-images 102 for which the outcome is not known. For example, a training cohort may comprise one or more source-histological-images from each of a number of different biological sources, which may be selected from at least 100, 200, 300, 400, 500, 600, 700, 800, 900, 1000, 1500, 200, 2500, 3000, 4000, 5000, 6000, 7000, 8000, 9000, 10000 or more different biological sources, wherein a ground-truth is known for each biological source in the training cohort.

Following the processing of the training cohorts, the system can apply a tuning process using data from a training cohort and/or apply a validation process using data from a validation cohort. A tuning cohort and/or a validation cohort may, for example, comprise one or more source-histological-images from each of a number of different biological sources, wherein the number of different biological sources may, for example, be approximately the same (e.g. ±50%, 40%, 30%, 20%, 10%, 5% or less) in number as, at least as great in number as, or greater in number (e.g. at least 50%, 60%, 70%, 80%, 90%, 100% or more greater than), the number of different biological sources in the training cohort. Exemplary details are provided below, although these are not limiting and the skilled person can use their common general knowledge to select suitable training, tuning and/or validation cohorts for use in this process.

1.1.2 Using the Trained Machine Learning Algorithms:

This section relates to applying the network 111 of FIG. 1 to one or more unclassified source-histological-images 102, such as one or more unclassified source-histopathological-images, for which the outcome ("ground-truth") is not known. This is also referred to as inference. For example, the network 111 may be applied to a plurality of source-histological-images present in a three-dimensional source-histological image, as discussed further above.

That is, the system 100 can apply the network 111 that was configured using training-histological-images (such as training-histopathological-images), in order to determine a classifier 118 for the, or each, received source-histological-image 102. The processing blocks that function in the same way as for the training phase will not be described in the same amount of detail here.

In this example, and others described herein, the system 100 that is used to process unclassified images has been trained using training-histological-images and associated ground-truths. More particularly, one or more of a first-neural-network, a pooling-function, and a second-neural-network have been trained using training-histological-images and associated ground-truths. As is known in the art, training can be performed until a maximum number of iterations around a loop has been performed, or until a loss function reaches an acceptably low value, as non-limiting examples. At which point, the training can be considered as complete. (Which is not to say that training cannot be resumed at a later date, if appropriate.) For instance, optimisation can be performed for a fixed set of epochs (a full traversal through the dataset). So, if there are 100 images in the training set, and the algorithm trains for 10 epochs with a batch size of 5, 200 optimisation steps will be performed before termination. More generally in numerical optimisation, the optimisation can be terminated based on the loss function value. Examples can be (1) when the value is below some threshold, (2) when the absolute change in value in the last k steps is below some threshold, and (3) when change in value in the last k steps relative to the current value is below some threshold.

In the same way described above, the tile generator 104 receives the one or more source-histological-images 102 and generates a plurality of tiles 106 from the, or each, source-histological-image 102.

The first-neural-network 108 processes the plurality of tiles 106 in order to determine tile-features 110 for the plurality of tiles 106. The first-neural-network 108 can utilise a neural network that applies weighting values that were determined during the training phase. The first-neural-network 108 can be applied to all tiles in the image. This can be done on one tile at a time, and each tile-feature 110 can be stored until all tiles are processed by the first-neural-network 108. Each tile representation 110 can require only a very small amount of memory, so the number of tiles per image in inference is for all practical purposes almost limitless in terms of memory requirements.

The pooling-function 112 aggregates the tile-features 110 to provide the bag-features 114. Optionally, especially when processing unclassified source-histological-images 102, the pooling-function 112 may generate bags of bag-features 114 that between them include all of the tile-features 110. That is, none of the tile-features 110 may be excluded from the bag-features 114.

The second-neural-network 116 processes the bag-features 114 in order to determine the classifier 118 for the, or each, source-histological-image 102.

Even though the bag size can be different in training and inference (when applied to unclassified image data), a successfully trained network has been found to still produce reasonable results. For applications where the network 111 uses all tiles in an image for inference, an image is usually better represented in inference than in training. It can be advantageous to have a relatively large bag size for training because this can enable the network 111 to learn features that can be generalized over the entire image. In some examples, a bag that includes more than 5%, 8%, 10%, 15% or 20% of the tiles from an entire image can be considered as a large bag. In some applications, relatively large bags of tiles can also be used during inference. For instance, the algorithm may subsample the tiles during inference to generate large bags and therefore speed up the classification.

It will be appreciated that the loss-function 126 is not applied when processing unclassified source-histological-images 102 because there is no associated truth-data 120.

Optionally, as will be described in detail with reference to FIG. 3, one or more parts of the system 100 of FIG. 1 can be applied multiple times to determine a plurality of classifiers 118 for an image, or a collection of images, which can be combined in order to determine an overall-classifier.

Advantageously, the system of FIG. 1 can accurately and efficiently classify histological images, and in particular for classifying prognoses such as for colorectal cancer.

1.2 A Second Example Computer System

Figure 2:
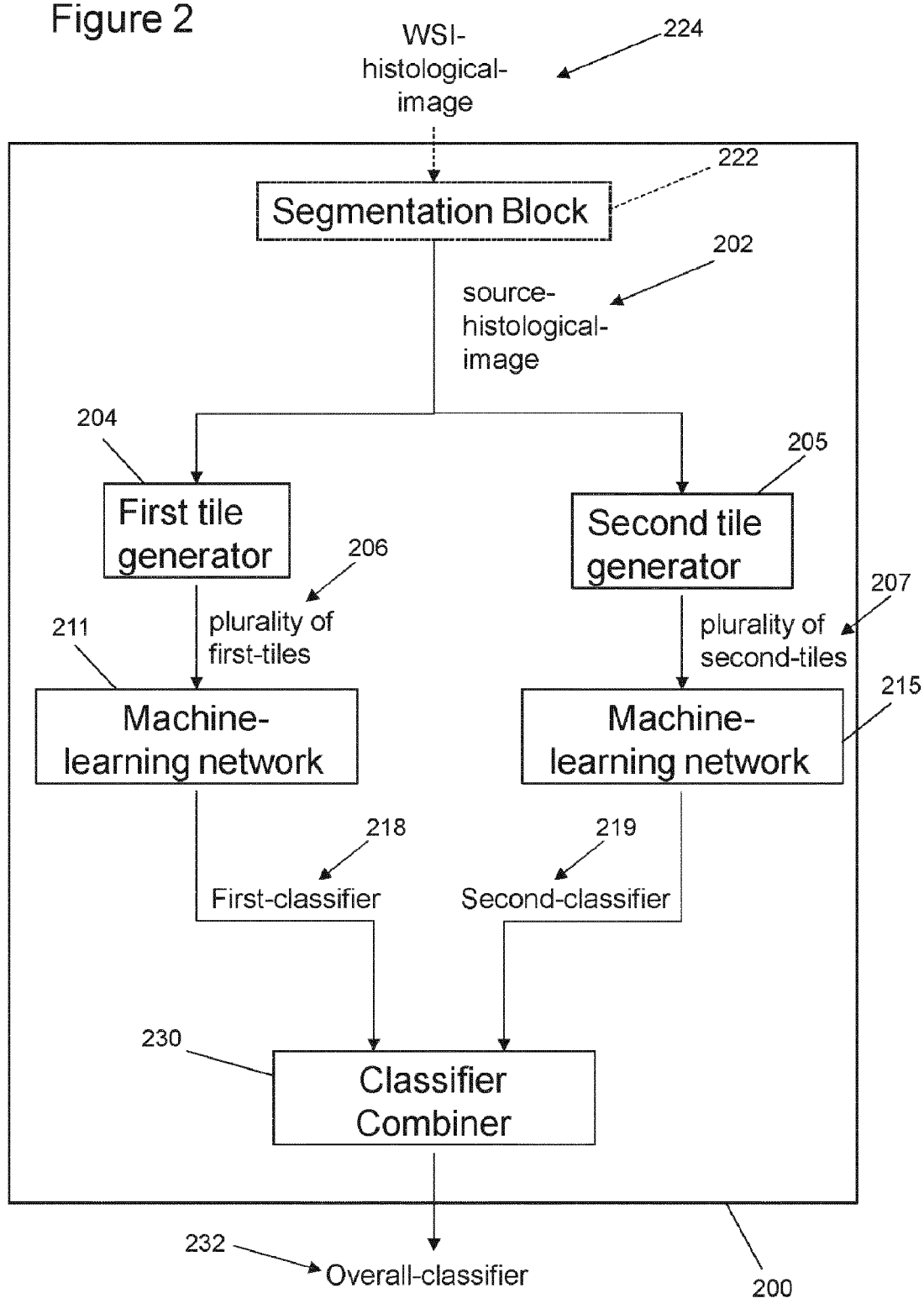
FIG. 2 shows a computer implemented system for determining an overall-classifier for a source-histological-image, such as a source-histopathological-image.

FIG. 2 shows a computer implemented system 200 for determining an overall-classifier 232 for one or more source-histological-images 202, such as one or more source-histopathological-images. This may, optionally, include the determination of an overall-classifier 232 for a collection of source-histological-images 202, such as a plurality of source-histological-images present in a three-dimensional source-histological image, as discussed further above.

As will be discussed below, the system 200 can be used to process one or more source-histological-images 202, such as one or more source-histopathological-images, for which the outcome is not known. The system can apply machine learning networks 211, 215 that have been appropriately configured using training-histological-images (such as training-histopathological-images) in a training phase. The machine learning networks 211, 215 can be trained in any way that is known in the art. In some examples, each of the machine learning networks 211, 215 can include the network 111 that is described with reference to FIG. 1, and can be trained in the same was as described with reference to FIG. 1. That is, each of the machine learning networks 211, 215 may include a first-neural-network, a pooling function and a second-neural-network. FIG. 3 below is an example that combines the systems of FIGS. 1 and 2 in this way.

In one embodiment, the system 200 includes a first tile generator 204 and a second tile generator 205, which both receive the same one or more source-histological-images 202. As with FIG. 1, the system 200 of FIG. 2 can process any type of histological image, such as any type of histopathological-image. Also, the one or more source-histological-images 202 can be provided by an optional segmentation block 222 that processes one or more WSI-histological images 224.

In this embodiment, the first tile generator 204 generates a plurality of first-tiles 206 from the, or each, source-histological-image 202, and the second tile generator 205 generates a plurality of second-tiles 207 from the, or each, source-histological-image 202.

In an alternative embodiment, the system 200 includes a first tile generator 204 and a second tile generator 205, which receive different source-histological-images 202 (first, and second source-histological-images, respectively) that have been generated by obtaining histological images at different magnifications from the same source histological sample. The first source-histological-image 202 and the second source-histological-image 202 may differ at least (typically only) in terms of the degree of magnification that has been applied to the imaging of the same histological sample at the time of image generation.

In this alternative embodiment, the first tile generator 204 generates a plurality of first-tiles 206 from the first source-histological-image 202, and the second tile generator 205 generates a plurality of second-tiles 207 from the second source-histological-image 202.

In either embodiment, each of the plurality of first-tiles 206 comprises a plurality of pixels that represents a region of the source-histological-image 206 having a first-area and a first-resolution; and each of the plurality of second-tiles 207 comprises a plurality of pixels that represents a region of the source-histological-image having a second-area and a second-resolution. The first-area of the first-tiles 206 is larger than the second-area of the second-tiles 207. In this way, the first-tiles 206 represent a larger area of the source-histological-image 202 than the second-tiles 207, and therefore also represent a larger area of the histological specimen that is shown in the source-histological-image 202.

The first-resolution of the first-tiles 206 is lower than the second-resolution of the second-tiles 207. In this way, the second-tiles 207 show more detail, at a greater granularity, of the source-histological-image 202 than the first-tiles 206. Therefore, the second-tiles 207 illustrate more detail of the histological specimen that is shown in the source-histological-image 202.

In this way, the first-tiles 206 can represent a large enough area of the histological specimen such that it includes structural information of the specimen, for example the general structure and/or orientation of tissues within the specimen, the size and/or shape of individual cells within the specimen and/or the locations of individual cells and/or groups of cells, relative other individual cells and/or groups of cells. In more general terms, the first-tiles 206 can be dimensioned to include the architecture of solid multi-cellular structures, such as organs, tissues or other solid structures. Accordingly, this embodiment is particularly suitable for the assessment of solid biological samples (for example, without limitation, solid tumour samples) in which such supra-cellular structure is present. Such information can therefore include information, such as organisational structure and/or differentiation patterns, that are relevant to the classification (such as a diagnosis, or a prognosis) of the specimen.

Some or all of this structural information may not necessarily be visible in the second-tiles 207 because they represent a smaller area than the first-tiles 206. Also, the second-tiles 207 can include sufficient detail of the histological specimen such that it can include information at the individual cellular level, and in particular can show subcellular structures, such as one or more of the presence, size, location, shape, density and/or other characteristics of subcellular structures. Such subcellular structures can include, without limitation, the nuclei in the cells, for example the size and/or density of the nuclei in the cells observable in the second-tiles 207 may be of particular interest, for example, in the diagnosis and/or prognosis of pathologies such as cancers, in particular solid cancers. Additional and/or alternative subcellular structures of interest in the second-tiles 207 can include one or more organelles, and/or one or more other cellular components such as individual proteins, DNA molecules, RNA molecules, lipids and/or membranes.

Exemplary organelles and other macromolecules include, without limitation, the endoplasmic reticulumn (rough and/or smooth), the Golgi apparatus, the mitochondria, the vacuole, the chloroplast, the acrosome, the autophagosome, the centriole, the cilium, the cnidocyst, the eyespot apparatus, the glycosome, the glyoxysome, the hydrogenosome, the lysosome, the melanosome, the mitosome, the myofibril, the nucleolus, the ocelloid, the parenthesome, the peroxisome, the proteasome, the ribosome (80S), the stress granule, the TIGER domain and/or vesicles. Some or all of these sub-cellular structures may not be visible in the first-tiles 206 because they typically do not have the required resolution.

In one embodiment, the first-tiles 206 contain information equivalent to that obtained by a typical low-powered light microscopy analysis of a histological image. In the present examples, the level of magnification used in a low-powered light microscopy analysis is a 10× magnification, although other low-powered levels of magnification can also be used. For example, the level of magnification used in a low-powered light microscopy analysis may be at least 4× and less than 40× magnification, or may be about 4×, 5×, 6×, 7×, 8×, 9×, 10×, 11×, 12×, 13×, 14×, 15×, 16×, 17×, 18×, 19×, 20×, 25×, 30× or 35× magnification. In this context, the term "about" refers to a value that is ±1×, 2×, 3×, 4× or 5× the stated level of magnification, provided that it is a suitable level of magnification to provide some or all of the structural information of the specimen of the type discussed above. In principle, the low-powered magnification need merely be "low-powered" in a relative sense, compared to the power of magnification used for the second-tiles 207.

Additionally, or alternatively, in this embodiment, the second-tiles 207 contain information equivalent to that obtained by a typical high-powered light microscopy analysis of a histological image. In the present examples, the level of magnification used in a high-powered light microscopy analysis is a 40× magnification, although other high-powered levels of magnification can also be used. For example, the level of magnification used in a high-powered light microscopy analysis may be between about 20× and about 100× magnification, such as about 20×, 30×, 40×, 50×, 60×, 70×, 80×, 90 or 100× magnification. In this context, the term "about" refers to a value that is 1×, 2×, 3×, 4× or 5× of the stated level of magnification, provided that it is a sufficient magnification to provide information at the individual cellular level, and in particular can show some or all of the sub-cellular structures of the type discussed above. In principle, the high-powered magnification need merely be "high-powered" in a relative sense, compared to the power of magnification used for the first-tiles 206.

It will be appreciated that the information that is observable in a histological image depends not only on the level of magnification used in the generation of the image and/or resolution of the image as generated, but also on the staining and/or imaging techniques used. For example, the staining technique used will influence the physical structures that are labelled and visible in an image, as discussed further below in section 2.4.1 of the present application.

Importantly, both the first-tiles 206 and the second-tiles 207 can be represented by a sufficiently small amount of computer data such that they can be adequately processed by downstream processing blocks of the system 200, without requiring too much processing power or being too slow. If tiles were generated differently, having both the higher resolution of the second-tiles 207 and the greater area of the first-tiles 206, then the downstream processing blocks may require unacceptably high processing resources to perform adequately.

In some applications, the first tile generator 204 and the second tile generator 205 can generate their respective tiles independently of one another. For instance, the first-tiles 206 do not necessarily need to be centred on the same point of the source histological image 202. Indeed, the first tile generator 204 and the second tile generator 205 do not need to have any information about the other tile generator produces its tiles. In some examples, both the first-tiles 206 and the second-tiles 207 are each randomly directed to different areas of the source-histological-image 202. Therefore, the regions of the source-histological-image 202 on which each of the first-slides 206 is centred can be selected randomly, the regions of the source-histological-image 202 on which each of the second tiles 207 is centred can also be selected randomly, such that the random selection for the first- and second-tiles 206, 207 are independent of each other.

The subsequent application of the two machine learning networks 211, 215, in order to generate accurate classifiers 218, 219, does not require any coordination of how the two sets of tiles are generate or how they relate to each other. Therefore, advantageously, the system 200 of FIG. 2 can avoid the need for any processing that coordinates the two tile generators 204, 205 and the two machine learning networks 211, 215. The system 200 includes a machine-learning network 211 that processes the plurality of first-tiles 206 in order to determine a first-classifier 218 for the, or each, source-histological-image 202. The system 200 also includes a machine-learning network 215 that processes the plurality of second-tiles 207 in order to determine a second-classifier 219 for the, or each, source-histological-image 202. In this way, the second-classifier 219 can be based on information that is illustrated in the second-tiles 207, and the first-classifier 218 can be based on information that is illustrated in the first-tiles 206. These machine-learning networks 211, 215 can each include a single neural network, or a plurality of neural networks such as is illustrated in FIG. 1.

The system also includes a classifier combiner 230 that combines the first-classifier 218 and the second-classifier 219 to determine the overall-classifier 232 for the, or each, source-histological-image 202. This may, optionally, include the determination of an overall-classifier 232 for a collection of source-histological-images 202, such as a plurality of source-histological-images present in a three-dimensional source-histological image, as discussed further above.

The combination can be performed in a number of ways, including a mathematical combination, a logical combination, or a combination of a mathematical and logical combination. For instance, the first- and second-classifiers 218, 219 can have numerical values and the overall-classifier 232 can be the mean of the first- and second-classifiers 218, 219. Alternatively, the first- and second-classifiers 218, 219 can a logical value, and the overall-classifier 232 can be a logical combination of the first- and second-classifiers 218, 219. Such a logical function may be an AND function that sets the overall-classifier 232 as the same logical value as the first- and second-classifiers 218, 219 only if they have the same logical value. Further details of a specific implementation of the classifier combiner 230 is described with reference to FIG. 3.

Advantageously, the system 200 of FIG. 2 can classify one or more source-histological-images 202 in an improved way because it can be based on different characteristics that are only sufficiently represented in one of the sets of tiles (either the large area of the first-tiles 206 or the high definition of the second-tiles 207). Also, the classification can be considered as efficient in terms of the amount of processing resources that are required because the associated information and features can be extracted from the, or each, source-histological-image 202 without requiring a tile that has both a large area and a high definition.

1.3 A Third Example Computer System

Figure 3:
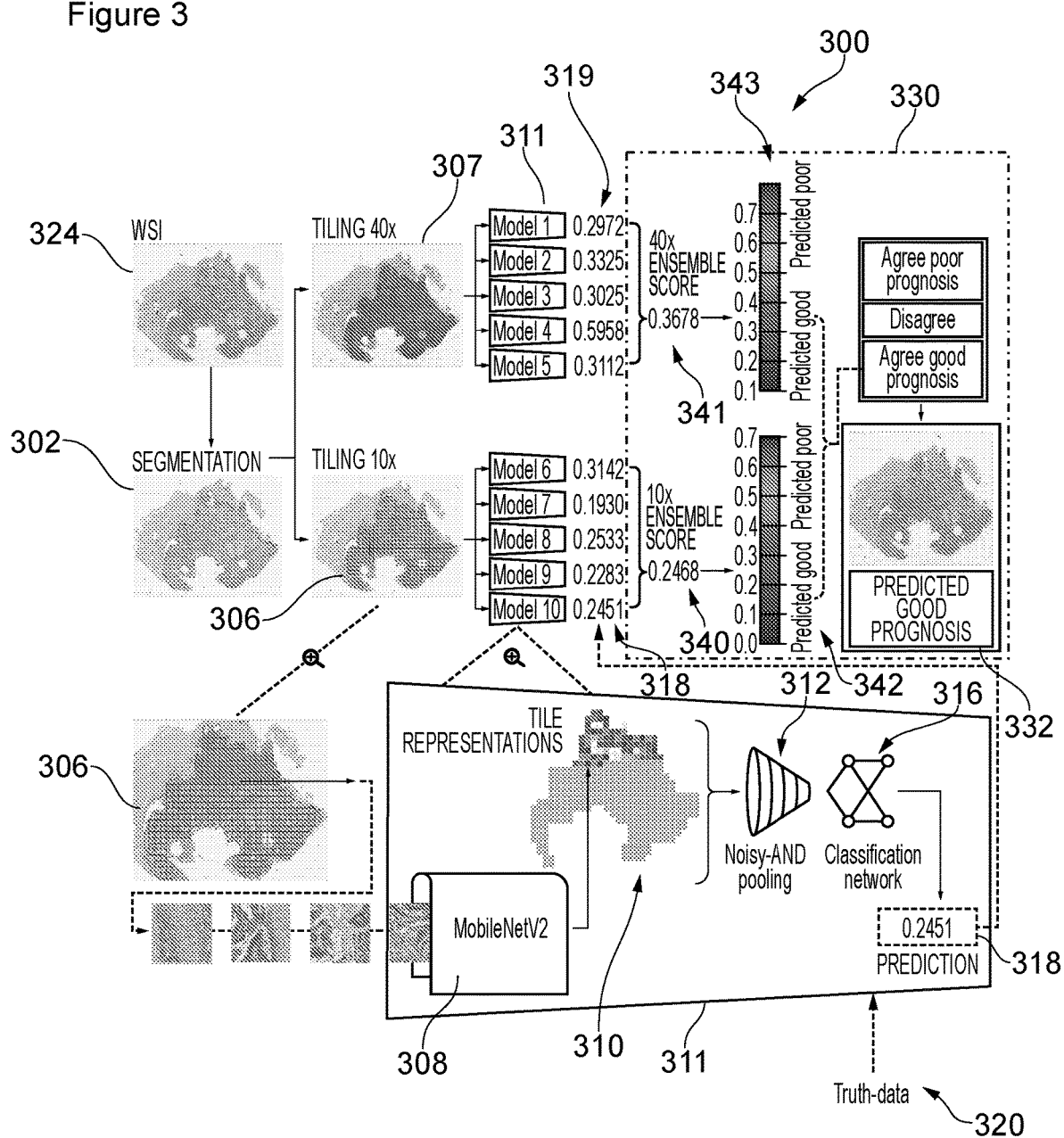
FIG. 3 shows a specific implementation of a system for determining an overall-classifier for a source-histological-image, such as a source-histopathological-image.

FIG. 3 shows a specific implementation of a system 300 for determining an overall-classifier 332 for one or more source-histological-images 302, such as one or more source-histopathological-images, for example a plurality of source-histological-images present in a three-dimensional source-histological image, as discussed further above. As will be discussed below, in a similar way to the system of FIG. 2, the system 300 of FIG. 3 generates first-tiles 306 that have a relatively large area (compared to second-tiles 307), generates second-tiles 307 that have a relatively high definition (compared to the first-tiles 306), and also has a classifier combiner 330. Also, the system 300 includes a machine-learning-network 311 that includes a representation network 308 (that may also be referred to as a first-neural-network) and a classification network 316 (which may also be referred to as a second-neural-network) that are similar to the corresponding components of FIG. 1.

The following discussion relates to use of the system 300 of FIG. 3 for external evaluation of a deep learning model for prediction of cancer-specific survival from colorectal cancer tissue sections, as represented by a WSI-histopathological image 324.

1.3.1 Training Cohorts:

Four training cohorts were utilised in this study. These were the Ahus cohort, the Aker cohort, the Gloucester cohort and the VICTOR cohort that are further described in the following subsections. Patients in the training cohorts were labelled as distinct or non-distinct prognosis depending on age at surgery and follow-up data. The distinct prognosis patients are comprised of patients defined as good prognosis and patients defined as poor prognosis. A patient was defined as good prognosis if aged less than 85 years at surgery, had more than 6 years follow-up after surgery, had no record of cancer-specific death and no record of recurrence. The availability of recurrence data varied between the cohorts and was particularly limited for the Gloucester cohort. For the Ahus cohort, good prognosis patients were required to have no record of metastasis (records of local recurrences were not available), while no record of local or metastatic recurrence were required for Aker, Gloucester and VICTOR patients. A patient was defined as poor prognosis if aged less than 85 years at surgery and suffered cancer-specific death between 100 days (inclusive) and 2.5 years (exclusive) after surgery. Patients not satisfying the criteria for either good or poor prognosis were defined as non-distinct prognosis.

1.3.1.1 Ahus Cohort

Figure 12:
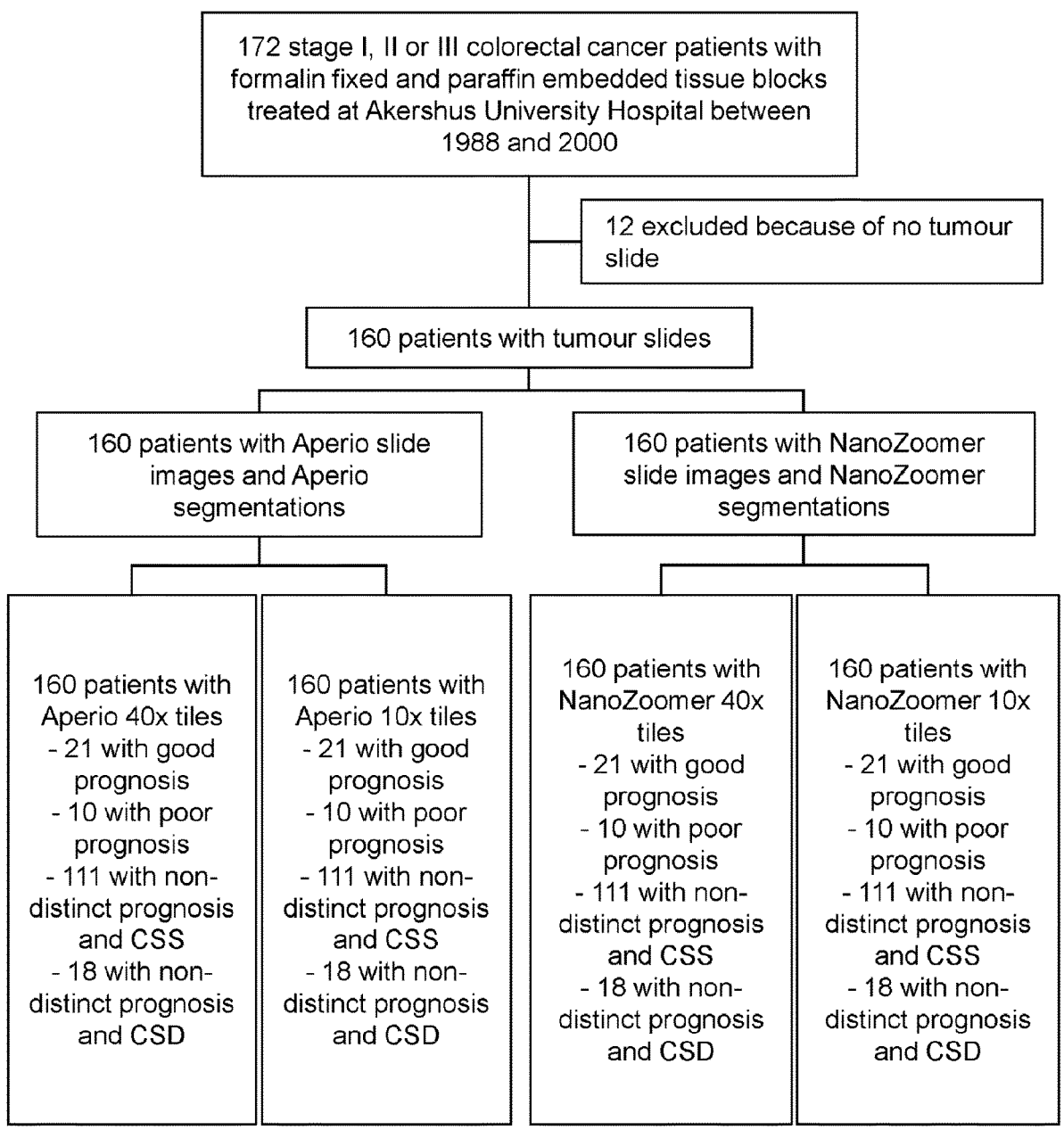
FIG. 12 shows a diagram specifying inclusions and exclusions of patients, slides and slide images from the Ahus cohort.

FIG. 12 shows a diagram specifying inclusions and exclusions of patients, slides and slide images from the Ahus cohort, and the prognosis of the included patients. CSS, cancer-specific survival; CSD, cancer-specific death.

From a consecutive series of 219 patients with colonic adenocarcinoma treated between 1988 and 2000 at Akershus University Hospital, Norway1, 172 patients had stage I, II or III disease and accessible formalin-fixed, paraffin-embedded (FFPE) tissue blocks. A 3 µm section of each FFPE tumour tissue block was stained with haematoxylin and eosin (H&E) and prepared as tissue slides by laboratory personnel at the Institute for Cancer Genetics and Informatics (ICGI), Oslo University Hospital, Norway. A pathologist ascertained whether there was tumour in each tissue section; the 12 patients without tumour slide were excluded (as shown in FIG. 12). The tumour tissue slides were scanned using two scanners, an Aperio AT2 (Leica Biosystems, Germany) and a NanoZoomer XR (Hamamatsu Photonics, Japan). The scans were read using the Python interface (version 1.1.1) of OpenSlide 3.4.1, available at https://openslide.org/. An automatic segmentation method (discussed below) was applied to identify tumour in the 320 slide images, and each slide image was partitioned into multiple non-overlapping regions called tiles using two resolution referred to as 40× and 10× (see Tiling section below). The 160 included patients with tiles within the tumour segmentation were defined as the Ahus cohort; FIG. 12 specifies the prognosis of these patients (see definition of distinct and non-distinct prognosis 2 above).

1.3.1.2 Aker Cohort

Figure 13:
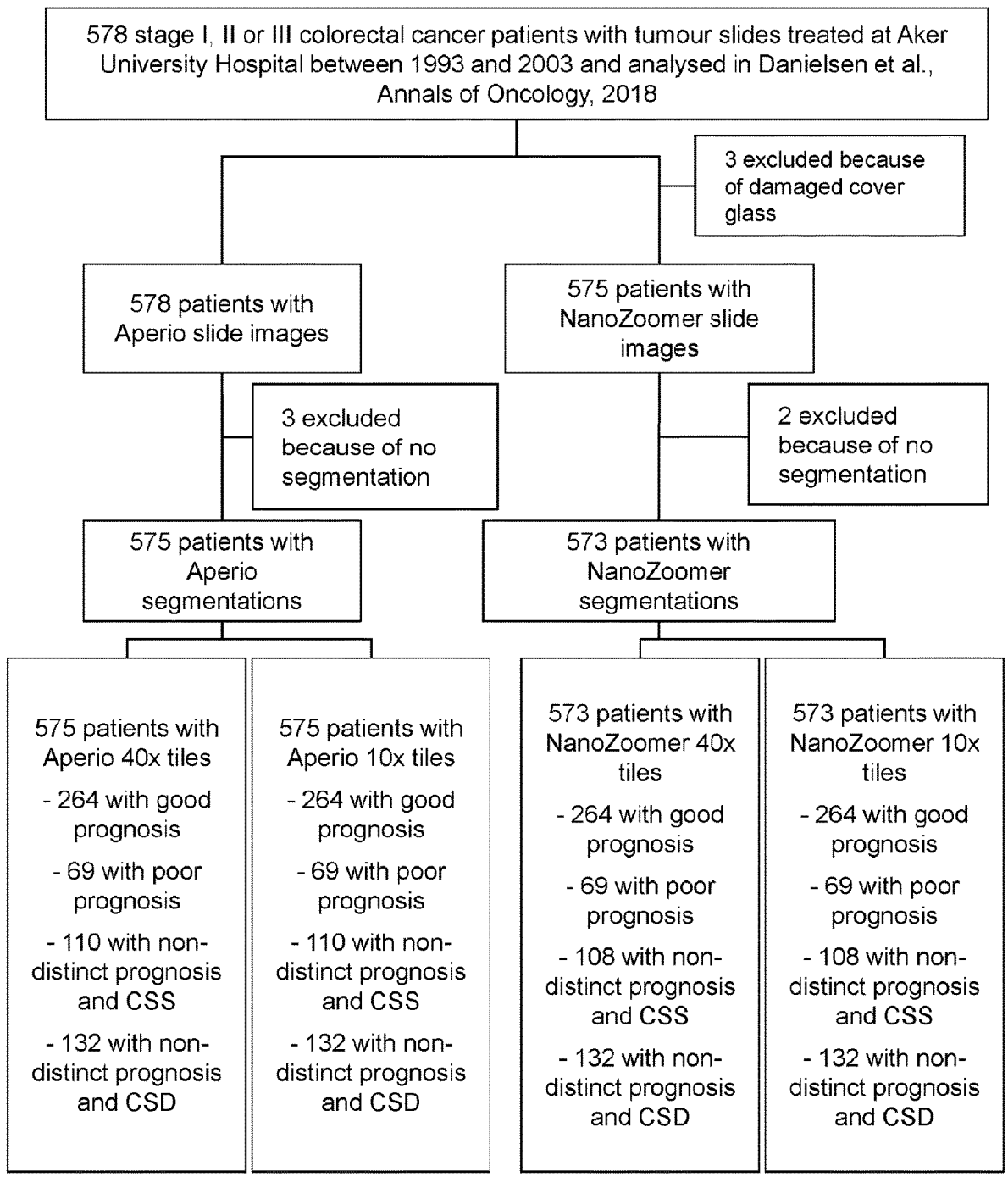
FIG. 13 shows a diagram specifying inclusions and exclusions of patients, slides and slide images from the Aker cohort.

FIG. 13 shows a diagram specifying inclusions and exclusions of patients, slides and slide images from the Aker cohort, and the prognosis of the included patients. CSS, cancer-specific survival; CSD, cancer-specific death.

One slide from each of the 578 stage I, II or III patients treated between 1993 and 2003 for primary colorectal cancer at Aker University Hospital, Norway, and analysed by Danielsen and colleagues were processed in the same manner as for the Ahus cohort. Three slides had damaged cover glass and could therefore not be scanned by the NanoZoomer XR scanner, and the automatic segmentation method identified no tumour for three Aperio AT2 slide images and two NanoZoomer XR slide images; the other patients comprised the Aker cohort (FIG. 13).

1.3.1.3 Gloucester Cohort

Figure 14:
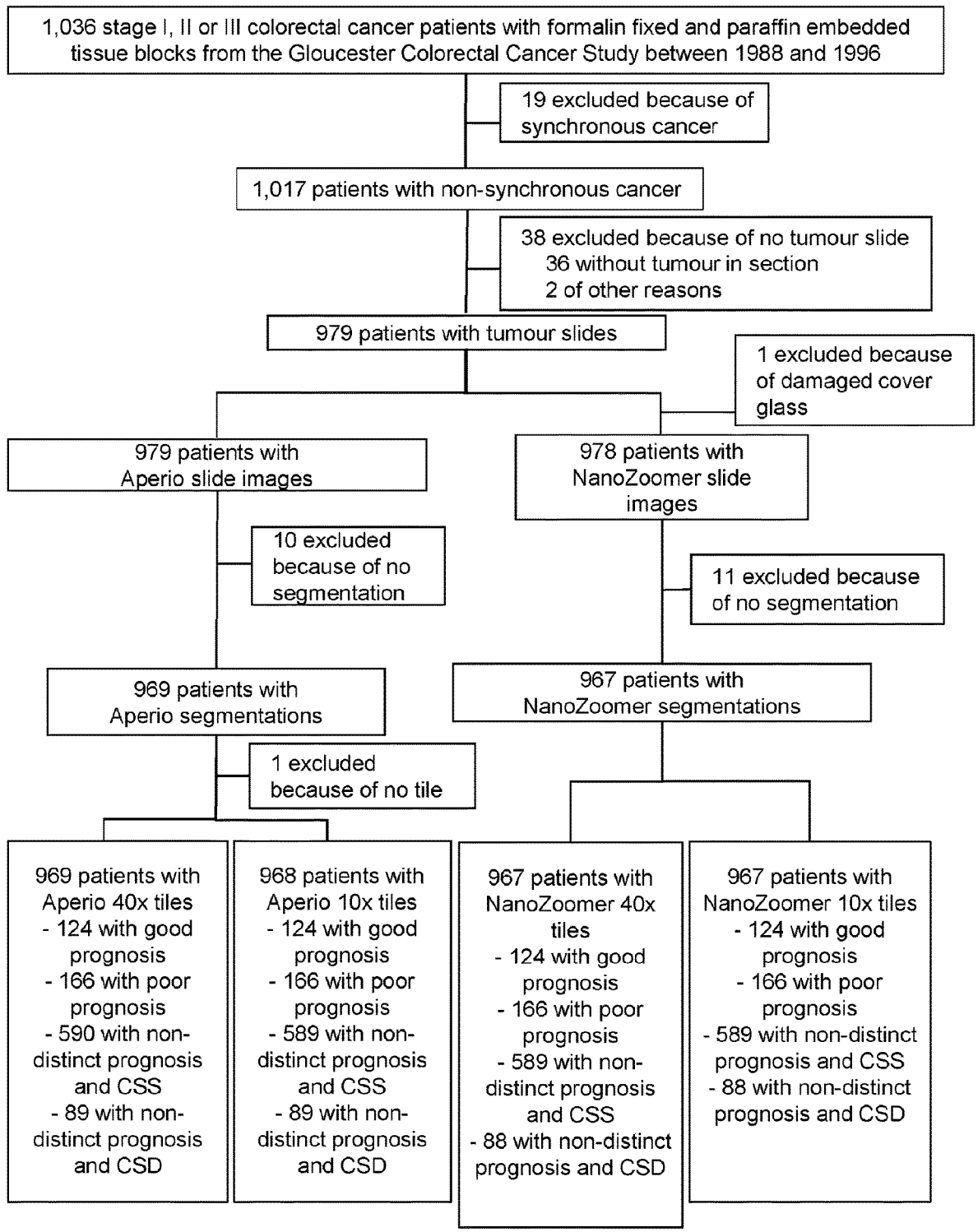
FIG. 14 shows a diagram specifying inclusions and exclusions of patients, slides and slide images from the Gloucester cohort.

FIG. 14 shows a diagram specifying inclusions and exclusions of patients, slides and slide images from the Gloucester cohort, and the prognosis of the included patients. CSS, cancer-specific survival; CSD, cancer-specific death.

The Gloucester Colorectal Cancer Study recruited 1,036 patients between 1988 and 1996, of which 19 were excluded because of synchronous cancer (FIG. 14). The remaining 1,017 patients were processed in the same manner as for the Ahus cohort, resulting in 969 patients with Aperio AT2 segmentations and 967 patients with NanoZoomer XR segmentations (FIG. 14). These patients constituted the Gloucester cohort, but one of them was excluded from the Aperio AT2 10× tile set because of no tile within the tumour segmentation (FIG. 14).

1.3.1.3 VICTOR Cohort

Figure 15:
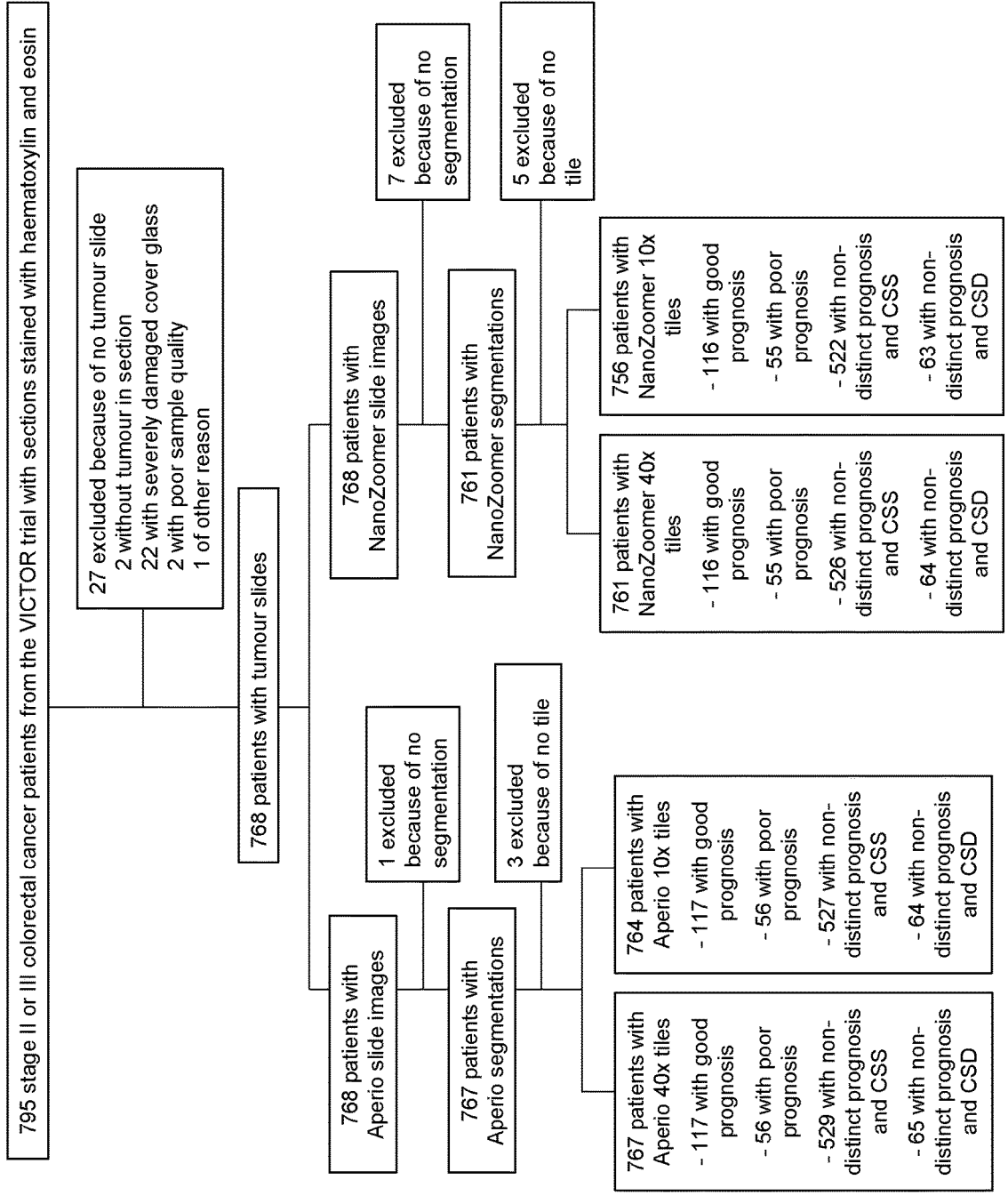
FIG. 15 shows a diagram specifying inclusions and exclusions of patients, slides and slide images from the VICTOR cohort.

FIG. 15 shows a diagram specifying inclusions and exclusions of patients, slides and slide images from the VICTOR cohort, and the prognosis of the included patients. CSS, cancer-specific survival; CSD, cancer-specific death.

The VICTOR trial randomised stage II and III colorectal cancer patients to receive rofecoxib or placebo after primary treatment in order to examine cardiovascular adverse events. An H&E-stained 3 µm section from a FFPE tissue block was retrieved for 795 of the patients recruited between 2002 and 2004, some of which were sectioned at ICGI and some of which were sectioned elsewhere.

The sections were processed in the same manner as for the Ahus cohort. The VICTOR cohort consisted of 767 patients with Aperio AT2 40× tiles, 764 patients with Aperio AT2 10× tiles, 761 patients with NanoZoomer XR 40× tiles and 756 patients with NanoZoomer XR 10× tiles (FIG. 15).

1.3.2 Segmentation:

As shown schematically in FIG. 3, a source-histological-image 302 is generated from the WSI-histological image 324, such as a WSI-histopathological image, by applying an image segmentation method.

The segmentation method in this example includes a process to produce probability maps from input images, and a different process to create an image partitioned into foreground and background regions based on the input image and the corresponding probability map.

Figure 4:
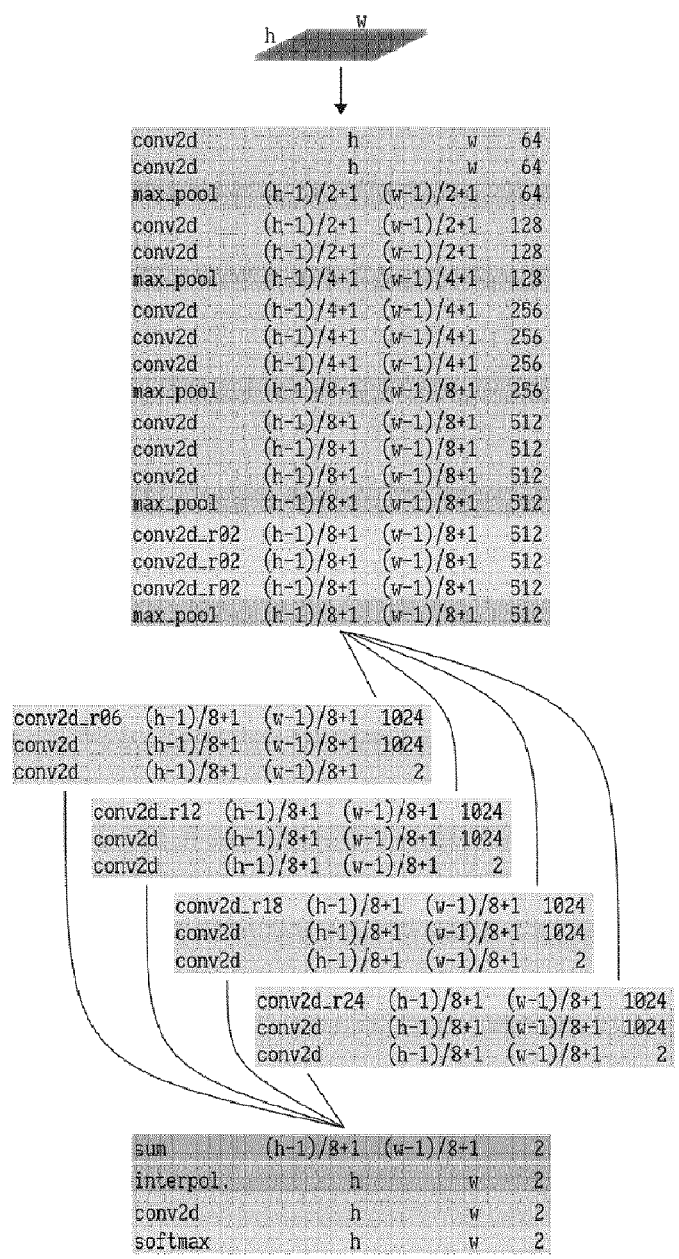
FIG. 4 shows an illustration of an example segmentation network architecture.

FIG. 4 shows an illustration of an example segmentation network architecture. Each layer is represented by name, output height, output width, and number of output channels. Progression is downwards from the input image at the top to the prediction output at the bottom. The probability maps can be generated by the segmentation network of FIG. 4, which is based on the DeepLab network (Chen et al., *IEEE Trans Pattern Anal Mach Intell*, 2018, 40: 834-848). The final segmentation can be achieved using dense conditional random fields (Krähenbühl, & Koltun, *Adv Neural Inf Process Syst*, 2011; 24: 109-117).

The method was initially trained on 1077 images with corresponding annotations from the Aker cohort (670 images) and VICTOR cohort (407 images). The images were obtained from slides scanned with a NanoZoomer (Hamamatsu Photonics, Japan) scanner, and the annotations was hand-drawn by a pathologist. This trained method was then applied on images from the Aker cohort, the Ahus cohort, and the Gloucester cohort. The resulting segmentations were verified by a pathologist, who corrected the ones that were unsatisfactory. This set of images with corresponding (possibly corrected) masks constitutes the development dataset of the image segmentation method.

From the development dataset of 1717 patients, 25% (429 patients) were drawn uniformly at random to form a tuning set, and the remaining 1288 patients comprised the training set. In the training set there were 358 patients with a cancer-specific event, and 930 images patients without. In the tuning set there were 128 images of patients with a cancer-specific event, and 301 patients without. Slides from patients in the segmentation development set were scanned with both an Aperio AT2 scanner and a NanoZoomer XR scanner. The development set in the segmentation task is therefore comprised of 3430 scans (4 scans from the NanoZoomer XR scanner were missing), with 2573 in the training set, and 857 in the tuning set.

Each scan was digitally resized to a size corresponding to a 2.5× resolution (see the Tiling section below), and stored as a PNG image. Each image was then resized to fit within a frame of 1600×1600 pixels with a Catmull-Rum cubic filter. This was done by resizing the image while preserving the aspect ratio until its largest dimension (height or width) is 1600 pixels. A new image was then formed by padding the resized image along its shortest dimension on each side until it also is 1600 pixels. The centre of the resized image aligns with the centre of the padded image, and the padded image is used further.

The segmentation network was trained with 100,000 update steps (training iterations), and each update step uses 16 images (this collection is called a mini-batch) distributed on 4 GPUs. Every image in the development dataset is used once before one is used twice, which means that each image is processed about 622 times during training (one progression through a dataset is termed an epoch). At each epoch, the same image is used once, but with slight variations each time. First, a section of 641×641 pixels is cropped at a random location within the image. Then, a set of orientation distortions are applied in the following order 1. With a probability of 50%, flip the image horizontally (mirror along its horizontal axis).
2. With a probability of 50%, flip the image vertically (mirrored along its vertical axis).
3. With a probability of 50%, rotate the image once with one of the following degrees: 0, 90, 180, 270.

Finally, the image is centred around its mean and standard deviation (see https://www.tensorflow.org/versions/r1.10/api_docs/python/tf/image/per_image_standardization). The resulting image is fed into the segmentation network as an RGB image.

The trainable parameters are initialized using a Xavier weight initialization scheme, and updated using a standard stochastic gradient descent optimization method (Glorot & Bengio, *Understanding the difficulty of training deep feedforward neural networks. in Proc 13th Int Conf Artif Intell Stat*, Vol. 9 249-256 (2010)). The step length in the optimization is initialized to 0.05, and decreased by a factor of 0.1 at iteration 96488 (about 600 training epochs).

Applying the trained network on an image yields a probability map with the same spatial shape as the image. This probability map is a one-channel grayscale image with intensity values in 0, 1, . . . , 255. The method assigns high values to regions it finds as probable of depicting cancerous tissue.

For each image, additional versions of the image are created by rotating and flipping the original image, before the trained network is applied to all the different versions. There are 8 versions, and they are obtained from the original image by the following operations:

1. Do nothing (this is the original image)
2. Flip the image around its horizontal axis
3. Flip the image around its vertical axis
4. Rotate the image 90 degrees clockwise
5. Rotate the image 180 degrees clockwise
6. Rotate the image 270 degrees clockwise
7. Rotate the image 90 degrees clockwise and flip the result around its horizontal axis
8. Rotate the image 270 degrees clockwise and flip the result around its horizontal axis The resulting probability maps are then restored to their original orientation, and an average image of all the different versions is computed and used further in the process.

At inference, the trained network is applied on one image at a time (i.e. with a batch-size of one), and contrary to the training phase, neither cropping nor orientation distortion is applied. However, it is important that every image is centred around its mean and standard deviation as was done in training. The network was implemented and run in Python 3.5 (https://www.python.org) using TensorFlow 1.10 (https://www.tensorflow.org).

Segmentation of the probability maps was performed using the Python library pydensecrf v1.0rc3 (https://github.com/lucasb-eyer/pydensecrf). The model used a unary potential (the probability map), a gaussian pairwise potential (addPairwiseGaussian(sxy=1, compat=1)), and a bilateral pairwise potential (addPairwiseBilateral(sxy=30, srgb=3, compat=100)). The resultant image with float values in (0, 1) is thresholded at 0.5 to produce a binary mask, where pixels with value less than 0.5 are labelled as background, and the rest as foreground.

The resulting segmentation is smoothed with a 5×5 mean filter, before foreground regions connected with an eight-neighbourhood with fewer than 20,000 pixels are removed.

Background regions fully contained within foreground regions are marked as foreground.

The method was applied on the tuning set every 4,000 iterations, and the predicted segmentations were evaluated against the reference segmentations. The model that achieved the highest mean bookmakers informedness score was then selected as the model to be used in the rest of the experiment.

Figure 5:
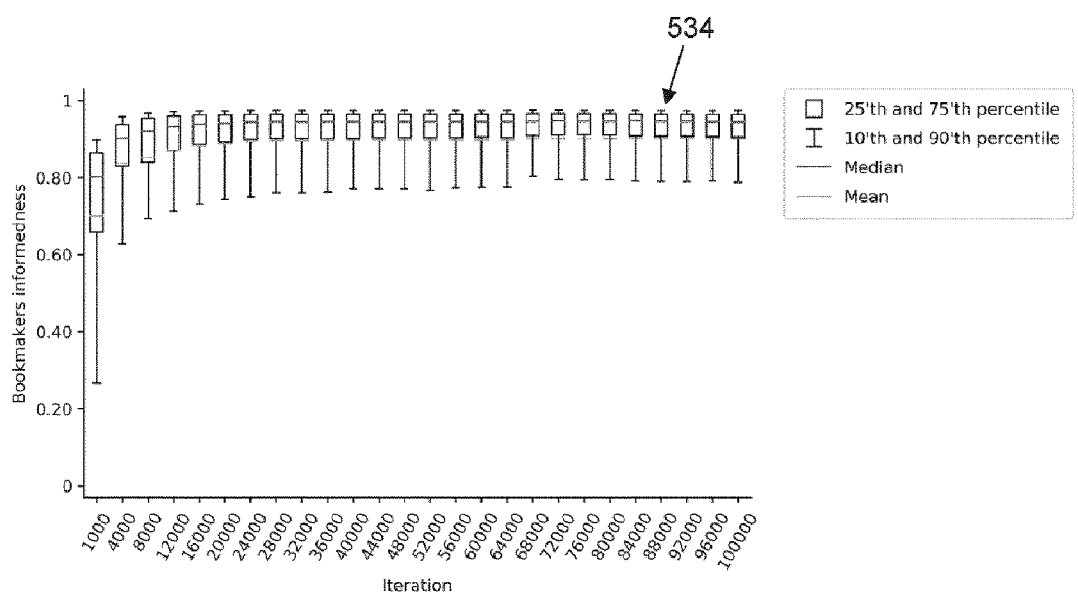
FIG. 5 shows the performance of the segmentation method on the tuning set.

FIG. 5 shows the performance of the segmentation method on the tuning set. As indicated above, the method is evaluated at multiple training iterations evenly spaced across the training progression every 4,000 iterations. FIG. 5 shows that the model at iteration 88,000 (reference number 534 in FIG. 5) achieved the highest score of 0.902.

Returning to FIG. 3, the output of the segmentation method is the source-histopathological-image 302.

1.3.3 Tiling:

The region identified as tumour by the segmentation method is the source-histopathological-image 302, which in this example is not directly suitable for use as an input to a convolutional neural network (CNN) because of limited GPU memory in commonly available hardware. Therefore, this process generated multiple non-overlapping regions of a fixed size, called tiles, from within the source-histological-image 302 (i.e. the region segmented as tumour in each slide image). It will be appreciated that an equivalent approach can be adopted to generate tiles from any region of interest within a source-histological-image 302 (for example, in source-histological-images which are, or are not, taken from histological samples of any other types of cancer and/or any other pathological condition).

In FIG. 3, a plurality of first-tiles 306 and a plurality of second-tiles 307 are shown. In the same way as for FIG. 2, the first-tiles 306 have a relatively large area and a relatively low resolution, and the second-tiles 307 have a relatively small area and a relatively high resolution.

Since the physical area represented by a pixel can depend on the scanner used to obtain the image, as well as other things, the tiles representing the same physical area were created by including slightly different number of pixels in tiles from Aperio AT2 and NanoZoomer XR slide images. At maximum resolution, termed 40×, pixels in the Aperio AT2 slide images had a physical size of 0.253 µm/pixel both vertically and horizontally, while pixels in the NanoZoomer XR slide images had 0.227 µm/pixel both vertically and horizontally. To make the 40× tiles (the second-tiles 307 with the higher resolution), tiles with 486×486 pixels were extracted from within the tumour segmentation of Aperio AT2 slide images, while 542×542 pixels were used for NanoZoomer XR slide images. Similarly, a tile size of 1942×1942 pixels were used for Aperio AT2 slide images and 2166×2166 pixels for NanoZoomer XR slide images to make 10× tiles (which are the first-tiles 306, with the lower resolution). Each of these raw tiles was then resampled to 512×512 pixels, making the physical area of each pixel similar for both scanners, 0.240×0.240 µm for 40× tiles and 0.960×0.960 µm for 10× tiles.

In this example, the tiling was performed by defining a grid of candidate tiles from the top left corner of the WSI-histological image 324, including regions outside the tumour segmentation (as represented by the source-histological-image 302). Candidate tiles for which the four corners and their midpoints along the edges were within the boundaries of the segmentation were included as a first-tile 306 or a second-tile 307. Tiles were extracted with OpenSlide from level 0, converted to numpy arrays, resized with OpenCV using the resize( ) function (https://docs.opencv.org/3.4.0/da/d54/group_imgproc__transform.html) with interpolation set to cv2.INTER_CUBIC for up-sampling and cv2.INTER_AREA for down-sampling and saved in a lossless format (as PNG files).

1.3.4 Patient Survival Prediction Method—Using the Machine-Learning-Network 311

The machine-learning-network 311 was trained using all patients with distinct prognosis in the training cohorts. As will be described in detail below, the machine-learning-network 311 was trained five times with 40× tiles (Models 1 to 5 on second-tiles 307 in FIG. 3) and another five times with 10× tiles (Models 6 to 10 on first-tiles 306); the resampled tiles with 512×512 pixels were used in both cases. The applied ground-truth (i.e. true outcome, as represented by truth-data 320) in these supervised classification methods was the patient's distinct prognosis, either good or poor prognosis (as defined above in the Training Cohort section).

The machine-learning-network 311 is a multiple instance classification method that includes a representation network 308 (corresponding to the first-neural-network of FIG. 1), a pooling function 312 (corresponding to the pooling-function of FIG. 1), and a classification network 316 (corresponding to the second-neural-network of FIG. 1).

Figure 6:
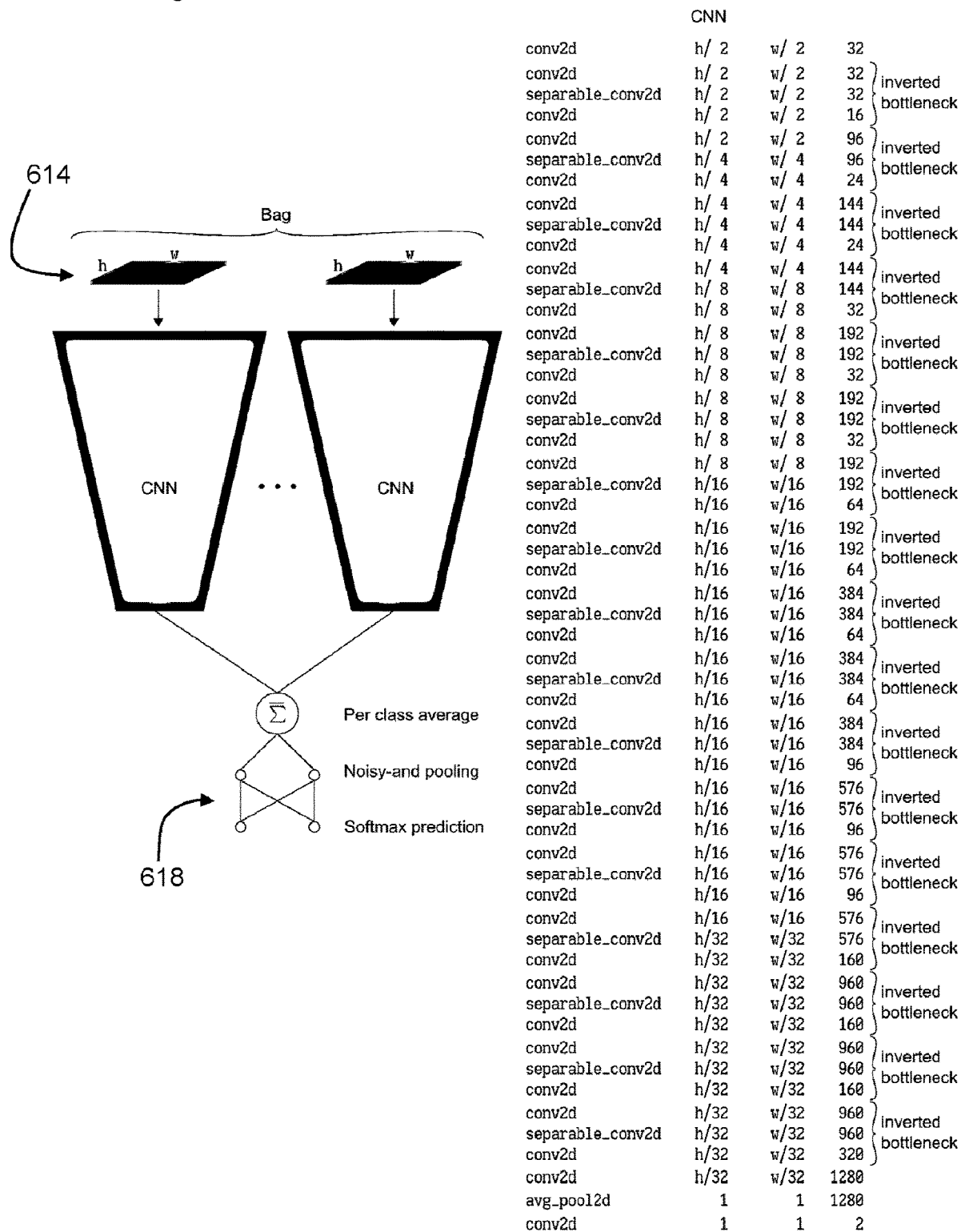
FIG. 6 shows an illustration of this implementation of the machine-learning-network architecture of FIG. 3.

FIG. 6 shows an illustration of this implementation of the machine-learning-network architecture of FIG. 3. The left side gives an overview over progression from an input bag of tiles 614 to a bag prediction (a classifier 618 that is output by the machine-learning-network). The right side shows the architecture of the representation network 608 (corresponding to the first-neural-network of FIG. 1), where each layer is represented by name, output height, output width, and number of output channels.

Returning to FIG. 3, rather than classifying a single tile, the machine-learning-network 311 classifies a collection of tiles called a bag, where all tiles within a bag originate from the same scan image (the WSI-histological image 324/the source-histological-image 302). Each tile in a bag is applied to the representation network 308 to produce a tile-feature 310 of the tile (note that within one update step, all tiles can use the same representation network with the same parameter values). All tile-features can be aggregated and a single value for each class can produced by the pooling function 312. A final classification network 316 is then applied, and a prediction is produced. These predictions are compared with the ground-truth (as represented by the truth data 320) corresponding to the source-histological-image 302 from which the bag originates, using a loss function.

In this example, the loss function is optimised using a gradient-based optimisation routine, and at each training iteration the trainable parameters of the machine-learning-network 311 are updated according to this optimisation method. In this example, only a randomly selected subset of the tiles in the bag is used to update the machine-learning-network 311. This asymmetric forward and backward propagation reduces the memory footprint of the machine-learning-network 311, and allows larger bags of tiles during training.

As indicated above, the representation network 308 in this implementation is based on the MobileNetV2 network, and its details are illustrated in FIG. 6 (Sandler, M., Howard, A., Zhu, M., Zhmoginov, A. & Chen, L. *MobileNetV2: Inverted Residuals and Linear Bottlenecks. in IEEE Conf Comput Vis Pattern Recognit* 4510-4520 (2018)). The first convolution layer in the representation network uses a 3×3 convolution kernel with a stride of 2. The activation function is a ReLU activation function (Glorot, X., Bordes, A. & Bengio, Y. *Deep Sparse Rectifier Neural Networks. in Proc 14th Int*

*Conf Artif Intell Stat*, Vol. 15 315-323 (2011)). Inside each inverted bottleneck module, the first convolution layer uses a 1×1 convolution kernel with a stride of 1 and a ReLU6 activation function (Krizhevsky, A. Convolutional Deep Belief Networks on CIFAR-10. Available from: https://www.cs.toronto.edu/~kriz/conv-cifar10-aug2010.pdf. (2010)). The depth-wise separable convolution layer uses a 3×3 convolution kernel. Whenever the spatial size halves in height and width, the stride is 2, otherwise it is 1. The activation function is the ReLU6 function. The last convolution layer uses a 1×1 convolution kernel with a stride of 1, and an identity activation function. When the number of input channels to the inverted bottleneck module is equal to the number of output channels in the same module, the input to the first convolution layer within the module is added to the result of the last convolution layer within the module. The convolution layer after the inverted bottleneck modules uses a 1×1 convolution with stride 1 and the ReLU activation function. All convolution and separable convolution layers described above employ batch normalization on the result of the convolution, before the activation function is applied (Ioffe, S. & Szegedy, C. *Batch normalization: accelerating deep network training by reducing internal covariate shift*. in *Proc* 32*nd Int Conf Mach Learn*, Vol. 37 448-456 (2015)). All kernel weights are initialised with Xavier initialization, and no bias parameters are used. The final convolution layer uses a 1×1 convolution kernel with stride 1. No batch normalization is used in this layer, and the activation is the identity function. The rest of the network consists of a noisy- and pooling function followed by a softmax classification, following the design of Kraus and colleagues (Kraus, O. Z., Ba, J. L. & Frey, B. J. *Classifying and segmenting microscopy images with deep multiple instance learning. Bioinformatics* 32, i52-i59 (2016).). There is one cross-entropy loss function associated with the output of the pooling function, and one cross-entropy loss function associated with the classification output.

The machine-learning-network 311 network was trained with a batch size of 32 bags, distributed across 8 GPUs with 4 bags on each GPU. Each bag consisted of 64 tiles with size 512×512×3 pixels and with values in 0, 1, . . . , 255. The number of tiles contributing to the gradient computation was 8. For updating the network parameters, an initial step size of 0.001 was used with the Adam optimisation method (Kingma, D. P. & Ba, J. Adam: *A Method for Stochastic Optimization*. Available from: https://arxiv.org/abs/1412.6980. (2015)). When training on 10× tiles (the first-tiles 306), the learning rate was initially set to 0.001 and then successively reduced by a factor of 0.1 at iteration 6,000 and again at iteration 12,000 before training ceased after iteration 15,000. Twice the number of iterations were utilised to train on 40× tiles (the second-tiles 307), i.e. the learning rate started at 0.001 and was successively reduced by a factor of 0.1 at iteration 12,000 and again at iteration 24,000 before training ceased after iteration 30,000.

At each step, before entering the machine-learning-network 311, each tile is distorted and normalised. First, it is randomly cropped to a size of 448×448, before the orientation of the tile is distorted. The tile is randomly flipped from left to right (around its central vertical axis), then randomly flipped from top to bottom (around its central horizontal axis), and finally randomly rotated by either 0°, 90°, 180° or 270°. Then its values are scaled to (0, 1) by casting it to a 32-bit floating point number before dividing the entire tile by 255.0. The tile is then converted from the RGB colour space to the HSV colour space before each channel is scaled with a value uniformly distributed between 1/1.1 and 1.1.

The tile is then converted back to RGB. Finally, the tile is normalised to have zero mean and unit norm (see rgb_to_hsv, hsv_to_rgb, per_image_standardization at https://www.tensorflow.org/versions/r1.10/api_docs/python/tf/image for more information).

At inference, no cropping is applied, so the entire tile of size 512×512×3 pixels is evaluated by the machine-learning-network 311. Also, no orientation or colour distortions are applied. Before entering the machine-learning-network 311, each tile is normalised to have zero mean and unit norm as in training. The network was implemented and run in Python 3.5 (https://www.python.org) using TensorFlow 1.10 (https://www.tensorflow.org). To account for class imbalance in the training set, the minority class within a cohort-scanner combination was oversampled such that there was an equal number of images labelled with good prognosis and poor prognosis in every cohort-scanner combination. Within each cohort-scanner combination, images were sampled uniformly at random without replacement.

1.3.5 Another Network Used for Comparison—Inception v3 Network

Another network, an Inception v3 network (Szegedy, C., Vanhoucke, V., Ioffe, S., Shlens, J. & Wojna, Z. *Rethinking the Inception Architecture for Computer Vision*. in *Proc* 2016 *IEEE Conf Comput Vis Pattern Recognit* 2818-2826 (2016)), was used to obtain classification results for comparison with the results of the machine-learning-network 311 of FIG. 3.

The Inception v3 network was trained with Keras (2.1.6) using the Tensorflow Docker image (tensorflow/tensorflow: 1.9.0-gpu-py3). The input image size was 512×512 and the output was two classes with the first class being the probability of good prognosis and the second class the probability of poor prognosis. A binary cross entropy loss function was used, and it was optimised with keras.optimizers.Adam using default arguments, except for initial learning rate which was set to 0.0001. To account for class imbalance between tiles from good and poor prognosis, tiles from the minority class were oversampled per cohort prior to training and the file paths were saved as a list. Consequently, each cohort contained the same number of included tiles with good and poor prognosis, at the expense of potentially including some tiles twice. The list of tiles was loaded prior to training and randomly shuffled before a modified version of keras.preprocessing.image.ImageDataGenerator was utilised to load batches of images using 16 worker threads. The ImageDataGenerator was modified to perform colour distortion by:

1. converting the tile to HSV colour space,
2. augmenting the hue by adding a random uniformly sampled value between ±0.05,
3. scaling the saturation by a random uniformly sampled value between 1/1.1 and 1.1,
4. shifting the saturation by a random uniformly sampled value between ±0.1,
5. scaling the value by a random uniformly sampled value between 1/1.1 and 1.1,
6. shifting the value by a random uniformly sampled value between ≅0.1, and
7. converting the tile back to the RGB colour space.

The tile was then standardised by subtracting the mean colour values and dividing by the standard deviation of all tiles used for training, i.e. all tiles of patients with distinct prognosis in the training cohorts. For each training iteration, a batch size of 16 tiles was used due to GPU memory constraints. When training on 10× tiles, the learning rate was initially set to 0.0001 and then successively halved for each 25,000$^{th}$ iteration, starting at iteration 25,000, before training ceased after iteration 150,000. Twice the number of iterations were utilised to train on 40× tiles (second-tiles), i.e. the learning rate started at 0.0001 and was successively halved for each 50,000$^{th}$ iteration, starting at iteration 50,000, before training ceased after iteration 300,000. The network output was the predicted probability of poor prognosis for a tile. The predicted probability of poor prognosis for a patient was computed by averaging the predicted probabilities of all tiles for that patient.

1.3.6 Individual Models

Training each of the two networks ((i) the machine-learning-network 311 of FIG. 3, and (ii) the Inception v3 network) five times for each of the two resolutions resulted in 20 training runs. For each of these 20 training runs, 21 models were evaluated on all patients with non-distinct prognosis in the training cohorts. The 21 models evaluated for each training run were uniformly distributed from ⅓ of the iterations to the training ceased (both ends inclusive). Each 10× model of the machine-learning-network 311 was evaluated at iteration 5,000, 5,500, and so on up to iteration 15,000. Each 40× model of the machine-learning-network 311 was evaluated at iteration 10,000, 11,000, and so on up to iteration 30,000. Each 10× model of the Inception v3 network was evaluated at iteration 50,000, 55,000, and so on up to iteration 150,000. Each 40× model of the Inception v3 network was evaluated at iteration 100,000, 110,000, and so on up to iteration 300,000.

To reduce evaluation time for the 40× models, a random sample of 2,000 40× tiles were selected for each slide with more than 2,000 40× tiles. The same tiles were evaluated for all models. To reduce further the evaluation time for the 40× models of the machine-learning-network 311, patients with more than 50 tiles were evaluated using 50 tiles at a time, resulting in that tiles ordered after the last multiple of 50 were ignored in these evaluations, i.e. at most 49 tiles were ignored for each patient. Note that these speed-ups were only applied during model selection; for all applications of the selected models, including the external evaluation described in this document, all tiles will be evaluated.

The model that maximised Harrell's concordance index (Harrell, F. E., Jr, Califf, R. M., Pryor, D. B., Lee, K. L. & Rosati, R. A. *Evaluating the yield of medical tests. J Am Med Assoc* 247, 2543-2546 (1982)) (c-index) was selected for each training run. The c-index compared the observed time to cancer-specific death or censoring to a model's predicted probability of poor prognosis for patients with non-distinct prognosis in the training cohorts. The model with largest c-index thus appeared to provide most prognostic information in its predicted probabilities when evaluated on non-distinct prognosis patients in the training cohorts.

FIGS. 7-10 show the c-index of all candidate models and indicate the selected model for each of the 21 training runs.

Figure 7:
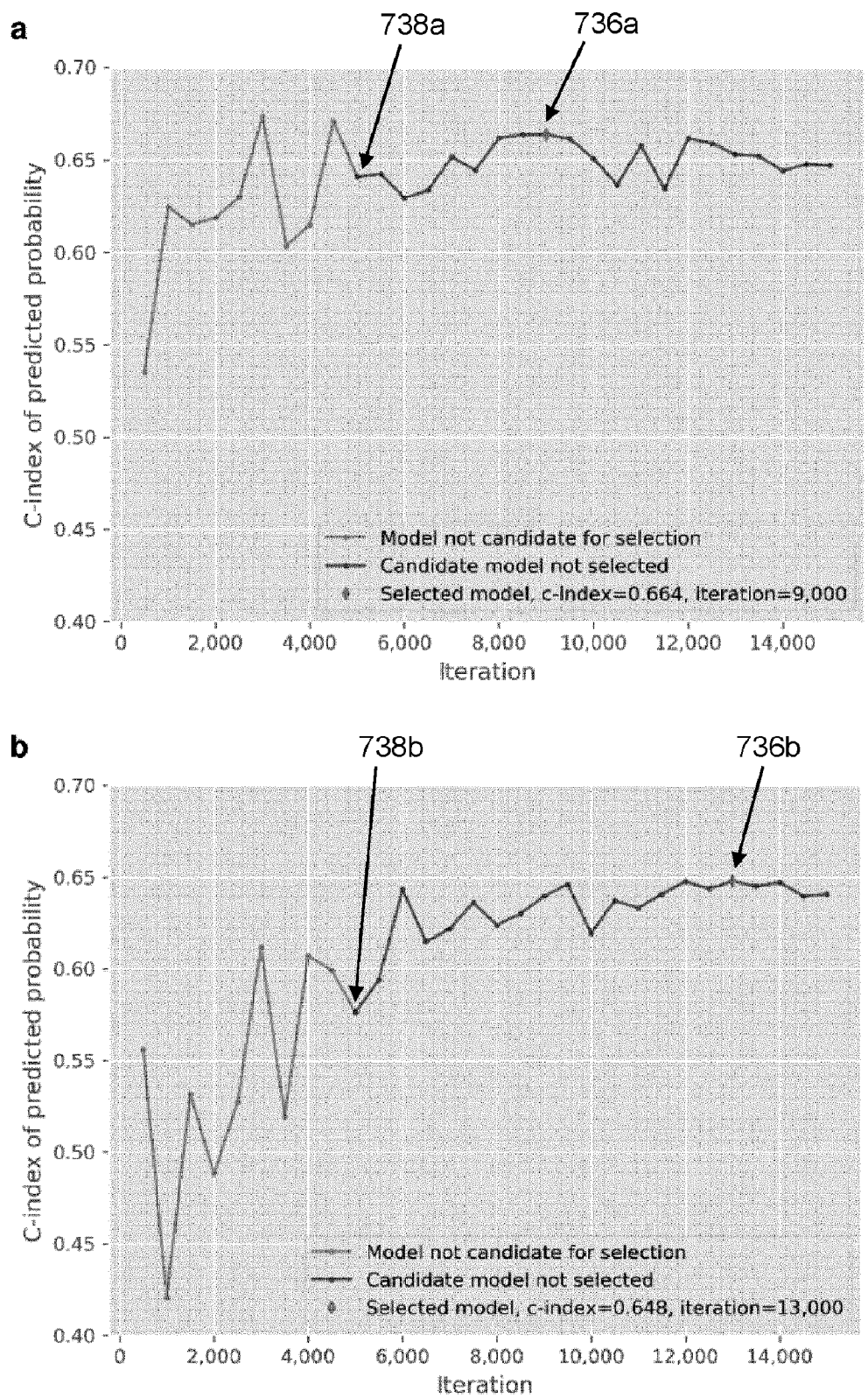
FIG. 7 shows the c-index of the 21 candidate 10× models of the machine-learning-network of FIG. 3 for patients with non-distinct prognosis in the training cohorts.
Figure 7:
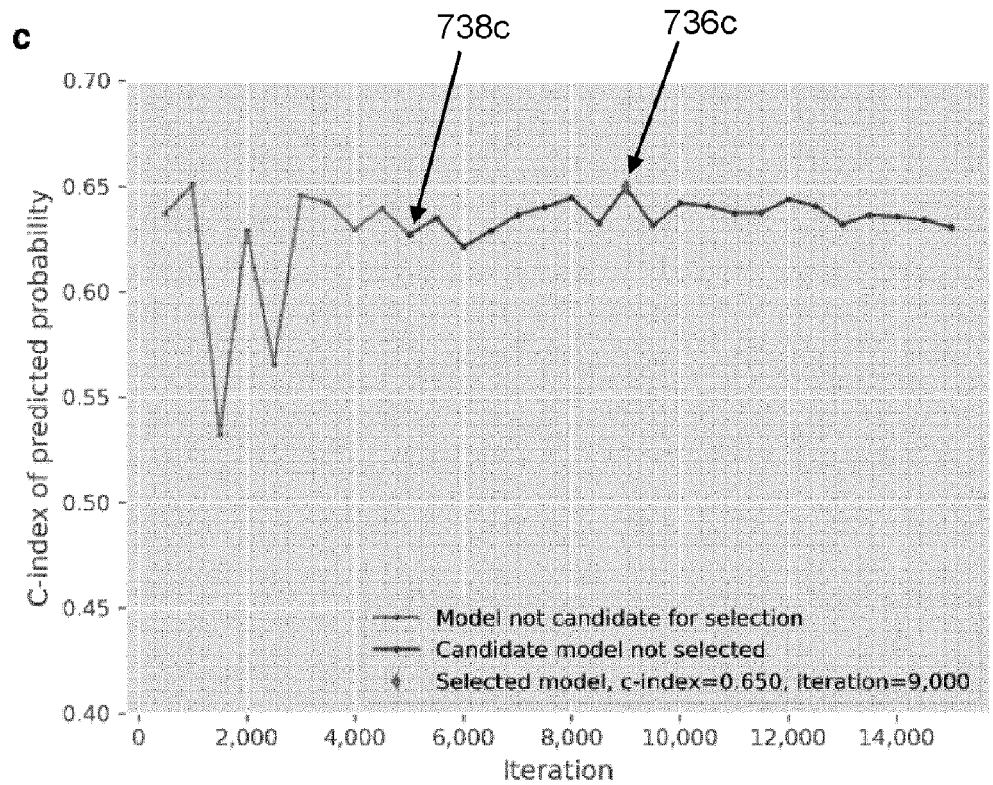
Figure 7:
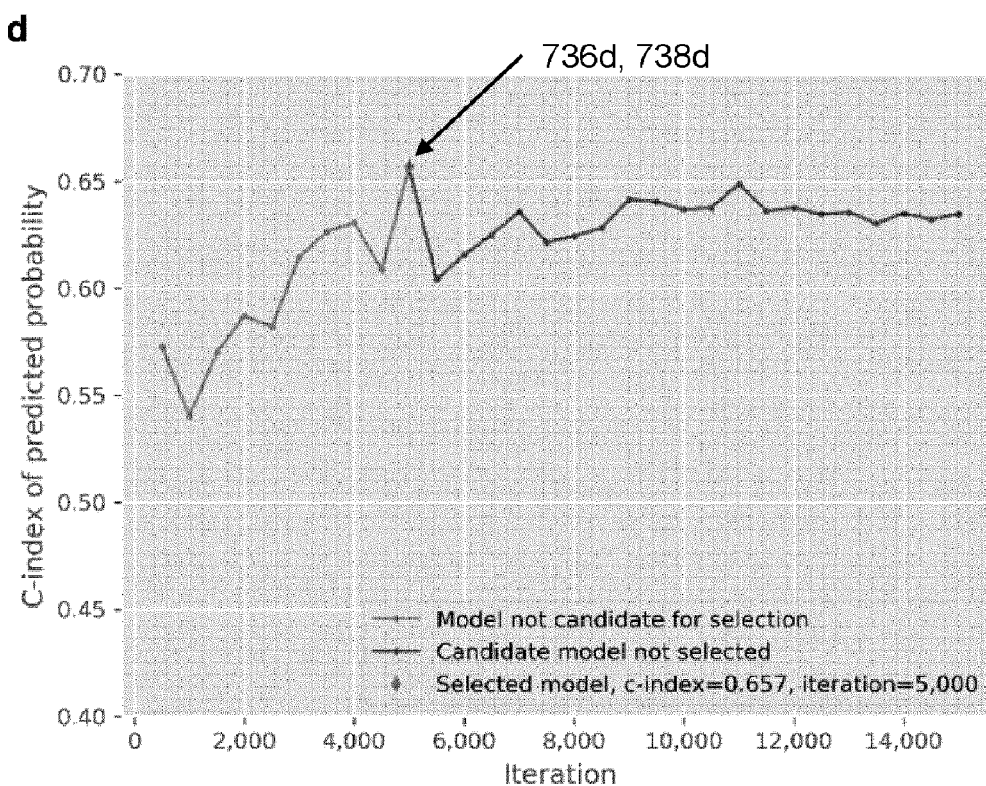
Figure 7:
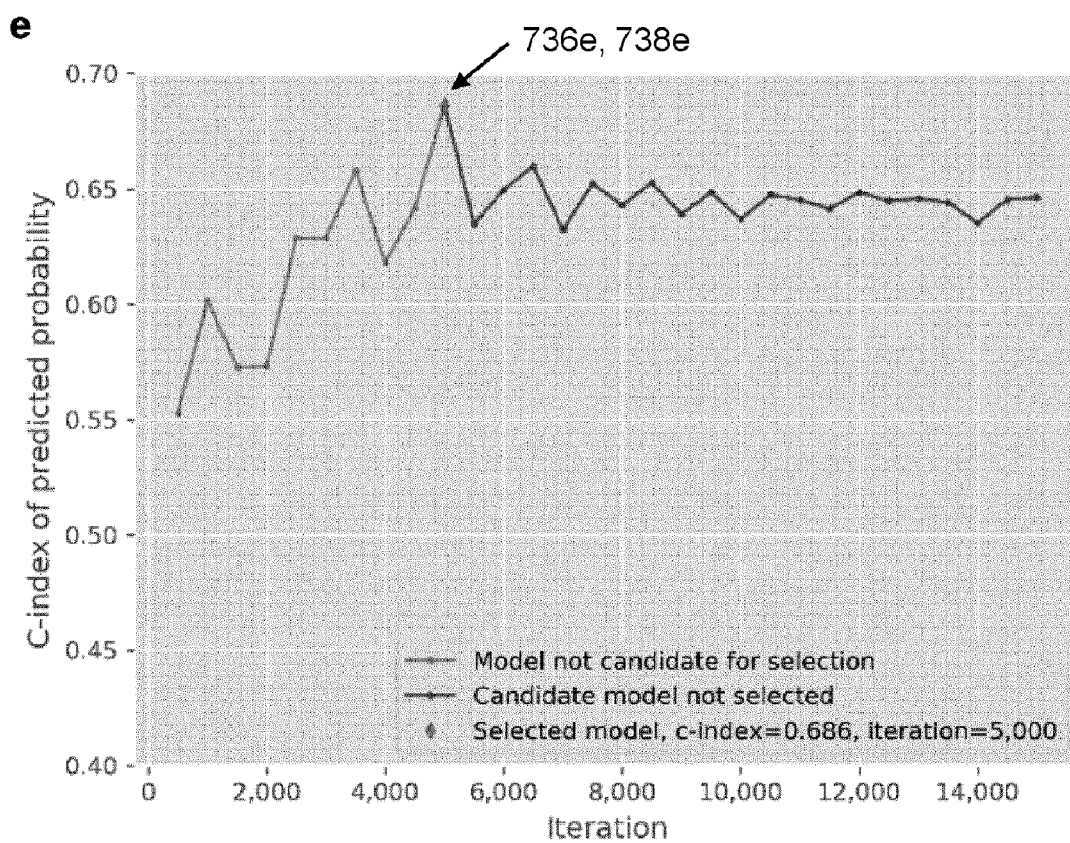

FIG. 7 shows the c-index of the 21 candidate 10× models of the machine-learning-network 311 for patients with non-distinct prognosis in the training cohorts. Subplots a to e show training runs 1 to 5. The points referenced as 736*a-e* indicate the selected model. The points including and after the ones referenced 738*a-e* (apart from 736*a-e* of course) indicate models not selected. The c-index of nine models from the first third of each training run (the models before the ones referenced 738*a-e*) are shown for comparison.

Figure 8:
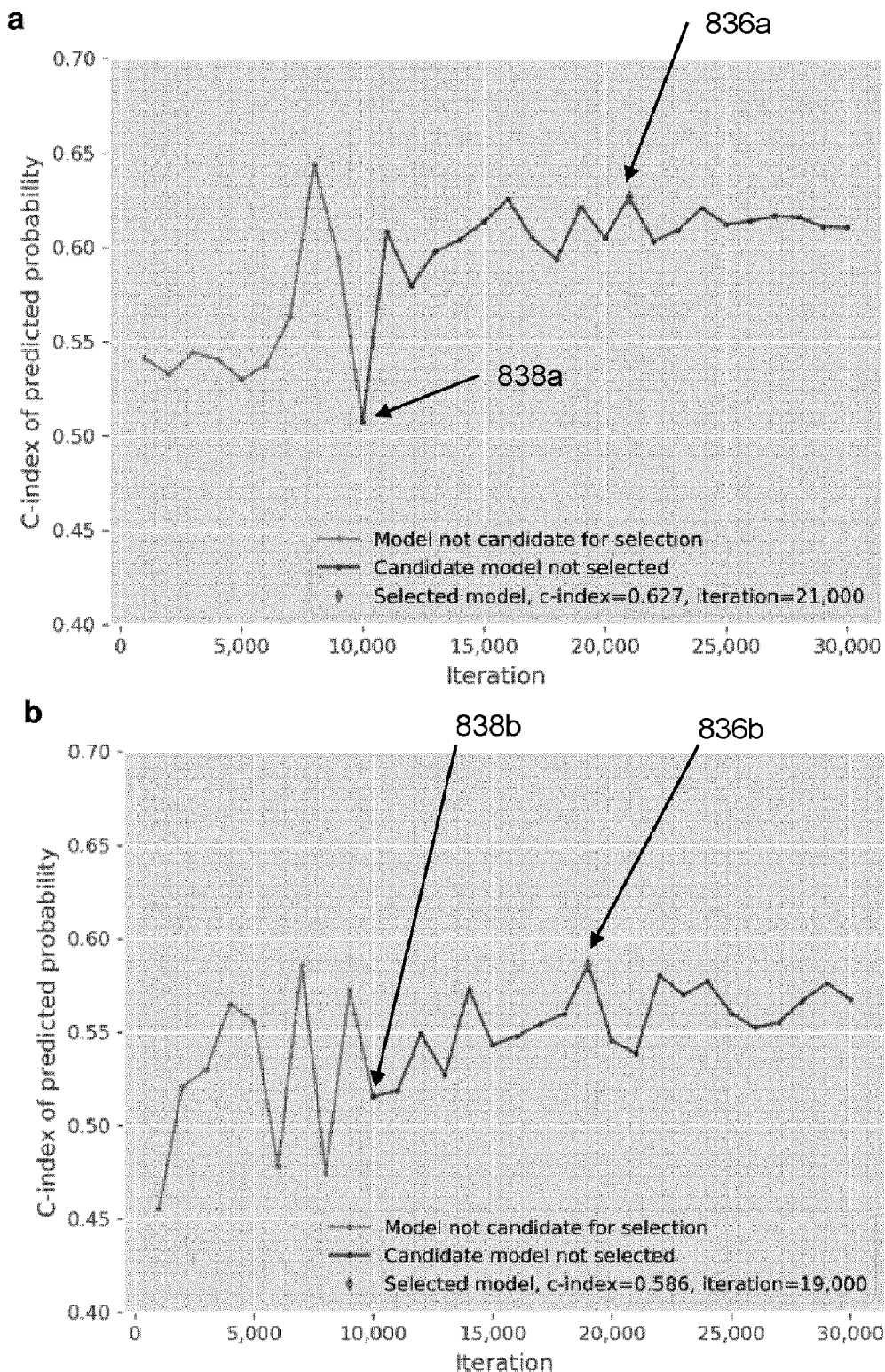
FIG. 8 shows the c-index of the 21 candidate 40× models of the machine-learning-network of FIG. 3 for patients with non-distinct prognosis in the training cohorts.
Figure 8:
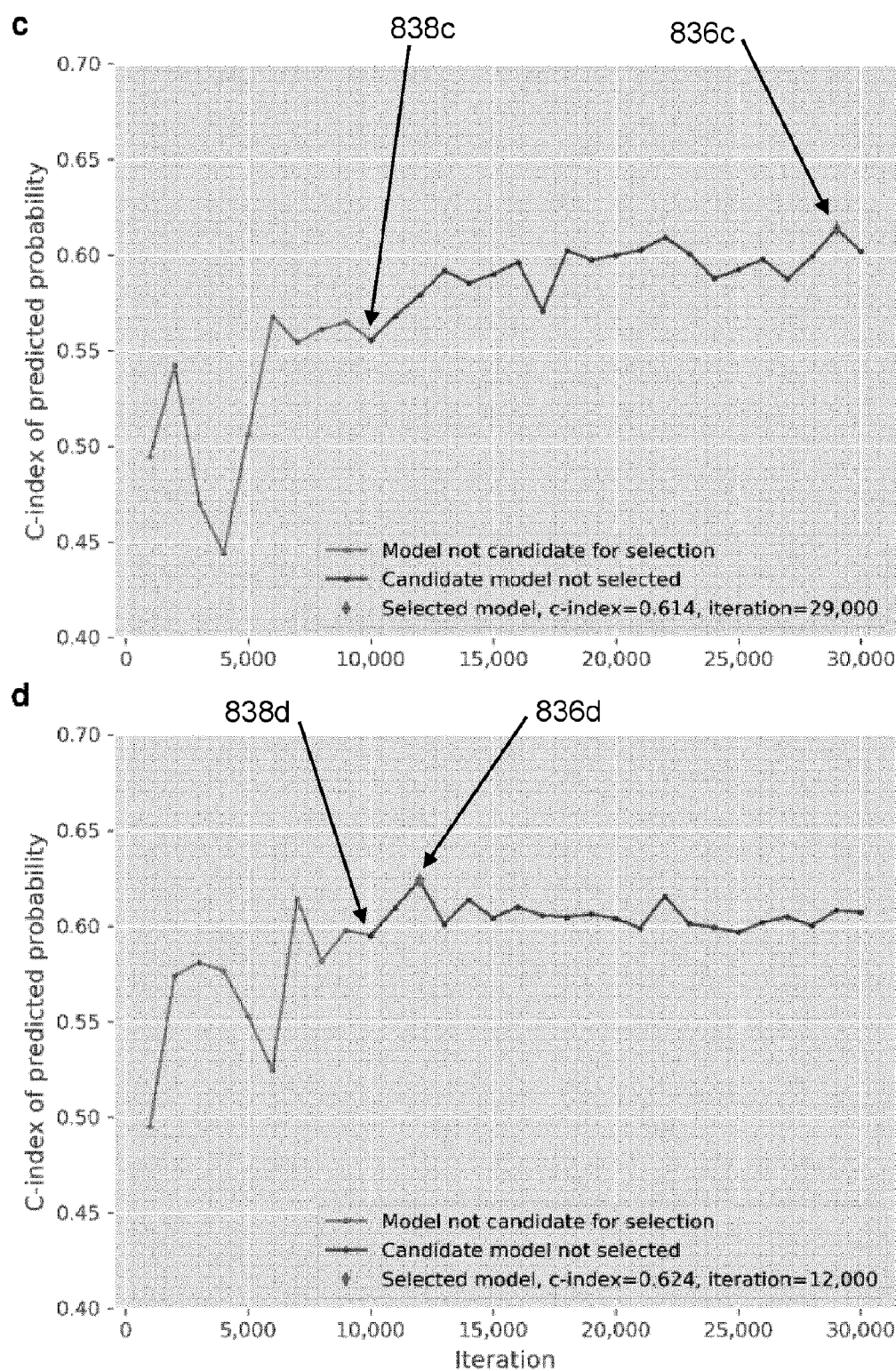
Figure 8:
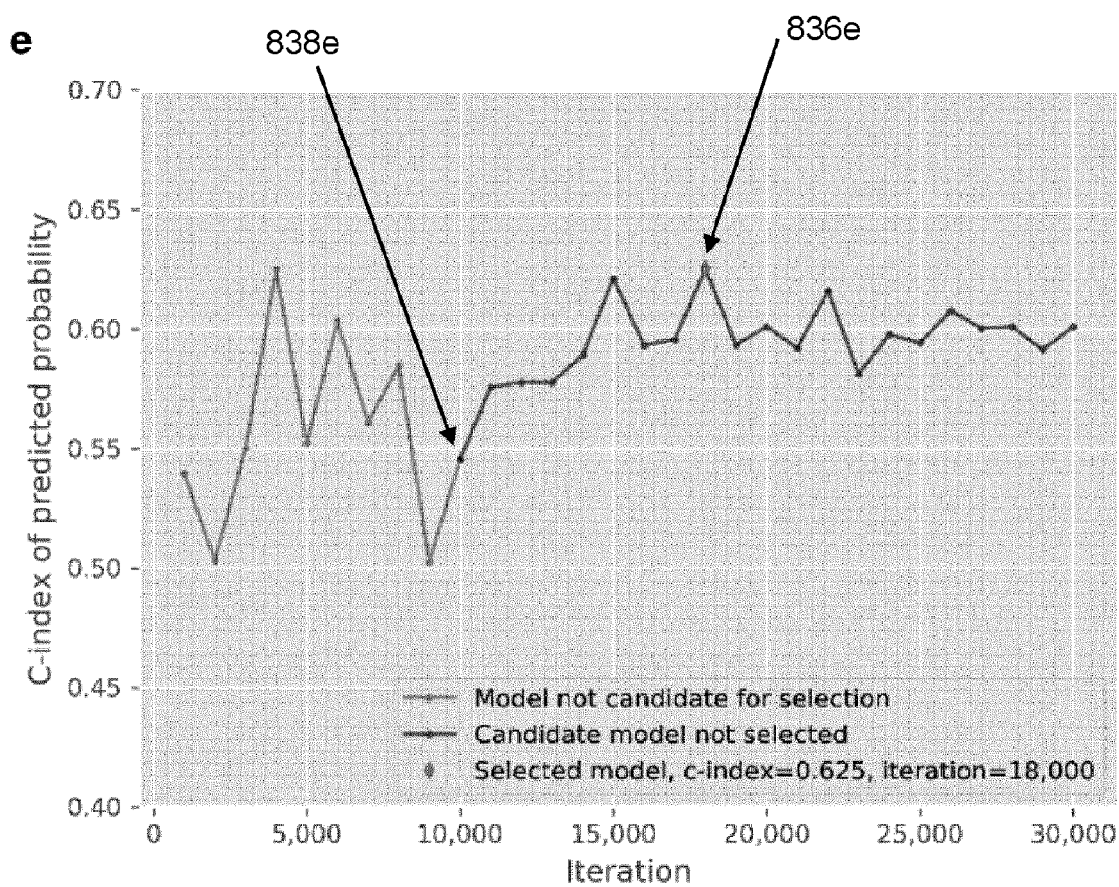

FIG. 8 shows the c-index of the 21 candidate 40× models of the machine-learning-network 311 for patients with non-distinct prognosis in the training cohorts. Subplots a to e show training runs 1 to 5. The points referenced as 836*a-e* indicate the selected model. The points including and after the ones referenced 838*a-e* (apart from 836*a-e* of course) indicate models not selected. The c-index of nine models from the first third of each training run (the models before the ones referenced 838*a-e*) are shown for comparison.

Figure 9:
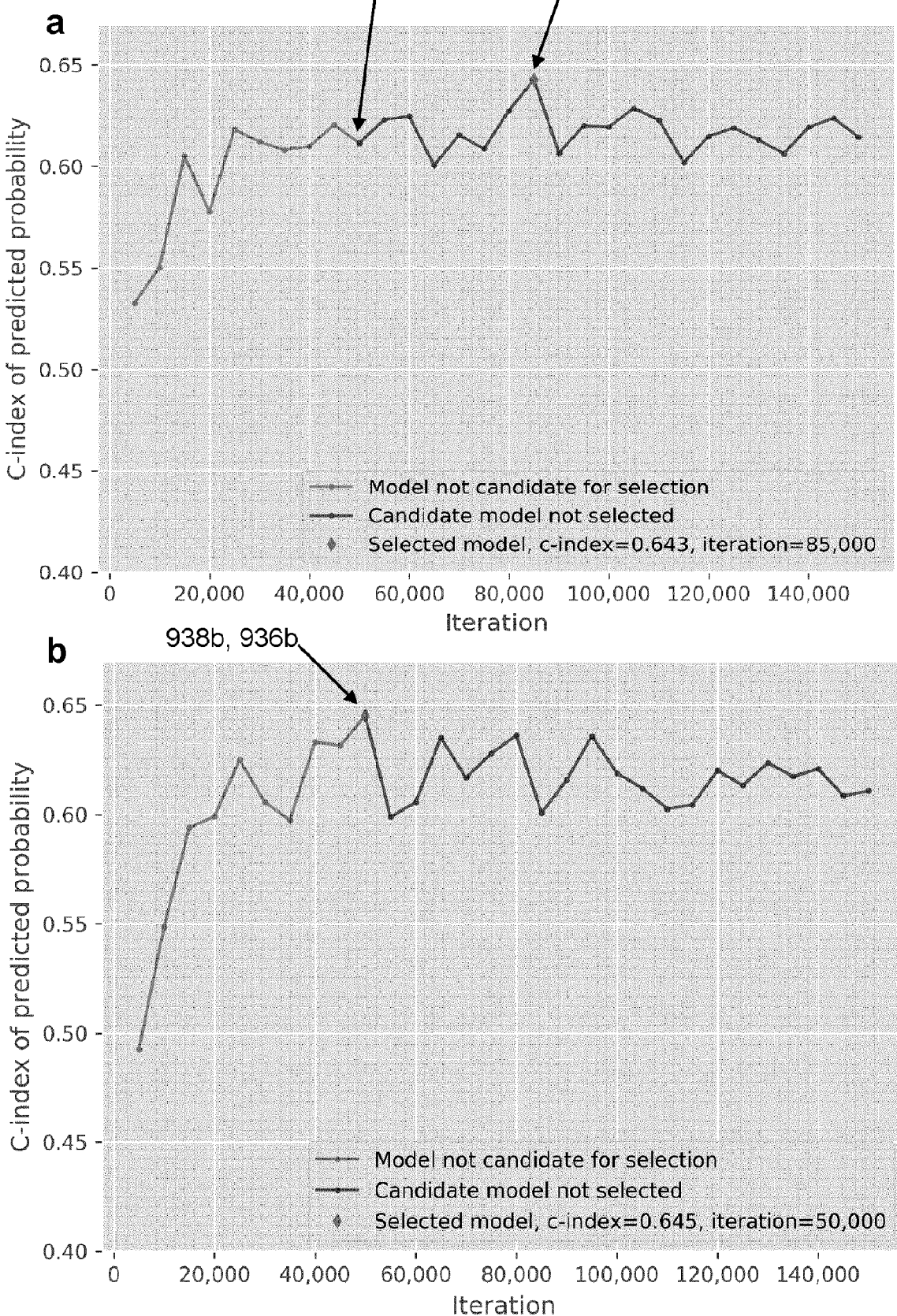
FIG. 9 shows the c-index of the 21 candidate 10× models of the Inception v3 network for patients with non-distinct prognosis in the training cohorts.
Figure 9:
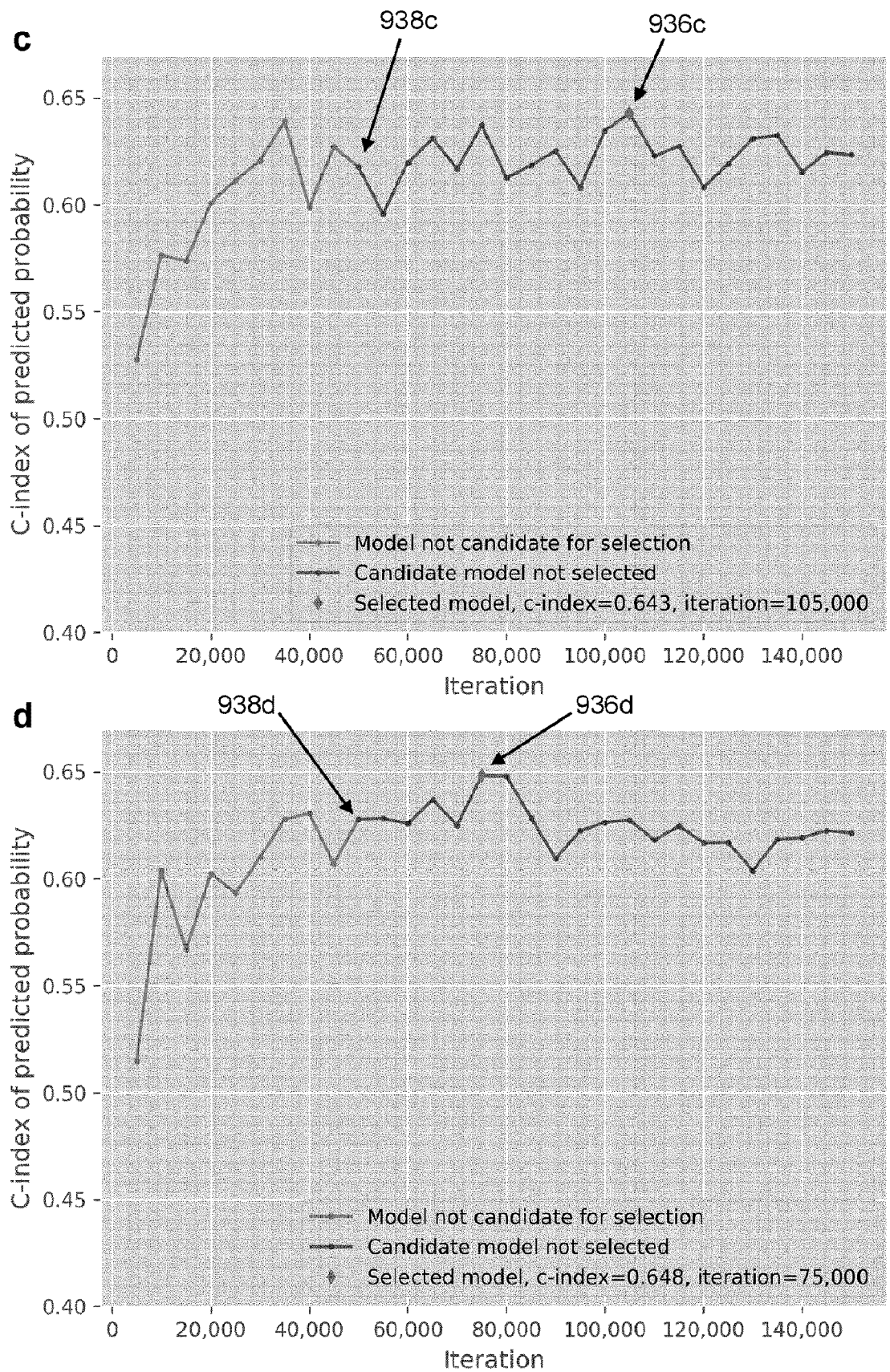
Figure 9:
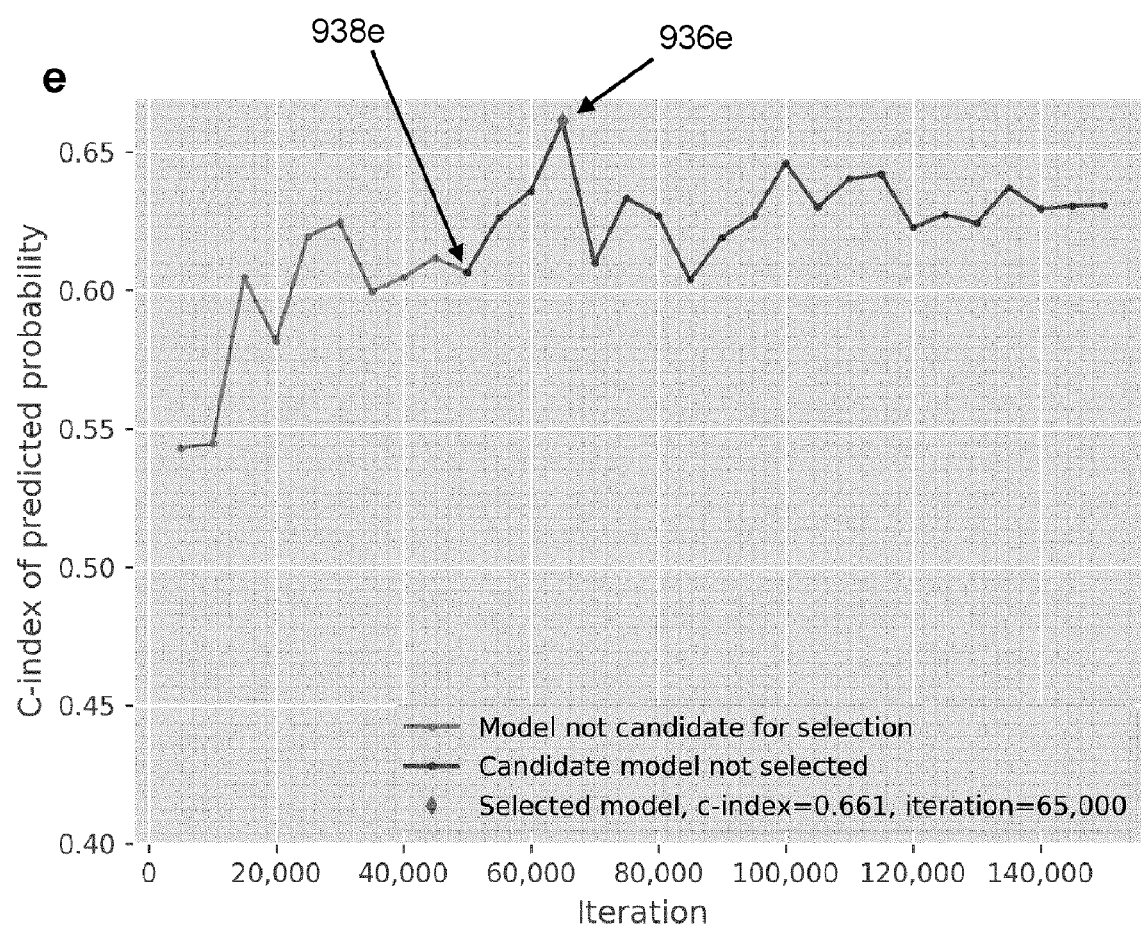

FIG. 9 shows the c-index of the 21 candidate 10× models of the Inception v3 network for patients with non-distinct prognosis in the training cohorts. Subplots a to e show training runs 1 to 5. The points referenced as 936*a-e* indicate the selected model. The points including and after the ones referenced 938*a-e* (apart from 936*a-e* of course) indicate models not selected. The c-index of nine models from the first third of each training run (the models before the ones referenced 938*a-e*) are shown for comparison.

Figure 10:
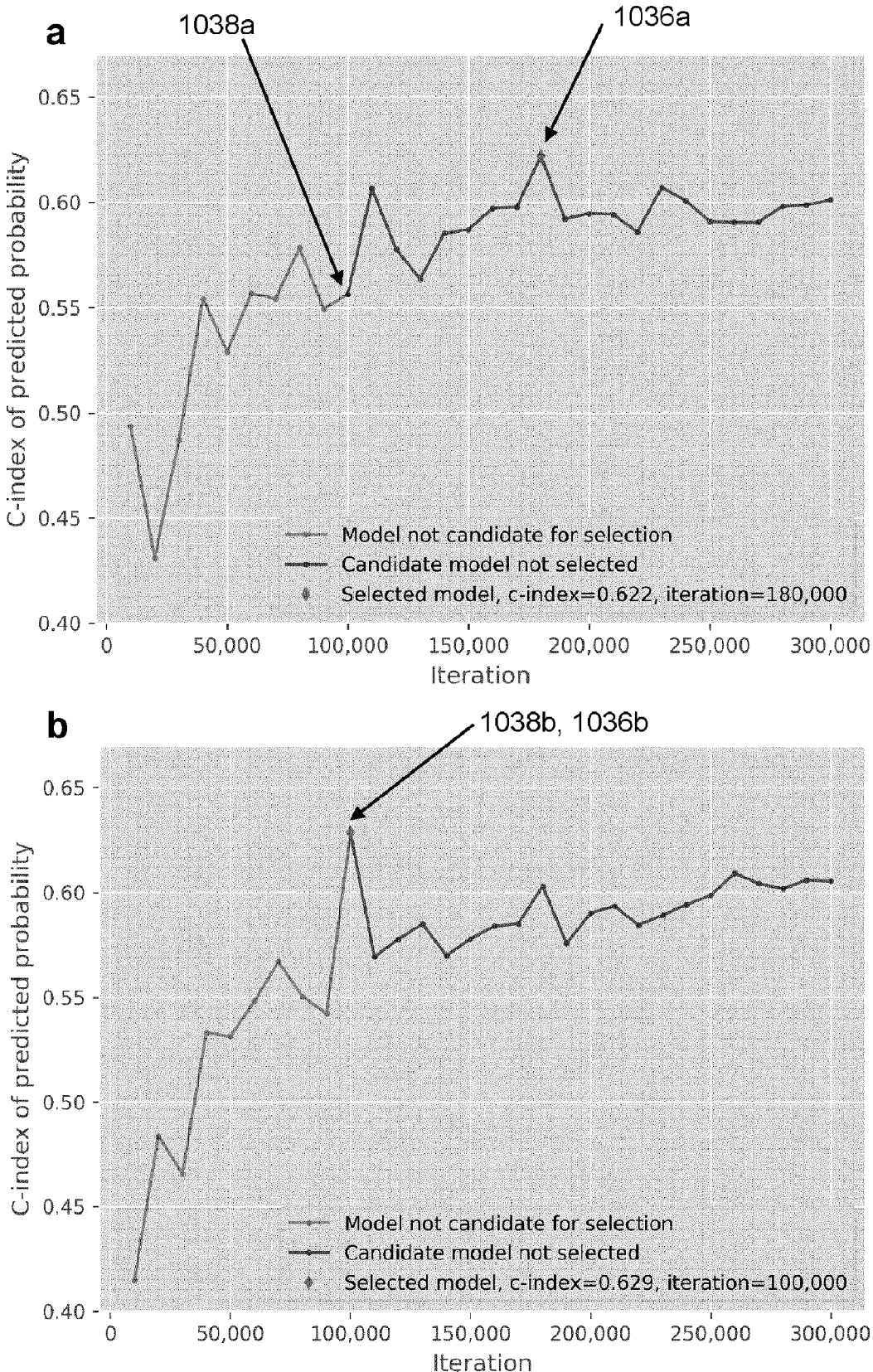
FIG. 10 shows the c-index of the 21 candidate 40× models of the Inception v3 network for patients with non-distinct prognosis in the training cohorts.
Figure 10:
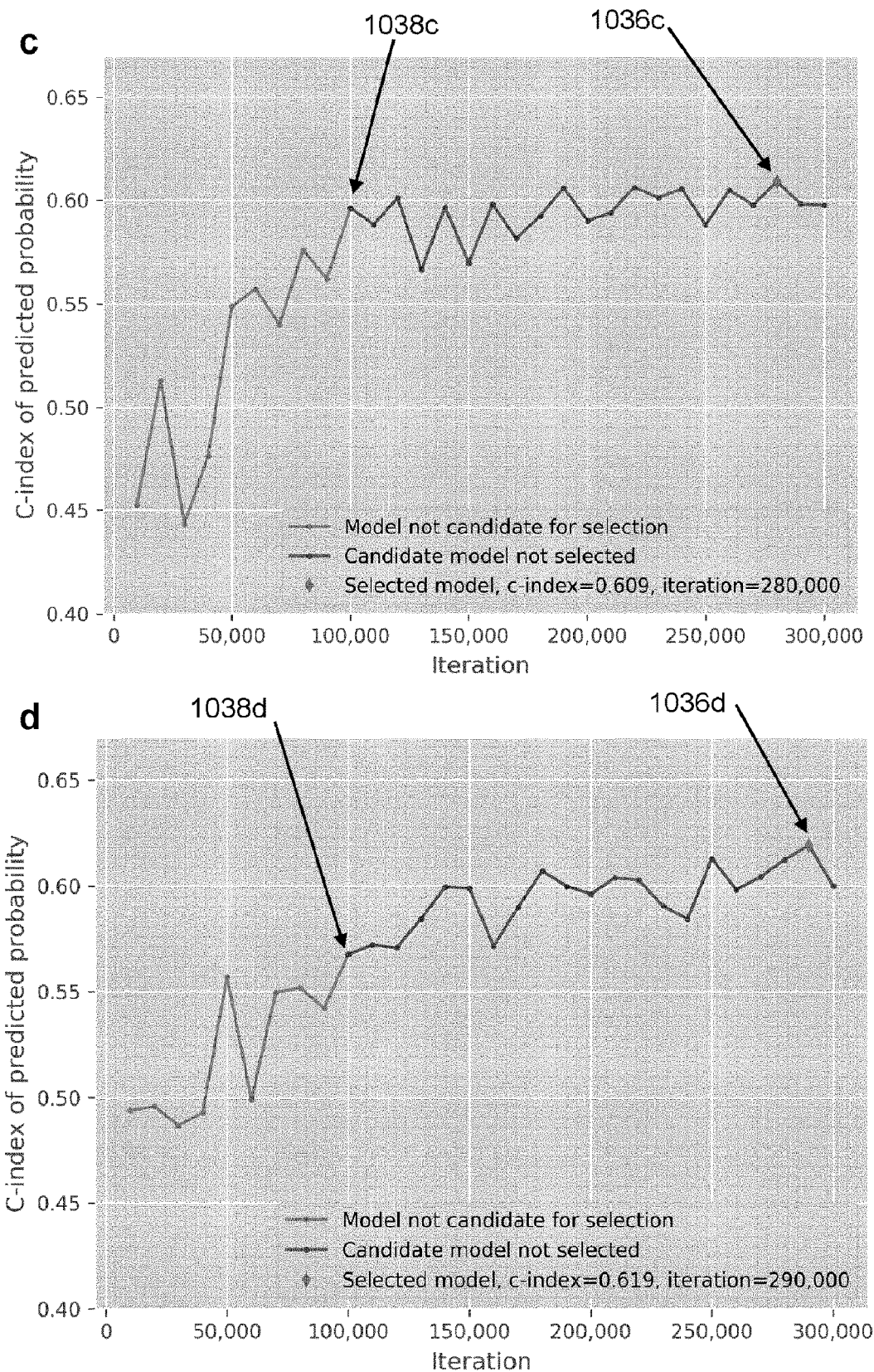
Figure 10:
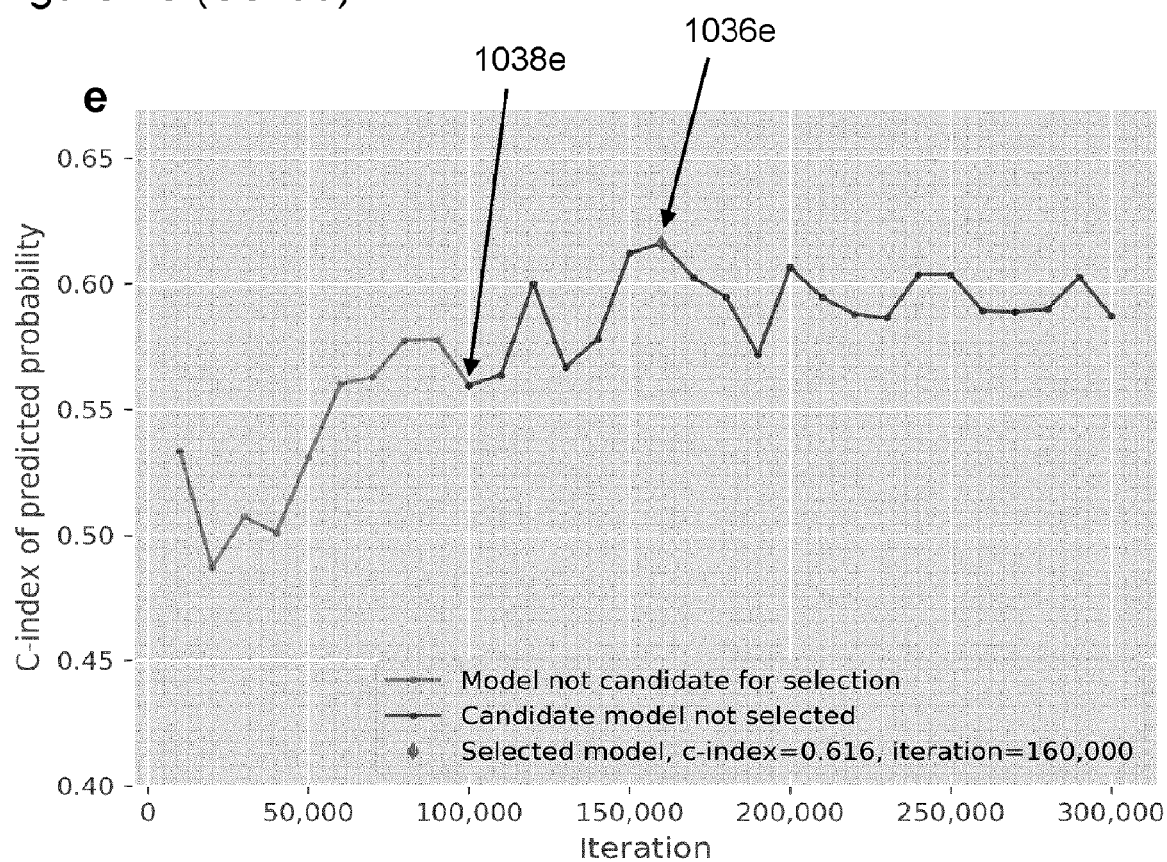

FIG. 10 shows the c-index of the 21 candidate 40× models of the Inception v3 network for patients with non-distinct prognosis in the training cohorts. Subplots a to e show training runs 1 to 5. The points referenced as 1036*a-e* indicate the selected model. The points including and after the ones referenced 1038*a-e* (apart from 1036*a-e* of course) indicate models not selected. The c-index of nine models from the first third of each training run (the models before the ones referenced 1038*a-e*) are shown for comparison.

1.3.6 Ensemble Models

An ensemble model was created for each network and resolution by averaging the five selected models' predicted probability of poor prognosis for a patient, resulting in four ensemble models; a 10× and a 40× ensemble model of the machine-learning-network 311 and similarly for the Inception v3 network.

With reference to FIG. 3, five instances of the machine-learning-network 311 are shown as Models 6-10. Each of these instances includes the first-neural-network 308 and the second-neural-network 316. Also, each of these instances is applied to the plurality of first-tiles 306 in order to determine five instances of the first-classifier 318 for the source-histological-image 302. In FIG. 3, the five instances of the first-classifier 318 have a respective value of 0.3142, 0.1930, 0.2533 and 0.2451. The classifier combiner 330 calculates a statistical representation of these five instances of the first-classifier 318, in this example the mean, to determine an averaged-first-classifier 340. In the example of FIG. 3 the averaged-first-classifier 340 has a value of 0.2468, and is referred to as a 10× ensemble prediction.

Similarly, five instances of the machine-learning-network 311 are shown as Models 1-5. Each of these instances includes the first-neural-network 308 and the second-neural-network 316. Also, each of these instances is applied to the plurality of second-tiles 307 in order to determine five instances of the second-classifier 319 for the source-histological-image 302. In FIG. 3, the five instances of the second-classifier 319 have a respective value of 02972, 0.3325, 0.3025, 0.5958 and 0.3112. The system 300 calculates a statistical representation of these five instances of the second-classifier 319, in this example the mean, to determine an averaged-second-classifier 341. In the example of FIG. 3 the averaged-second-classifier 341 has a value of 0.3678, and is referred to as a 40× ensemble prediction.

In this way, the classifier combiner 330 can apply a statistical function (such as an averaging function) to a plurality of classifiers in order to determine a combined-classifier (such as an averaged-classifier 340, 341).

In this example, the classifier combiner 330 applies a first thresholding function 342 to the averaged-first-classifier 340 in order to determine a thresholded-first-classifier. In this example, the first thresholding function 342 applies a single threshold to the averaged-first-classifier 340 such that the thresholded-first-classifier has a binary value. An example of how the single threshold can be set is described below. In FIG. 3 the thresholded-first-classifier can have a value of "predicted good" or "predicted bad". Therefore, this processing can be considered as dichotomising the ensemble model's predicted probability of poor prognosis. In other examples, the first thresholding function 342 can apply a plurality of thresholds to the averaged-first-classifier 340 such that the thresholded-first-classifier can take one of three or more discrete values.

Similarly, the classifier combiner 330 applies a second thresholding function 343 to the averaged-second-classifier 341 in order to determine a thresholded-second-classifier. In this example, as above, the second thresholding function 343 applies a single threshold to the averaged-second-classifier 341 such that the thresholded-second-classifier has a binary value. An example of how the single threshold can be set is described below. Again, the thresholded-second-classifier can have a value of "predicted good" or "predicted bad". Although in other examples, the second thresholding function 343 can apply a plurality of thresholds to the averaged-second-classifier 341 such that the thresholded-second-classifier can take one of three or more discrete values.

In this way, the classifier combiner 330 can apply a thresholding function (including one or more thresholds) to a classifier (optionally to an averaged-classifier) in order to determine a thresholded-classifier.

In this example, the thresholded-classifier that was determined was a prognostic indication for the patient from which the sample from which the assessed histological image was taken. It will be appreciated that an equivalent approach can be adopted to create ensemble models that determine a classifier (optionally, an averaged-classifier) in respect of any other outcome(s), the outcome(s) being dependent on the ground-truth(s) associated with the source-histological-images that are used during the training phase.

In one implementation, to determine a suitable threshold for dichotomising each ensemble model's predicted probability of poor prognosis, the c-index of the dichotomised ensemble model prediction is predicted for thresholds at 0.01, 0.02, and so on up to and including 0.99 for patients with non-distinct prognosis in the training cohorts. The threshold obtaining the maximum c-index can be selected for each ensemble model.

Figure 11:
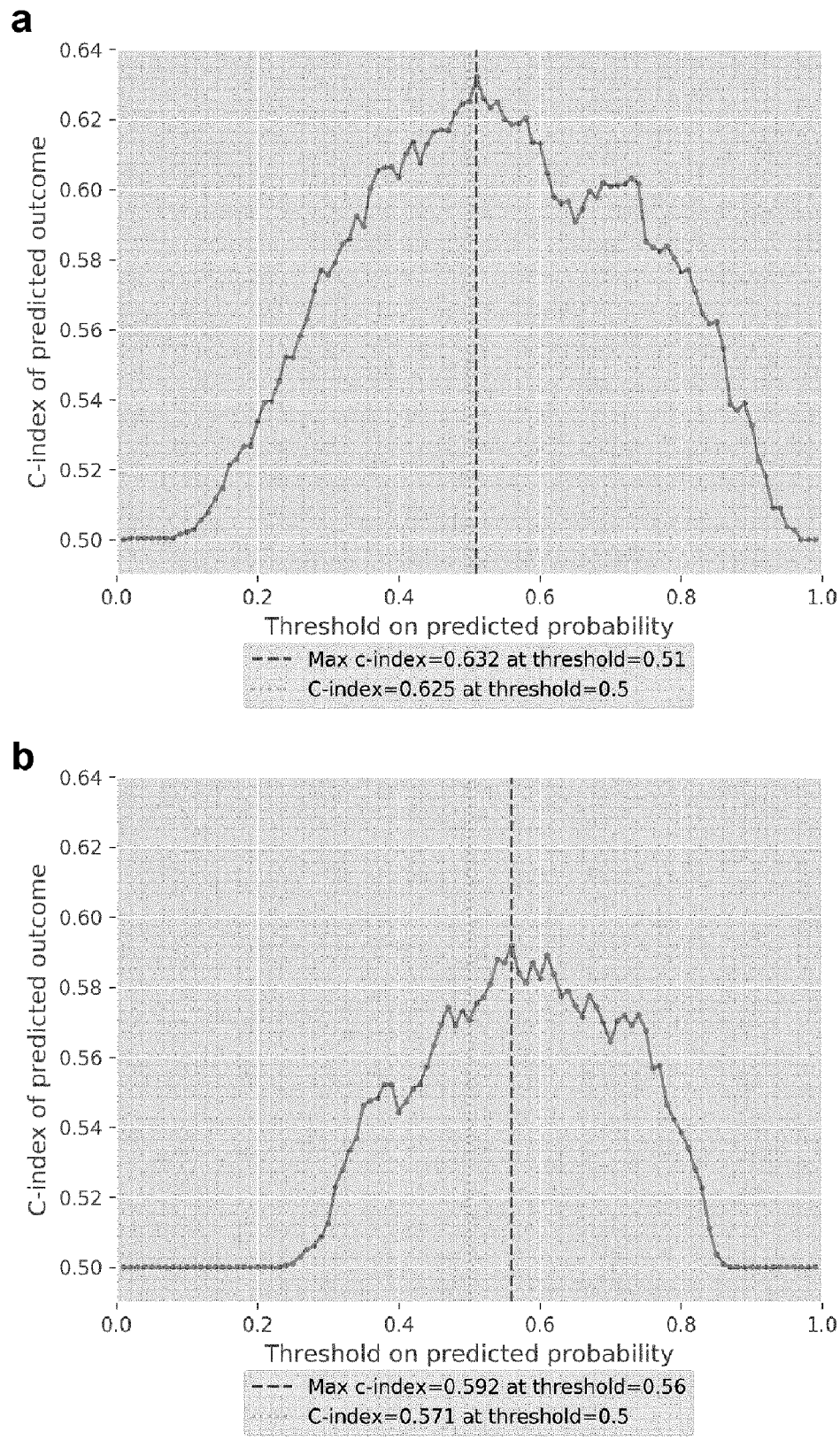
FIG. 11 shows the c-index of an ensemble model's predicted probability of poor prognosis thresholded at 0.01, 0.02, and so on up to and including 0.99 for patients with non-distinct prognosis in the training cohorts.
Figure 11:
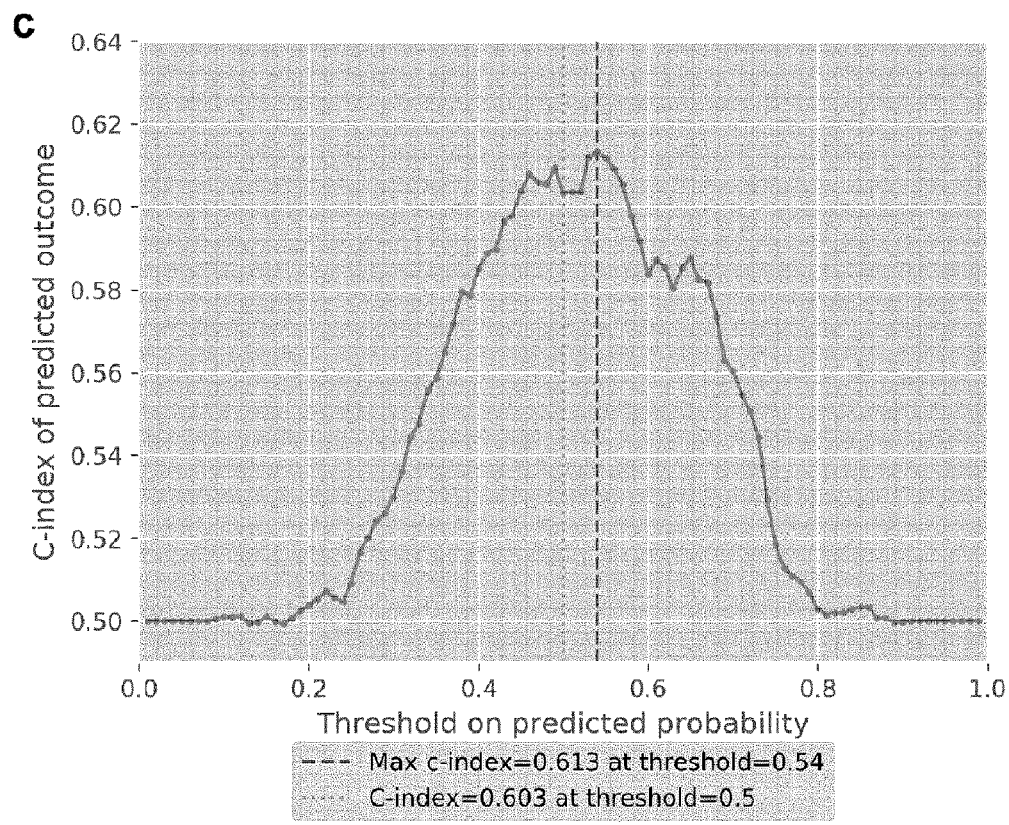
Figure 11:
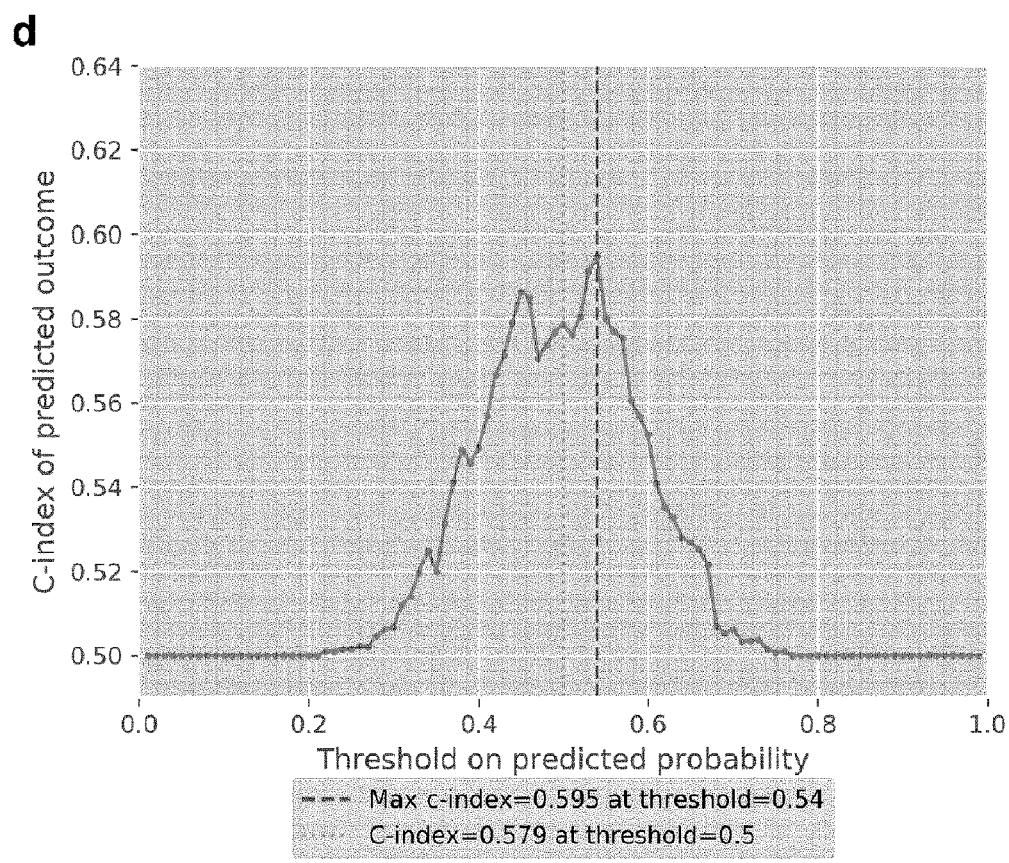

FIG. 11 shows the c-index of an ensemble model's predicted probability of poor prognosis thresholded at 0.01, 0.02, and so on up to and including 0.99 for patients with non-distinct prognosis in the training cohorts.

- Plot a shows the 10× ensemble model of the machine-learning-network 311 of FIG. 3. The predicted outcome is a poor prognosis if the ensemble model's predicted probability of poor prognosis is greater than 0.51. Otherwise, the predicted probability is less than or equal to 0.51 and the predicted outcome is good prognosis. This threshold (which may be referred to as a dichotomous marker) can be termed the 10× ensemble marker of the machine-learning-network 311.
- Plot b shows the 40× ensemble model of the machine-learning-network 311. The threshold identified by plot b, which may be referred to as the 40× ensemble marker of the machine-learning-network 311, is defined in this example as a threshold of 0.56.
- Plot c shows the 10× ensemble model of the Inception v3 network. The 10× ensemble marker of the Inception v3 network is defined as a threshold of 0.54.
- Plot d shows the 40× ensemble model of the Inception v3 network. The 40× ensemble marker of the Inception v3 network is also defined as a threshold of 0.54.

Returning to FIG. 3, the classifier combiner 330 then combines the thresholded-first-classifier and the thresholded-second-classifier to determine the overall-classifier 332 for the source-histological-image 202. In this example, the classifier combiner 330 performs a logical combination of the thresholded-first-classifier and the thresholded-second-classifier. If both the thresholded-first-classifier and the thresholded-second-classifier represent the same outcome, then the classifier combiner sets the overall-classifier 332 to the same value as the thresholded-first-classifier and the thresholded-second-classifier. If the thresholded-first-classifier and the thresholded-second-classifier represent different outcomes, then the classifier combiner sets the overall-classifier 332 to a value that is different to both the thresholded-first-classifier and the thresholded-second-classifier. As shown in FIG. 3:

- If the thresholded-first-classifier and the thresholded-second-classifier represent predicted good, then the classifier combiner 330 sets the overall-classifier 332 to "Agree good prognosis".
- If the thresholded-first-classifier and the thresholded-second-classifier represent predicted poor, then the classifier combiner 330 sets the overall-classifier 332 to "Agree poor prognosis".
- If one of the thresholded-first-classifier and the thresholded-second-classifier represents predicted good, and the other represents predicted poor, then the classifier combiner 330 sets the overall-classifier 332 to "disagree".

In this way, a combined 10× and 40× ensemble model can be created for the machine-learning-network 311 (and also for the Inception v3 network) by defining patients where the 10× and 40× ensemble markers predict the same outcome as either predicted good prognosis (if both ensemble markers predict good prognosis) or predicted poor prognosis (if both ensemble markers predict poor prognosis), and patients where the 10× and 40× ensemble markers predict different outcome as predicted uncertain prognosis. Optionally, if one of the ensemble markers could not be assayed for a patient, e.g. because there was no 10× tiles, then the combined 10× and 40× ensemble marker was not defined either. Thus such patients were excluded from analyses of the combined model.

This resulted in two combined 10× and 40× ensemble markers, one for the machine-learning-network 311 and one for the Inception v3 network. These 3-grouped variables can be referred to as the DoMore v1 marker and the Inception v3 marker.

The computer systems disclosed herein may comprise a computer-readable storage medium, a memory, a processor and one or more interfaces, which are all linked together over one or more communication busses. The exemplary computer system may take the form of a conventional computer system, such as, for example, a desktop computer, a personal computer, a laptop, a tablet, a smart phone, a smart watch, a virtual reality headset, a server, a mainframe computer, and so on. In some embodiments, it may be embedded in a microscopy apparatus, such as a virtual slide microscope capable of whole slide imaging.

The computer-readable storage medium and/or the memory may store one or more computer programs (or software or code) and/or data. The computer programs stored in the computer-readable storage medium may include an operating system for the processor to execute in order for the computer system to function. The computer programs stored in the computer-readable storage medium and/or the memory may include computer programs according to embodiments of the invention or computer programs that, when executed by the processor, cause the processor to carry out a method according to an embodiment of the invention The processor may be any data processing unit suitable for executing one or more computer readable program instructions, such as those belonging to computer programs stored in the computer-readable storage medium and/or the memory. As part of the execution of one or more computer-readable program instructions, the processor may store data to and/or read data from the computer-readable storage medium and/or the memory. The processor may comprise a single data processing unit or multiple data processing units operating in parallel or in cooperation with each other. In a particularly preferred embodiment, the processor may comprise one or more Graphics Processing Units (GPUs). GPUs are well suited to the kinds of calculations involved in training and using machine-learning algorithms such as those disclosed herein. The processor may, as part of the execution of one or more computer readable program instructions, store data to and/or read data from the computer-readable storage medium and/or the memory.

The one or more interfaces may comprise a network interface enabling the computer system to communicate with other computer systems across a network. The network may be any kind of network suitable for transmitting or communicating data from one computer system to another. For example, the network could comprise one or more of a local area network, a wide area network, a metropolitan area network, the internet, a wireless communications network, and so on. The computer system may communicate with other computer systems over the network via any suitable communication mechanism/protocol. The processor may communicate with the network interface via the one or more communication busses to cause the network interface to send data and/or commands to another computer system over the network. Similarly, the one or more communication busses enable the processor to operate on data and/or commands received by the computer system via the network interface from other computer systems over the network.

The interface may alternatively or additionally comprise a user input interface and/or a user output interface. The user input interface may be arranged to receive input from a user, or operator, of the system. The user may provide this input via one or more user input devices (not shown), such as a mouse (or other pointing device, track-ball or keyboard. The user output interface may be arranged to provide a graphical/visual output to a user or operator of the system on a display (or monitor or screen) (not shown). The processor may instruct the user output interface to form an image/video signal which causes the display to show a desired graphical output. The display may be touch-sensitive enabling the user to provide an input by touching or pressing the display.

According to embodiments of the invention, the interface may alternatively or additionally comprise an interface to a digital microscope or other microscopy system. For example, the interface may comprise an interface to a virtual microscopy apparatus capable of Whole Slide Imaging (WSI). In WSI, a virtual slide is generated by high-resolution scanning of a glass slide by a slide scanner. The scanning is typically done piecewise and the resulting images are stitched together to form one very large image at the highest magnification of which the scanner is capable. These images may have dimensions of the order of 100,000×200,000 pixels—in other words, they may contain several billion pixels. According to some embodiments, the computer system may control the microscopy apparatus through the interface to scan slides containing specimens. The computer system may thus obtain microscopic images of histological specimens from the microscopy apparatus, received through the interface.

It will be appreciated that the architecture of the computer system described above is merely exemplary and that systems having different architectures using alternative components or using more components (or fewer) may be used instead.

2. Histological Images, and Sources Thereof

The term "histological image" as used herein refers to an image of a histological specimen, showing the microscopic structure of biological material. A "source-histological-image" is a histological image of a histological specimen that has been obtained from a defined source of biological material. The defined source of biological material may, for example, be an ex vivo sample of biological material. The histological image may be used in accordance with the present invention, for example, for the purposes of training or for the purposes of inference, as described further in the present application.

A histological image may be obtained, for example, by light microscopy of a histological specimen, for example, at a level of magnification that is equivalent to low-powered, or high-powered, magnification as discussed in more detailed in section 1.2 of this application. However, the skilled person will appreciate that other means of imaging a histological specimen, including other forms of microscopy, may be used to generate a histological image.

A histological image may also be conveniently generated, for example, by generating a whole slide image (WSI) by techniques such as those conventional in the art, for example, as discussed in Farahani et al., *Pathology and Laboratory Medicine International*, 2015, 7: 23-33, the contents of which are incorporated herein by reference. WSI, also commonly referred to as "virtual microscopy", typically aims to emulate conventional light microscopy in a computer-generated manner. Practically speaking, WSI typically includes two processes. The first process typically utilizes specialised hardware (scanner) to digitize an image of the histological specimen (which is usually provided on a glass slide), which generates a large representative digital image (so-called "digital slide"). The second process typically employs specialized software (e.g. a so-called virtual slide viewer) to view and/or analyse the resultant enormous digital files. As discussed in Farahani et al. 2015 (supra), during the last decade, a wide range of commercially available WSI instruments have been developed. A list of common WSI systems and their respective vendors include, without limitation, 3DHistech (Pannoramic SCAN II, 250 Flash); DigiPath (PathScope); Hamamatsu (NanoZoomer RS, HT, and XR); Huron (TISSUEscope 4000, 4000XT, HS); Leica, formerly known and operated as Aperio (ScanScope AT, AT2, CS, FL, SCN400); Mikroscan (D2); Olympus (V S120-SL); Omnyx (VL4, VL120); PerkinElmer (Lamina); Philips (Ultra-Fast Scanner); Sakura Finetek (VisionTek); Unic (Precice 500, Precice 600x); Ventana, formerly known and operated as Bioimagene (iScan Coreo, iScan HT); and Zeiss (Axio Scan.Z1). These devices are meant to meet the needs of a diverse user base. A list of differences between selected WSI systems is provided in Table 2 of Farahani et al. 2015 (supra). Preferred devices include those used in the present examples, which includes the NanoZoomer XR scanner and/or the Apiero AT2 scanner.

Accordingly, in a preferred embodiment, the or each source-histological-image may be a WSI.

In a preferred embodiment, the methods of the present invention, in particular the training methods, include obtaining the plurality of source-histological-images, such as WSIs, of histological specimens that have been stained with a marker using at least two different pieces of image scanning equipment. By avoiding the use of a single piece of image scanning equipment, the trained machine-learning algorithm is not trained to use only the images from that single piece of image scanning equipment, and accordingly the trained machine-learning algorithm should be more capable of processing images from different pieces of image scanning equipment. Introducing more scanners in training can advantageously improve the generalisation for subsequent inference.

In the case that different pieces of image scanning equipment are used, the methods of the present invention may further include a step of aligning the images. This may be done by a scale-invariant feature transform, generally referred to as a SIFT transform, for example.

Each microscopic image is preferably a grayscale or colour image consisting of one, two or three colour channels. Most preferably, it is a colour image consisting of three colour channels. Thus, it provides three samples for each pixel. The samples are coordinates in a three-dimensional colour space. Suitable 3-D colour spaces include but are not limited to RGB, HSV, YCbCr, and YUV.

A "histological feature of interest" within a histological image refers to a feature of the microscopic structure present in a histological image, such as a WSI. Without limitation, the feature may be of interest, for example, for diagnostic or therapeutic purposes, or for scientific research.

Histological specimens are commonly used to review the structure to determine a diagnosis or to determine a prognosis in respect of a subject from which the histological specimen was taken.

Histological specimens may be obtained from any biological source. They may be, for example, from any organism, from any tissue, organ or other structure within an organism, and from healthy and/or pathological samples. Sources of particular interest are discussed further below.

As discussed in more detail in section 1 of the present application, and as further defined by the present claims, the present application describes a computer implemented system (100; 200; 300) for determining a classifier (118; 318), or an overall-classifier (232; 332), for a source-histological-image (102; 202; 302), which may be a source-histopathological-image.

In the training phase, the source-histological-images (e.g. WSIs) used are images of histological specimens obtained from a source for which a ground-truth is known. Each of the source-histological-images are then paired up with the associated truth-data representing the ground-truth for each source from which each histological specimen was obtained. In the examples described herein, the histological specimens were obtained from cancer patients, and the ground-truth related to the categorisation of each patient into a prognostic group, as further described herein.

In the case of using a computer implemented system (100; 200; 300) that has already been trained, through the training phase, then a source-histological-image (e.g. a WSI) may be an image of a histological specimen obtained from a source for which a ground-truth is not known. The unknown ground-truth may for example, and without limitation, be diagnostic or prognostic information related to the source (such as a subject) from which histological specimen was obtained. The computer implemented system (100; 200; 300) may then be used to determine a classifier (118;318), or an overall-classifier (232; 332), for the source-histological-image (102; 202; 302) in relation to the unknown ground-truth, by way of making, for example, a diagnostic or prognostic assessment of the source from which the source-histological-image was obtained.

2.1 Organisms

The biological source of a histological specimen, from which a source-histological-image (102; 202; 302) is obtained may, for example, be from any organism, preferably a cellular organism, and more preferably a multi-cellular organism. The biological source may be, for example, an animal, for example either a human or non-human animal, such as a primate, non-human primate, laboratory animal, farm animal, livestock, or a domestic pet.

It may be most preferred that the biological source is a human subject.

Exemplary non-human animals can optionally include poultry (such as a chicken, turkey, geese, quail or ducks), livestock (such as cattle, sheep, goats or swine, alpaca, banteng, bison, camel, cat, deer, dog, donkey, gayal, guinea pig, horse, llama, mule, rabbit, reindeer, water buffalo, yak), and other animals, including zoo animals, captive animals, game animals, fish (include freshwater and saltwater fish, farmed fish, and ornamental fish), other marine and aquatic animals (including shellfish such as, but not limited to, oysters, mussels, clams, shrimps, prawns, lobsters, crayfish, crabs, cuttlefish, octopus, and squid), domestic animals (such as cats and dogs), rodents (such as mice, rats, guinea pigs, hamsters), and horses, are also included, as well as any other domestic, wild and farmed animal, including mammals, marine animals, amphibians, birds, reptiles, insects and other invertebrates.

In an alternative embodiment, the organism used for the biological source may comprise biological material obtained from a non-animal source, such as from a plant, a fungus, or a monera (e.g. bacteria or archae).

2.2 Tissues, Organs and Other Structure

A biological source may be from any tissue type, organ or other structure of interest from a selected organism, such as from a human subject or any other multi-cellular organism as discussed above in section 2.1 of this application.

For example, the biological source may be from a tissue present within a human or non-human animal; including for example and one or more of the epithelia, connective tissue, muscle, and/or the nervous system of the selected organism. It may be particularly preferred that the biological source may be from a tissue present within a human subject.

Accordingly, the biological source may be from, or include, tissue present within the epithelia of the selected organism, such as from a human subject.

Epithelia are continuous sheets of cells (one or more layers thick) that cover the exterior surfaces of the body, line internal closed cavities and body tubes that communicate with the outside environment (the alimentary, respiratory and genitourinary tracts), make up the secretory portions of glands and their ducts, and are found in the sensory receptive regions of certain sensory organs (e.g. ear & nose). Epithelia cover and line surfaces (e.g. skin), are involved in absorption (e.g. the intestine), secretion (e.g. glands), can be sensory (e.g. neuroepithelium) or contractile (e.g. myoepithelial cells). Epithelia are typically a continuous sheet of cells covering the surfaces of the body. There are two major types of epithelia: covering epithelia and glandular epithelia.

Covering epithelia can include squamous epithelia (e.g. the endothelial lining of blood vessels and the mesothelial lining of the body cavities), cuboidal epithelia (e.g. tissues that line small ducts and/or tubules, such as in the salivary glands or kidneys), columnar epithelia (such as cells which line the stomach, uterine cervix and/or intestine), pseudostratified epithelium, stratified epithelia (such as keratinising (i.e. the skin) or non-keratinising (i.e. the oesophagus) forms of stratified epithelia).

Glandular epithelia are present in glands which are an organised collection of secretory epithelial cells. Most glands are formed during development by proliferation of epithelial cells so that they project into the underlying connective tissue. Some glands retain their continuity with the surface via a duct and are known as exocrine glands. Other glands lose this direct continuity with the surface when their ducts degenerate during development. These glands are known as endocrine glands.

Accordingly, the biological source for a source-histological-image for use in the present invention may consist, consist essentially of, or comprise any one or more, of the foregoing types of epithelia, or any other type of epithelium of interest.

Additionally and/or alternatively, the biological source for a source-histological-image may be from, or include, a tissue present within the connective tissue of the selected organism, such as from a human subject. Connective tissue is made up of cells and extracellular matrix. The extracellular matrix is made up of fibres in a protein and polysaccharide matrix, secreted and organised by cells in the extracellular matrix. Variations in the composition of the extracellular matrix, determines the properties of the connective tissue. For example, if the matrix is calcified, it can form bone or teeth. Specialised forms of extracellular matrix also makes up tendons, cartilage, and the cornea of the eye. General connective tissue is either loose, or dense, depending on the arrangement of the fibres. The cells sit in a matrix made up of glycoproteins, fibrous proteins and glycosoaminoglycans, which have been secreted by the fibroblasts, and the major component of the matrix, is in fact, water.

Connective tissue may, for example, be a form of connective tissue proper (for example loose irregular connective tissue and/or dense irregular connective tissue), or a form of specialised connective tissue. Examples of specialised connective tissue include: dense regular connective tissue which is found in tendons and ligaments; cartilage; adipose tissue; haemopoietic tissue (such as bone marrow, lymphoid tissue); blood; and bone.

Accordingly, the biological source for a source-histological-image for use in the present invention may consist, consist essentially of, or comprise any one or more, of the foregoing types of connective tissues, or any other type of connective tissue of interest.

Additionally and/or alternatively, the biological source for a source-histological-image may be from, or include, a tissue present within the muscle of the selected organism, such as from a human subject. The muscle tissue may be either striated or smooth. The muscle tissue may be a form of skeletal muscle or cardiac muscle (both of which are types of striated), or may be a type of smooth muscle (such as muscle tissue found in the walls of most blood vessels and tubular organs such as the intestine).

Accordingly, the biological source for a source-histological-image for use in the present invention may consist, consist essentially of, or comprise any one or more, of the foregoing types of muscle tissues, or any other type of muscle tissue of interest.

Additionally, and/or alternatively, the biological source for a source-histological-image may be from, or include, a tissue present within the nervous system of the selected organism, such as from a human subject. The nervous system includes the central nervous system (CNS), which is composed of the brain and spinal cord; and the peripheral nervous system (PNS), which is composed of all the nervous tissue outside the CNS, including cranial nerves from the brain, spinal nerves from the spinal cord, and nodules known as ganglia, that contain the neuronal cell bodies.

Accordingly, the biological source for a source-histological-image for use in the present invention may consist, consist essentially of, or comprise any one or more, of the foregoing types of nervous system, or any other type of tissue of interest within the nervous system.

Optionally, the biological source for a source-histological-image for use in the present invention may consist, consist essentially of, or comprise biological material obtained from any one or more, of the following organs of the selected organism, such as from a human subject:

The muscular system, such as from the skeleton, joints, ligaments, muscular system and/or tendons.

The digestive system, such as from the mouth (e.g. teeth and/or tongue), the salivary glands (e.g. the parotid glands, the submandibular glands and/or the sublingual glands), the pharynx, the esophagus, the stomach, the small intestine (e.g. the duodenum, the jejunum and/or the ileum) the large intestine, the liver, the gallbladder, the mesentery, the pancreas, the anal canal and/or anus.

The respiratory system, such as from the nasal cavity, the pharynx, the larynx, the trachea, the bronchi, the lungs and/or the diaphragm.

The urinary system, such as from the kidneys, the ureter, the bladder and/or the urethra.

The reproductive organs, such as the female or male reproductive organs. The female reproductive system includes the internal reproductive organs (such as the ovaries, the fallopian tubes, the uterus and the vagina), the external reproductive organs (such as the vulva and the clitoris), and the placenta. The male reproductive system includes the internal reproductive organs (such as the testes, the epididymis, the vas deferens, the seminal vesicles, the prostate, the bulbourethral glands) and the external reproductive organs (such as the penis and the scrotum).

The endocrine system, such as the pituitary gland, the pineal gland, the thyroid gland, the parathyroid glands, the adrenal glands and the pancreas.

The circulatory system, such as the heart, the patent foramen ovale, the arteries, the veins and the capillaries.

The lymphatic system, such as the lymphatic vessel, lymph nodes, bone marrow, the thymus, the spleen, the gut-associated lymphoid tissue, including the tonsils.

The nervous system, such as the brain (including the cerebrum (e.g. cerebral hemispheres) and the diencephalon), the brainstem (including the midbrain, the pons and the medulla oblongata), the cerebellum, the spinal cord and the ventricular system, including the choroid plexus. The peripheral nervous system, such as the nerves (e.g. cranial nerves, spinal nerves, ganglia and enteric nervous system).

Sensory organs, such as the eye and components thereof (e.g. cornea, iris, ciliary body, lens and/or retina), the ear or components thereof (e.g. the outer ear, such as the earlobe; the eardrum; the middle ear, such as the ossicles; the inner ear, such as the cochlea, the vestibule of the ear and/or the semicircular canals), the olfactory epithelium, and the tongue (including taste buds).

The integumentary system, such as the mammary glands, the skin and/or the subcutaneous tissue.

2.3 Healthy or Pathological Samples

Histological specimens may be obtained from healthy or pathological samples.

The biological source for a source-histological-image for use in the present invention may consist, consist essentially of, or comprise, biological material obtained from healthy or pathological samples.

In the case that biological material is obtained from a pathological sample, then the histological specimen obtained therefrom may be referred to as "histopathological" sample, and an image obtained from histopathological sample of defined source may be referred to as a "source-histopathological-image". The term "pathological" as used herein, refers to an unhealthy state, including any medical condition, disorder or disease.

Such histopathological samples may contain, or be suspected of containing, biological material comprising the pathological condition. For example, the biological source for a histopathological sample may be a subject, such as a human subject, that has a pathological condition, has been diagnosed as having a pathological condition, is suspected of having a pathological condition, is being treated for a pathological condition, has previously been treated for a pathological condition, and/or has previously had a pathological condition.

For example, in the instance that the pathological condition is cancer, and the biological source is a subject, such as a human subject, that has, has been diagnosed as having, is suspected of having, is being treated for, has been treated for, and/or has previously had cancer, then the histopathological samples may contain, or be suspected of containing, biological material comprising cancerous cells.

A source-histopathological-image obtained from histopathological sample may be confirmed to contain an image comprising biological material that: (a) comprises, consists essentially of, or consists of biological material having the pathological condition and/or (b) comprises, consists essentially of, or consists of biological material that has been modified by the pathological condition.

This confirmatory step may be performed in any number of ways. The skilled person is aware of many different approaches for confirming the presence of a pathological condition in a biological material, in a histological sample obtained from the biological material and/or in a histological image obtained therefrom. For example, and without limitation, the confirmatory step may be performed by a human assessment (e.g. by a trained pathologist). As exemplified herein, and without limitation, in the context of a source-histopathological-image obtained from human subjects with cancer, a pathologist was used to ascertain whether there was tumour in each tissue section, although it will be appreciated that an equivalent computer-implemented assessment for the presence of tumour material in a tissue sample could also be used.

Accordingly, it may be preferred that the histological specimens comprise biological material obtained from subjects having, or suspected of having, a medical condition.

The medical condition may, for example, be a disease. More particularly, the disease may be a disease selected from the group consisting of: infectious diseases, deficiency diseases, hereditary diseases (including both genetic diseases and non-genetic hereditary diseases), and physiological diseases.

The disease may be a communicable disease. Alternatively, the disease may be a non-communicable disease.

The disease may be optionally present in one or more tissue and/or organ or other body part as described above in section 2.2 of this application.

Without limitation, exemplary diseases include: diseases of genetic origin, diseases arising from chemical and/or physical injury, diseases of immune origin (including immune deficiencies, and immune responses in the absence of infection), diseases of biotic origin (including, for example, viral diseases, rickettsial diseases, bacterial diseases, and diseases caused by fungi and other parasites), diseases associated with the abnormal growth of cells (including without limitation, hyperplasia, benign tumours and malignant tumours) in particular cancer, diseases of metabolic-endocrine origin, diseases of nutrition (e.g. including diseases of nutritional excess and/or diseases of nutritional deficiency, diseases of neuropsychiatric origin (including for example, neurological disorders such as Alzheimer's disease, Huntington's chorea, and Parkinson's disease), and diseases of senescence.

The disease may, optionally, be acute, chronic, malignant, or benign. An acute disease process usually begins abruptly and is over soon. Chronic diseases often begin very gradually and then persists over a long period. The terms benign and malignant, most often used to describe tumours, can be used in a more general sense. Benign diseases are generally without complications, and a good prognosis (outcome) is usual. Malignancy implies a process that, if left alone, will result in fatal illness. Cancer is the general term for all malignant tumours.

2.3.1 Cancer:

In one embodiment of particular interest for the present invention, the biological source for a source-histological-image for use in the present invention may consist, consist essentially of, or comprise, biological material obtained from a subject, such as a human subject, that has, has been diagnosed as having, is suspected of having, is being treated for, has been treated for, and/or has previously had cancer.

The biological material may be obtained from the site of a primary, secondary or any other tumour in the body of the subject, or be obtained from a site that is local to, regional to, or distal to the site of any such known tumour.

The histopathological samples may contain, or be suspected of containing, biological material comprising one or more cancerous cells.

A source-histopathological-image obtained from histopathological sample may, prior to its use in the present invention, be confirmed to contain an image of biological material comprising one or more cancerous cells.

Any type of cancer can be assessed with the present invention.

Tumors are often assigned a grade and a stage. The stage of a solid tumor refers to its size or extent and whether or not it has spread to other organs and tissues. The grade of a tumor—the cancer grade—is an indication of how quickly it is likely to grow and spread.

For example, the cancer may be stage 0, stage I, stage II, stage III or stage IV, or a subdivision of any one or more thereof. The characteristics of these different stages and the subdivisions thereof are well known in the art. However, in general terms: Stage 0 indicates that the cancer is where it started (in situ) and has not spread. Stage I indicates that the cancer is small and has not spread anywhere else. Stage II indicates that the cancer has grown, but has not spread. Stage III indicates that the cancer is larger and may have spread to the surrounding tissues and/or the lymph nodes (part of the lymphatic system). Stage IV indicates that the cancer has spread from where it started to at least one other body organ, also known as "secondary" or "metastatic" cancer.

In one embodiment, the cancer may be a stage of cancer classified by the TNM Staging System. This is system that was developed and is maintained by the AJCC and the Union for International Cancer Control (UICC). It is the most commonly used staging system by medical professionals around the world. The TNM classification system was developed as a tool for doctors to stage different types of cancer based on certain, standardized criteria. The TNM Staging System is based on the extent of the tumor (T), the extent of spread to the lymph nodes (N), and the presence of metastasis (M).

- The T category describes the original (primary) tumor. TX refers to a primary tumor that cannot be evaluated. T0 refers to no evidence of a primary tumor. Tis refers to a carcinoma in situ (early cancer that has not spread to neighboring tissue). T1, T2, T3 and T4 relate to the size and/or extent of the primary tumor.
- The N category describes whether or not the cancer has reached nearby lymph nodes. NX indicates that regional lymph nodes cannot be evaluated. N0 indicates no regional lymph node involvement (no cancer found in the lymph nodes). N1, N2 and N3 indicate involvement of regional lymph nodes (number and/or extent of spread).
- The M category tells whether there are distant metastases (spread of cancer to other parts of the body). M0 indicates no distant metastasis (cancer has not spread to other parts of the body). M1 indicates distant metastasis (cancer has spread to distant parts of the body).

Because each cancer type has its own classification system, letters and numbers do not always mean the same thing for every kind of cancer. Once the T, N, and M are determined, they are combined, and an overall stage of 0, I, II, III, IV can be assigned. Sometimes these stages are subdivided as well, using letters such as IIIA and IIIB. Further guidance can be at www. https://cancerstaging/org.

In some cancer types, non-anatomic factors can be taken into account for assigning the anatomic stage/prognostic group. These are clearly defined in each chapter of the AJCC Cancer Staging Manual (e.g. Gleason Score in Prostate). These factors are collected separately from T, N, and M, which remain purely anatomic and are used to assign stage groups. Where non-anatomic factors are used in groupings, there is a definition of the groupings provided for cases where the non-anatomic factor is not available (X) or where it is desired to assign a group ignoring the non-anatomic factor.

Stage I cancers are the least advanced and often have a better prognosis. Higher stage cancers are often more advanced but in many cases can still be treated successfully.

In an additional and/or alternative option, the cancer may be of a specified grade. Grading is typically based on the differentiation of cells (degree of resemblance to normal cells). The specified grade of the cancer may, for example, be grade I, grade II, grade III or grade IV cancer, or a combination of two or three categories. The characteristics of these different grades are well known in the art. However, in general terms: A grade I cancer is a type of cancer in which the cells that resemble normal cells and are not growing rapidly; a grade II cancer is a type of cancer in which the cancer cells do not look like normal cells and are growing faster than normal cells; and grades III and IV are a type of cancer in which cancer cells look abnormal and may grow or spread more aggressively. Growth characteristics may, for example, be assessed in some cancers based on frequency of dividing cells.

The cancer may, for example, be a type of cancer that is selected from the group consisting of carcinoma, sarcoma, myeloma, leukemia, lymphoma and a mixed type of cancer.

Carcinoma refers to a malignant neoplasm of epithelial origin or cancer of the internal or external lining of the body. Carcinomas, malignancies of epithelial tissue, account for 80 to 90 percent of all cancer cases. Epithelial tissue is found throughout the body. It is present in the skin, as well as the covering and lining of organs and internal passageways, such as the gastrointestinal tract, as further discussed above.

Carcinomas may be divided into two major subtypes: adenocarcinoma, which develops in a glandular organ, and squamous cell carcinoma, which originates in the squamous epithelium.

Adenocarcinomas generally occur in mucus membranes and are first seen as a thickened plaque-like white mucosa. They often spread easily through the soft tissue where they occur. Squamous cell carcinomas occur in many areas of the body.

Most carcinomas affect organs or glands capable of secretion, such as the breasts, which produce milk, or the lungs, which secrete mucus, or colon or prostate or bladder.

In one embodiment, the carcinoma may be a cancer that arises from epithelial cells that is selected from breast cancer, basal cell carcinoma, adenocarcinoma, gastrointestinal cancer, lip cancer, mouth cancer, esophageal cancer, small bowel cancer and stomach cancer, colon cancer, liver cancer, bladder cancer, pancreas cancer, ovary cancer, cervical cancer, lung cancer, and skin cancer, such as squamous cell and basal cell cancers, prostate cancer, renal cell carcinoma, and other known cancers that effect epithelial cells throughout the body.

Sarcoma refers to cancer that originates in supportive and connective tissues such as bones, tendons, cartilage, muscle, and fat. Generally occurring in young adults, the most common sarcoma often develops as a painful mass on the bone. Sarcomas usually resemble the tissue in which they grow.

Examples of sarcomas are: osteosarcoma or osteogenic sarcoma (bone), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue), mesenchymous or mixed mesodermal tumour (mixed connective tissue types).

Myeloma is cancer that originates in the plasma cells of bone marrow. The plasma cells produce some of the proteins found in blood.

The cancer may be a solid cancer, or a liquid cancer.

For example, leukemias ("liquid cancers" or "blood cancers") are cancers of the bone marrow (the site of blood cell production). The disease is often associated with the over-production of immature white blood cells. These immature white blood cells do not perform as well as they should, therefore the patient is often prone to infection. Leukemia also affects red blood cells and can cause poor blood clotting and fatigue due to anemia. Examples of leukemia include:
  Myelogenous or granulocytic leukemia (malignancy of the myeloid and granulocytic white blood cell series)
  Lymphatic, lymphocytic, or lymphoblastic leukemia (malignancy of the lymphoid and lymphocytic blood cell series)
  Polycythemia vera or erythremia (malignancy of various blood cell products, but with red cells predominating)

Lymphomas develop in the glands or nodes of the lymphatic system, a network of vessels, nodes, and organs (specifically the spleen, tonsils, and thymus) that purify bodily fluids and produce infection-fighting white blood cells, or lymphocytes. Unlike the leukemias which are sometimes called "liquid cancers," lymphomas are "solid cancers." Lymphomas may also occur in specific organs such as the stomach, breast or brain. These lymphomas are referred to as extranodal lymphomas. The lymphomas are subclassified into two categories: Hodgkin lymphoma and Non-Hodgkin lymphoma. The presence of Reed-Sternberg cells in Hodgkin lymphoma diagnostically distinguishes Hodgkin lymphoma from Non-Hodgkin lymphoma.

Mixed types of cancer may include cancers in which the type components are within one category or from different categories of cancer. Some examples are: adenosquamous carcinoma; mixed mesodermal tumour; carcinosarcoma; and teratocarcinoma.

Optionally, the cancer may be a primary cancer, or a metastatic cancer. A primary cancer refers to cancer cells in a primary tumour, which is a tumour appearing at a first site within the subject and which can be distinguished from a metastatic tumour which appears in the body of the subject at a remote site from the primary tumour. A metastatic cancer results from metastasis, which refers to the condition of spread of cancer from the organ of origin to additional distal sites in the patient.

In one preferred embodiment, the histological specimens used in the present invention comprise biological material obtained from subjects having, or suspected of having, a type of cancer selected any one or more of the following list:
  Acute Lymphoblastic Leukemia (ALL),
  Acute Myeloid Leukemia (AML),
  Cancer in Adolescents (e.g. in an adolescent between the age of 12-18 years),
  Adrenocortical Carcinoma, also including for example:
    Childhood Adrenocortical Carcinoma
  AIDS-Related Cancers, also including for example:
    Kaposi Sarcoma (Soft Tissue Sarcoma)
    AIDS-Related Lymphoma (Lymphoma)
    Primary CNS Lymphoma (Lymphoma)
  Anal Cancer
  Appendix Cancer
  Childhood Astrocytomas (Brain Cancer)
  Atypical Teratoid/Rhabdoid Tumour, Childhood, Central Nervous System (Brain Cancer)
  Basal Cell Carcinoma of the Skin
  Bile Duct Cancer
  Bladder Cancer, also including for example:
    Childhood Bladder Cancer
  Bone Cancer (for example, Ewing Sarcoma, Osteosarcoma or Malignant Fibrous Histiocytoma)
  Brain Tumours
  Breast Cancer, also including for example:
    Childhood Breast Cancer
  Childhood Bronchial Tumours
  Burkitt Lymphoma
  Carcinoid Tumour (Gastrointestinal), also including for example:
    Childhood Carcinoid Tumours
  Carcinoma of Unknown Primary, also including for example:
    Childhood Carcinoma of Unknown Primary
  Childhood Cardiac (Heart) Tumours
  Central Nervous System, also including for example:
    Childhood Atypical Teratoid/Rhabdoid Tumour, (Brain Cancer)
    Childhood Embryonal Tumours, (Brain Cancer)
    Childhood Germ Cell Tumour, (Brain Cancer)
    Primary CNS Lymphoma
  Cervical Cancer, also including for example:
    Childhood Cervical Cancer
  Childhood Cancers (e.g. a child that is under the age of 18 years old, preferably under the age of 16, 14 or 12 years old, such as within the range of 1-12 years),
  Unusual Cancers of Childhood,
  Cholangiocarcinoma
  Childhood Chordoma,
  Chronic Lymphocytic Leukemia (CLL)
  Chronic Myelogenous Leukemia (CML)
  Chronic Myeloproliferative Neoplasms
  Colorectal Cancer, also including for example:
    Childhood Colorectal Cancer
  Childhood Craniopharyngioms (Brain Cancer)
  Cutaneous T-Cell Lymphoma
  Ductal Carcinoma in situ (DCIS)
  Embryonal Tumours, Central Nervous System, Childhood (Brain Cancer)
  Endometrial Cancer (Uterine Cancer)
  Childhood Ependymoma (Brain Cancer)
  Esophageal Cancer, also including for example:
    Childhood Esophageal Cancer
  Esthesioneuroblastoma (Head and Neck Cancer)
  Ewing Sarcoma (Bone Cancer)
  Childhood Extracranial Germ Cell Tumour,
  Extragonadal Germ Cell Tumour
  Eye Cancer, also including for example:
    Childhood Intraocular Melanoma
    Intraocular Melanoma
    Retinoblastoma
  Fallopian Tube Cancer
  Fibrous Histiocytoma of Bone, Malignant, and Osteosarcoma
  Gallbladder Cancer
  Gastric (Stomach) Cancer, also including for example:
    Childhood Gastric (Stomach) Cancer
  Gastrointestinal Carcinoid Tumour
  Gastrointestinal Stromal Tumours (GIST) (Soft Tissue Sarcoma), also including for example:
    Childhood Gastrointestinal Stromal Tumours
  Germ Cell Tumours, also including for example:
    Childhood Central Nervous System Germ Cell Tumours (Brain Cancer)
    Childhood Extracranial Germ Cell Tumours
    Extragonadal Germ Cell Tumours
    Ovarian Germ Cell Tumours
    Testicular Cancer
  Gestational Trophoblastic Disease
  Hairy Cell Leukemia
  Head and Neck Cancer
  Childhood Heart Tumours
  Hepatocellular (Liver) Cancer
  Histiocytosis, Langerhans Cell
  Hodgkin Lymphoma
  Hypopharyngeal Cancer (Head and Neck Cancer)

Intraocular Melanoma, also including for example:
  Childhood Intraocular Melanoma
Islet Cell Tumours, Pancreatic Neuroendocrine Tumours
Kaposi Sarcoma (Soft Tissue Sarcoma)
Kidney (Renal Cell) Cancer
Langerhans Cell Histiocytosis
Laryngeal Cancer (Head and Neck Cancer)
Leukemia
Lip and Oral Cavity Cancer (Head and Neck Cancer)
Liver Cancer
Lung Cancer (Non-Small Cell and Small Cell), also including for example:
  Childhood Lung Cancer
Lymphoma
Male Breast Cancer
Malignant Fibrous Histiocytoma of Bone and Osteosarcoma
Melanoma, also including for example:
  Childhood Melanoma
Intraocular (Eye) Melanoma, also including for example:
  Childhood Intraocular Melanoma
Merkel Cell Carcinoma (Skin Cancer)
Malignant Mesothelioma, also including for example:
  Childhood Mesothelioma
Metastatic Cancer
Metastatic Squamous Neck Cancer with Occult Primary (Head and Neck Cancer)
Midline Tract Carcinoma with NUT Gene Changes
Mouth Cancer (Head and Neck Cancer)
Multiple Endocrine Neoplasia Syndromes
Multiple Myeloma/Plasma Cell Neoplasms
Mycosis Fungoides (Lymphoma)
Myelodysplastic Syndromes, Myelodysplastic/Myeloproliferative Neoplasm
Chronic Myelogenous Leukemia (CML)
Acute Myeloid Leukemia (AML)
Chronic Myeloproliferative Neoplasms
Nasal Cavity and Paranasal Sinus Cancer (Head and Neck Cancer)
Nasopharyngeal Cancer (Head and Neck Cancer)
Neuroblastoma
Non-Hodgkin Lymphoma
Non-Small Cell Lung Cancer
Oral Cancer, Lip and Oral Cavity Cancer and Oropharyngeal Cancer (Head and Neck Cancer)
Osteosarcoma and Malignant Fibrous Histiocytoma of Bone
Ovarian Cancer, also including for example:
  Childhood Ovarian Cancer
Pancreatic Cancer, also including for example:
  Childhood Pancreatic Cancer
Pancreatic Neuroendocrine Tumours (Islet Cell Tumours)
Papillomatosis (Childhood Laryngeal)
Paraganglioma, also including for example:
  Childhood Paraganglioma
Paranasal Sinus and Nasal Cavity Cancer (Head and Neck Cancer)
Parathyroid Cancer
Penile Cancer
Pharyngeal Cancer (Head and Neck Cancer)
Pheochromocytoma, also including for example:
  Childhood Pheochromocytoma
Pituitary Tumour
Plasma Cell Neoplasm/Multiple Myeloma
Pleuropulmonary Blastoma
Pregnancy and Breast Cancer (i.e. breast cancer in a pregnant female)
Primary Central Nervous System (CNS) Lymphoma
Primary Peritoneal Cancer
Prostate Cancer
Rectal Cancer
Recurrent Cancer
Renal Cell (Kidney) Cancer
Retinoblastoma
Childhood Rhabdomyosarcoma (Soft Tissue Sarcoma)
Salivary Gland Cancer (Head and Neck Cancer)
Sarcoma, also including for example:
  Childhood Rhabdomyosarcoma (Soft Tissue Sarcoma)
  Childhood Vascular Tumours (Soft Tissue Sarcoma)
  Ewing Sarcoma (Bone Cancer)
  Kaposi Sarcoma (Soft Tissue Sarcoma)
  Osteosarcoma (Bone Cancer)
  Soft Tissue Sarcoma
  Uterine Sarcoma
Sézary Syndrome (Lymphoma)
Skin Cancer, also including for example:
  Childhood Skin Cancer
Small Cell Lung Cancer
Small Intestine Cancer
Soft Tissue Sarcoma
Squamous Cell Carcinoma of the Skin
Metastatic Squamous Neck Cancer with Occult Primary (Head and Neck Cancer)
Stomach (Gastric) Cancer, also including for example:
  Childhood Stomach (Gastric) Cancer
Cutaneous T-Cell Lymphoma
Testicular Cancer, also including for example:
  Childhood Testicular Cancer
Throat Cancer (Head and Neck Cancer), also including for example:
  Nasopharyngeal Cancer
  Oropharyngeal Cancer
  Hypopharyngeal Cancer
Thymoma and Thymic Carcinoma
Thyroid Cancer
Transitional Cell Cancer of the Renal Pelvis and Ureter (Kidney (Renal Cell) Cancer)
Carcinoma of Unknown Primary, also including for example:
  Childhood Cancer of Unknown Primary
Unusual Cancers of Childhood
Ureter and Renal Pelvis, Transitional Cell Cancer (Kidney (Renal Cell) Cancer)
Urethral Cancer
Endometrial Uterine Cancer
Uterine Sarcoma
Vaginal Cancer, also including for example:
  Childhood Vaginal Cancer
Vascular Tumours (Soft Tissue Sarcoma)
Vulvar Cancer
Wilms Tumour and Other Childhood Kidney Tumours
Cancer in Young Adults (e.g. in a young adult ages 16-30, such as 18-30 years old; optionally less than 28, 26, 24, 22 or 20 years old)

More specifically, in a preferred embodiment, the biological source for a source-histological-image for use in the present invention may consist, consist essentially of, or comprise, biological material obtained from a subject (such as a human subject) that has, has been diagnosed as having, is suspected of having, is being treated for, has been treated for, and/or has previously had a type of cancer selected any one or more of the following list:

Skin Cancer: There are three primary types of skin cancer: basal cell, squamous cell, and melanoma. These cancers are derived from the epidermal layers with the same names. Melanomas are derived from the melanocytes, or pigment cells, in the deepest level of the epidermis. Basal cell and squamous cell cancers usually occur on parts of the body exposed to the sun, such as the face, ears, and extremities.

Lung Cancer: Lung cancer is very difficult to detect at an early stage because the symptoms often do not appear until the disease has advanced. The symptoms include persistent cough, sputum streaked with blood, chest pain, and repeated attacks of pneumonia or bronchitis.

Female or Male Breast Cancer: It has been estimated that in the U.S., about 1 in 8 women will eventually develop breast cancer in her lifetime. Most breast cancers are ductal carcinomas. Women most likely to develop the disease are those over the age of 50; those who have already had cancer in one breast; those whose mother or sister had breast cancer; those who never had children; and those who had their first child after the age of 30. Other risk factors include obesity, a high-fat diet, early menarche (age menstruation begins) and late menopause (age menstruation ceases).

Prostate Cancer: Cancer of the prostate is found mainly in older men. As men age, the prostate may enlarge and block the urethra or bladder. This may cause difficulty in urination or interfere with sexual functions. This condition is called benign prostatic hypertrophy (BPH). Although BPH is not cancerous, surgery may be needed to correct it. The symptoms of BPH, or of other problems in the prostate, may be similar to symptoms for prostate cancer.

Colon and/or Rectum Cancer: Colorectal cancer (CRC) is a disease typically originating from the epithelial cells lining the colon or rectum of the gastrointestinal tract. Of the cancers that affect the large intestine, about 70 percent occur in the colon and about 30 percent in the rectum. These cancers are the third most common cancers overall. Symptoms include blood in the stool, which can be tested for by a simple faecal occult blood test, or a change in bowel habits, such as severe constipation or diarrhoea.

Uterus (Corpus Uteri) Cancer: The uterus is the sac in a woman's pelvis which allows a baby to develop from a fertilized egg and protects it until birth. Cancer of the uterus is the most common gynaecologic malignancy. This cancer occurs infrequently in women under 40 years of age. It occurs most frequently after the age of 60. The presenting symptom is usually abnormal uterine bleeding. An endometrial biopsy or D&C is often performed to confirm the diagnosis.

In addition to cancer types named after the primary site discussed above, there are many other examples such as brain cancer, testicular cancer, bladder cancer, and so on.

2.3.2 Treatment:

As discussed above, the biological source for a histopathological sample, from which a source-histopathological-image is generated, may be a subject (such as a human subject) that is being treated for, and/or has been previously treated for, a pathological condition (such as cancer).

Additionally, and/or alternatively, the subject may, for example, be a subject that has a pathological condition of interest (including, without limitation, cancer) and, for example, for whom it is desirable to obtain further information about the pathological condition to aid the making of a decision about the need, nature and/or potential benefit of a future treatment for that pathological condition.

The subject may, for example, be a subject that has been diagnosed with a pathological condition of interest (including, without limitation, cancer) and have already received one or more treatments for that pathological condition, for whom it is desirable to know whether they still have the pathological condition and/or to obtain further information about the biological material at the site in the body of the subject at which the pathological condition was previously treated or any other site in the body of the subject, to aid the making of a decision about the need, nature and/or potential benefit of a future treatment for that pathological condition.

Any such forms of treatment for a pathological condition (including cancer) are included, and the skilled person is well aware of such treatments in the art, including without limitation, surgical and/or non-surgical therapeutic approaches (for example, the administration of one or more compositions, the or each composition comprising one or more active agents that provide a therapeutic and/or prophylactic effect in respect of the pathological condition), and how to match the form of treatment to the type of pathological condition.

More specifically, and without limitation, cancer treatments include surgery, radiation therapy, chemotherapy, bisphosphonates, gene therapy, immunotherapy, targeted therapy, hormone therapy, stem cell and/or bone marrow transplant, and/or precision medicine. Further cancer treatments include, without limitation, radiofrequency ablation, laser treatment, high intensity focused ultrasound (HIFU), photodynamic therapy, cryotherapy, ultraviolet light treatment and/or electrochemotherapy. On one embodiment, the cancer treatment (e.g. in the context of making a decision about the need, nature and/or potential benefit of a future treatment for that pathological condition) may be a form of adjuvant therapy. An adjuvant therapy is a form of treatment that is given in addition to a primary (initial) treatment. Adjuvant therapy for cancer includes a form of therapy that follows a primary (e.g. surgical) treatment, and may be a form of cancer therapy (for example, chemo- or radiotherapy, or any other form of cancer therapy) that is intended to treat any cancer cells remaining in the subject after the primary treatment and/or help decrease the risk of the cancer recurring.

2.3.3 Subject Characteristics:

As discussed above, a subject (such as human subjects) that acts as a source for the biological material present in a histological specimen that is used in accordance with the present invention, may be a healthy subject, or more typically a pathological subject.

The subject may optionally be a male, such as a male human.

The subject may optionally be a female, such as a female human.

The subject may, for example, be an adult, an adolescent, a juvenile, a child, an infant, a neonate, a foetus or an embryo; such as a human adult, human adolescent, human juvenile, human child, human infant, human neonate, human foetus or human embryo.

The subject may, for example, be a human infant aged less than 1, 2, 3, 4, 5, 6, 7 8, 9, 10, 11 or 12 months old.

The subject may be, for example, be a human (e.g. a male human and/or a female human) aged at least or more than 1 year old, for example, at least or greater than 2, 3, 4, 5, 6, 7, 8, 9, 10, 11, 12, 13, 14, 15, 16, 17, 18, 19, or 20 years old; and optionally less than 100, 90, 85, 80, 75, 65, 60, 55, 50, 45 or 40 years old.

The subject may be, for example, be a human (e.g. a male human and/or a female human) aged at least or more than 20 years old, for example, at least or greater than 25, 30, 35, 40, 45, 50, 55, 60, 65, 70, 75 or 80 years old; and optionally less than 100, 90 or 85 years old.

A pathological subject may be a subject (such as a human subject) that has, has been diagnosed as having, is suspected of having, is being treated for, has previously been treated for, and/or has previously had, a pathological condition.

In the case of histological specimens comprising biological material from a pathological subject, the histological specimens may contain, or be suspected of containing, biological material comprising the pathological condition present in the subject. Such pathologies include, without limitation, those pathologies discussed above in section 2.3 of this application, and in a preferred embodiment the pathological condition may be a form of cancer, for example a type of cancer as discussed above in section 2.3.1 of this application.

The subject may, for example, be a subject that has not previously been diagnosed with a pathological condition of interest (including, without limitation, cancer), but, for example, for whom it is desirable to know whether they have and/or are at risk of developing or progressing that pathological condition.

The subject may, for example, be a subject that has a pathological condition of interest (including, without limitation, cancer) and, for example, for whom it is desirable to obtain further information about the pathological condition, for example to determine their prognosis and/or to aid the making of a decision about the need, nature and/or potential benefit of a future treatment for that pathological condition.

The subject may, for example, be a subject that has been diagnosed with a pathological condition of interest (including, without limitation, cancer) and has already received one or more treatments for that pathological condition (for example, as discussed above in section 2.3.2 of this application), for whom it is desirable to know whether they still have the pathological condition and/or to obtain further information about the biological material at the site in the body of the subject at which the pathological condition was previously treated or any other site in the body of the subject, for example to determine their prognosis and/or to aid the making of a decision about the need, nature and/or potential benefit of a future treatment for that pathological condition.

For example, in the case that the pathological condition is cancer, then the specimen may be taken from:

A subject that has not previously been diagnosed with cancer but, for example, for whom it is desirable to know whether they have cancer;

A subject that has been diagnosed with cancer and, for example, it is desirable to obtain further information about the cancer, for example to determine their prognosis and/or to aid the making of a decision about the need, nature and/or potential benefit of a future treatment of the cancer; and/or A subject that has been diagnosed with cancer and has already received one or more treatments for that cancer, for whom it is desirable to know whether they still have cancer and/or obtain further information about the biological material at the site in the body of the subject at which the cancer was previously treated or any other site in the body of the subject, for example to determine their prognosis and/or to aid the making of a decision about the need, nature and/or potential benefit of a future treatment of the cancer.

The subject (such as a human subject) that acts as a source for the biological material present in a histological specimen that is used in accordance with the present invention, may be a subject that has, and/or has been determined to have, a risk (e.g. a higher than average risk) of developing a pathological condition (including, without limitation, cancer).

Known risk factors in the context of cancer include, without limitation, age, alcohol consumption, exposure to cancer-causing substances, chronic inflammation, diet, hormones, immunosuppression, infectious agents, obesity, radiation, sunlight and tobacco. The subject (such as a human subject) that acts as a source for the biological material present in a histological specimen that is used in accordance with the present invention, may be a subject that has, and/or has been determined to have, a risk of developing cancer based on one or more of the foregoing risk factors.

Advancing age is the one of most important risk factor for cancer overall, and for many individual cancer types. According to the most recent statistical data from NCI's Surveillance, Epidemiology, and End Results program, the median age of a cancer diagnosis is 66 years. This means that half of cancer cases occur in people below this age and half in people above this age. One-quarter of new cancer cases are diagnosed in people aged 65 to 74. A similar pattern is seen for many common cancer types. For example, the median age at diagnosis is 61 years for breast cancer, 68 years for colorectal cancer, 70 years for lung cancer, and 66 years for prostate cancer. Accordingly, in an embodiment of the present disclosure, the pathological condition is cancer and the subject is a human (e.g. a male human and/or a female human) aged at least or more than 50, 55, 60, 65, 70, 75 or 80 years old; and optionally less than 100, 90 or 85 years old; for example at an age of from 50 to 85 years old, from 60 to 85 years old, from 65 to 85 years old, or from 65 to 75 years old.

But cancer can occur at any age. For example, bone cancer is most frequently diagnosed among people under age 20, with more than one-fourth of cases occurring in this age group. And 10 percent of leukemias are diagnosed in children and adolescents under 20 years of age, whereas only 1 percent of cancer overall is diagnosed in that age group. Some types of cancer, such as neuroblastoma, are more common in children or adolescents than in adults.

Tobacco use is a leading cause of cancer and of death from cancer. People who use tobacco products or who are regularly around environmental tobacco smoke (also called secondhand smoke) have an increased risk of cancer because tobacco products and secondhand smoke have many chemicals that damage DNA. Tobacco use causes many types of cancer, including cancer of the lung, larynx (voice box), mouth, esophagus, throat, bladder, kidney, liver, stomach, pancreas, colon and rectum, and cervix, as well as acute myeloid leukemia. People who use smokeless tobacco (snuff or chewing tobacco) have increased risks of cancers of the mouth, esophagus, and pancreas. Accordingly, in an embodiment of the present disclosure, the pathological condition is cancer and the subject is a human (e.g. a male human and/or a female human) with a history of tobacco use (including tobacco exposure, such as secondhand smoke).

Drinking alcohol can increase the risk of cancer, for example cancer of the mouth, throat, esophagus, larynx (voice box), liver, and/or breast. The more alcohol a subject drinks, the higher their risk. The risk of cancer is much higher for those who drink alcohol and also use tobacco. Accordingly, in an embodiment of the present disclosure, the pathological condition is cancer and the subject is a human (e.g. a male human and/or a female human) with a history of alcohol consumption (typically, higher than average alcohol consumption) and/or tobacco use.

Hormone levels can influence the risk of cancer. For example, estrogens, a group of female sex hormones, are known human carcinogens. Although these hormones have essential physiological roles in both females and males, they have also been associated with an increased risk of certain cancers. For instance, taking combined menopausal hormone therapy (estrogen plus progestin, which is a synthetic version of the female hormone progesterone) can increase a woman's risk of breast cancer. Menopausal hormone therapy with estrogen alone increases the risk of endometrial cancer and is used only in women who have had a hysterectomy. Studies have also shown that a woman's risk of breast cancer is related to the estrogen and progesterone made by her ovaries (known as endogenous estrogen and progesterone). Being exposed for a long time and/or to high levels of these hormones has been linked to an increased risk of breast cancer. Increases in exposure can be caused by starting menstruation early, going through menopause late, being older at first pregnancy, and never having given birth. Conversely, having given birth may be a protective factor for breast cancer.

Diethylstilbestrol (DES) is a form of estrogen that was given to some pregnant women in the United States between 1940 and 1971 to prevent miscarriages, premature labor, and related problems with pregnancy. Women who took DES during pregnancy have an increased risk of breast cancer. Their daughters have an increased risk of a cancer of the vagina or cervix. The possible effects on the sons and grandchildren of women who took DES during pregnancy are being studied.

Accordingly, in an embodiment of the present disclosure, the pathological condition is cancer and the subject is a human (e.g. a male human and/or a female human) with an associated hormonal risk factor.

Subjects in receipt of immunosuppression may also be at increased risk of cancer. For example, organ transplant recipients typically receive immunosuppression medications. Immunosuppressive drugs make the immune system less able to detect and destroy cancer cells or fight off infections that cause cancer. Infection with HIV and other immunosuppressive pathogens can also weaken the immune system and increases the risk of certain cancers.

The four most common cancers among transplant recipients and that occur more commonly in these individuals than in the general population are non-Hodgkin lymphoma (NHL) and cancers of the lung, kidney, and liver. NHL can be caused by Epstein-Barr virus (EBV) infection, and liver cancer by chronic infection with the hepatitis B (HBV) and hepatitis C (HCV) viruses. Lung and kidney cancers are not generally thought to be associated with infection.

People with HIV/AIDS also have increased risks of cancers that are caused by infectious agents, including EBV; human herpesvirus 8, or Kaposi sarcoma-associated virus; HBV and HCV, which cause liver cancer; and human papillomavirus, which causes cervical, anal, oropharyngeal, and other cancers. HIV infection is also associated with increased risks of cancers that are not thought to be caused by infectious agents, such as lung cancer.

Accordingly, in an embodiment of the present disclosure, the pathological condition is cancer and the subject is an immunosuppressed human (e.g. a male human and/or a female human).

Exposure to certain infectious agents, including viruses, bacteria, and parasites, can cause cancer or increase the risk that cancer will form. Some viruses can disrupt signaling that normally keeps cell growth and proliferation in check. Also, some infections weaken the immune system, making the body less able to fight off other cancer-causing infections. And some viruses, bacteria, and parasites also cause chronic inflammation, which may lead to cancer. Most of the viruses that are linked to an increased risk of cancer can be passed from one person to another through blood and/or other body fluids. Exemplary infections agents that can cause, or increase the risk of, cancer, include: Epstein-Barr Virus (EBV), Hepatitis B Virus and Hepatitis C Virus (HBV and HCV), Human Immunodeficiency Virus (HIV), Human Papillomaviruses (HPVs), Human T-Cell Leukemia/Lymphoma Virus Type 1 (HTLV-1), Kaposi Sarcoma-Associated Herpesvirus (KSHV), Merkel Cell Polyomavirus (MCPyV), *Helicobacter pylori* (*H. pylori*), *Opisthorchis viverrini* and *Schistosoma hematobium*.

Accordingly, in an embodiment of the present disclosure, the pathological condition is cancer and the subject is a human (e.g. a male human and/or a female human) that has (whether or not actually diagnosed), is suspected of having, is being treated for, has been treated for, and/or has previously had, an infection with an infectious agents, that can cause cancer or which increases the risk that cancer will form.

People who are obese may have an increased risk of several types of cancer, including cancers of the breast (in women who have been through menopause), colon, rectum, endometrium (lining of the uterus), esophagus, kidney, pancreas, and gallbladder. Accordingly, in an embodiment of the present disclosure, the pathological condition is cancer and the subject is an obese human (e.g. a male human and/or a female human).

In a further embodiment of the present disclosure, the pathological condition is cancer and the subject is a human (e.g. a male human and/or a female human) that has and optionally has been determined to have, a genetic risk factor for cancer. The genetic risk factor may, for example, by an inherited genetic trait, or an acquired genetic trait. Many types of genetic risk factors are well known in the art, for example and without limitation, Lynch syndrome, BRCA gene, retinoblastoma gene, etc.

2.4 Preparation of a Histological Specimen

The skilled person is well aware of numerous techniques well known in the art for the preparation of a histological specimen from a biological material obtained from a biological source. Any suitable means for the preparation of a histological specimen can be used in the context of the present invention.

For example, without limitation, for specimens to be examined (e.g. by light microscopy and/or WSI imaging), three techniques are commonly used: the paraffin technique, frozen sections, and semithin sections.

The paraffin technique is the most commonly used. In this technique, tissues are fixed, and embedded in wax. This makes the tissue hard, and much easier to cut sections from. The sections are then stained, to help distinguish the components of the tissue.

Fixation involves the chemical fixation of a biological sample. The chemical added binds to and cross-links some proteins, and denatures other proteins through dehydration. This hardens the tissue, and inactivates enzymes that might otherwise degrade the tissue. Fixation also kills bacteria, etc., and it can also enhance tissue staining. A common fixative is a 4% aqueous solution of formaldehyde, at neutral pH. Another common option is Formalin-Fixed Paraffin-Embedded (FFPE) tissue specimens, which have been a staple of research and therapeutic applications for decades.

Following fixation, the sample is typically subjected to the steps of dehydration and clearing, embedding, sectioning, staining and mounting.

Dehydration and Clearing: To cut sections, it may be desirable to embedded the fixed biological sample in paraffin wax, but wax is not soluble in water or alcohol. However, it is soluble in a solvent, such as xylene. Therefore, the water in the tissue can be replaced with the solvent. To do this, first the tissue is dehydrated, for example, by gradually replacing water in the sample with alcohol. This can be achieved, for example, by passing the tissue through increasing concentrations of ethyl alcohol (from 0 to 100%). Finally, once the water has been replaced by 100% alcohol, the alcohol is replaced with the solvent (e.g. xylene), which is miscible with alcohol. This final step is called 'clearing'.

Following the dehydration and clearing steps, the sample is typically treated with the embedding step. For example, the tissue may be placed in warm paraffin wax, and the melted wax allowed to fill the spaces that used to have water in them. After cooling, the tissue hardens, and can be used to cut slices (sectioned).

For the step of sectioning, the tissue is trimmed, and mounted on a cutting device (e.g. microtome or ultramicrotome). Thin sections are cut, which can be stained and mounted on a microscope slide. In this context, a 'thin' section can include sections that are about one cell's depth or less. Typically cells in samples taken from animal or human biological sources can be, for example, 10-15 µm in diameter, and a thin section may be of equivalent or lesser thickness, such as 5-10 µm in thickness.

In one option, it may be desirable to cut multiple physically separate (typically, consecutive parallel or essentially parallel) thin sections of the biological material for the purpose of obtaining a collection of source-histological images which, together, can form a three-dimensional source-histological image.

In another option, it may be desirable to cut thick sections, which can be stained and mounted on a microscope slide, and from which multiple images (for example, consecutive parallel or essentially parallel images) can be obtained by selective focussing techniques in a plurality of planes within the thick section. Selective focussing techniques are known in the art, for example Mir et al, 2014: *"An extensive empirical evaluation of focus measures for digital photography"* in Proceedings of SPIE—The International Society for Optical Engineering 9023 (available online at https://cs.uwaterloo.ca/~vanbeek/Publications/spie2014.pdf), and Hosseini et al., submitted to the IEEE in 2018 for possible publication: *"Focus Quality Assessment of High-Throughput Whole Slide Imaging in Digital Pathology"* (available online at https://arxiv.org/pdf/1811.06038.pdf), the contents of both of which are incorporated herein by reference.

In this context, a 'thick' section can include sections having a thickness that is greater than one cell's depth, for example up to 2, 3, 4, 5, 6, 7, 8, 9, 10, 20, 30, 40, 50, 60, 70, 80, 90, 100 or more cells' depth. As noted above, it is typical for cells in samples taken from animal or human biological sources to be, for example, 10-15 µm in diameter. Accordingly, a thick section in that context may have a thickness that is greater than 10 µm, 15 µm, 20 µm, 25 µm, 30 µm, 40 µm, 50 µm, 60 µm, 70 µm, 80 µm, 90 µm, 100 µm, 150 µm, 200 µm, 250 µm, 300 µm, 400 µm, 500 µm or more. For example, in the case that multiple consecutive parallel or essentially parallel images are obtained by selective focussing techniques in a plurality of planes within the thick section, then this is a further way in which a collection of source-histological images can be provided which, together, can form a three-dimensional source-histological image.

Staining and Mounting: Unfortunately, most staining solutions are aqueous, so to stain the sections, the wax may need to be dissolved and replaced with water (rehydration). This is essentially the dehydration and clearing steps in reverse. The sections are passed through a wax solvent (e.g. xylene), and then decreasing strengths of alcohol (100% to 0%) and finally water. Once stained, the section may be dehydrated once again, and placed in the solvent (e.g. xylene). It may then be mounted on a microscope slide in mounting medium dissolved in the solvent. A coverslip may be placed on top, to protect the sample. Evaporation of solvent (e.g. xylene) may be permitted around the edges of the coverslip, which dries the mounting medium and bonds the coverslip firmly to the slide.

Alternative means for the preparation of a histological specimen include, without limitation, the preparation of frozen sections and semithin sections.

For the production of frozen sections, tissues are frozen rapidly (e.g. in liquid nitrogen), and then cut whilst cold (e.g. in a cold refrigerated cabinet (a cryostat) with a cold knife), then stained in preparation for observation. This procedure is faster, and can preserve some tissue details that may be lost by the paraffin technique. Frozen sections are typically 5-10 µm thick, although any suitable thickness can be selected for the desired objective, including any of the thicknesses discussed above.

Semithin sections may be useful in circumstances in which it can be hard to see detail in thick sections. To get around this, sections can be embedded in epoxy or acrylic resin, which enable thinner sections (e.g. less than 2 µm) to be cut.

2.4.1 Staining Histological Specimens

A histological image, or a histopathological image may be prepared by suitably staining a histological, or histopathological, specimen, as already discussed above. At the microscopic scale, many of the interesting features of cells are not naturally visible, because they are transparent and colourless. To reveal these features, specimens are commonly stained with a marker before being imaged under a microscope. The marker includes one or more colorants (dyes or pigments) that are designed to bind specifically to particular components of the cell structure, thus revealing the histological feature of interest. The skilled person is well aware of numerous staining techniques well known in the art. Any suitable means for the staining of a histological specimen can be used in the context of the present invention. Without limitation, such staining techniques that may be suitable for use with the present invention are discussed further below.

The techniques used can either be non-specific, staining most of the cells in much the same way, or specific, selectively staining particular chemical groupings or molecules within cells or tissues. Staining usually works by using a dye, that stains some of the cell components a first colour, together with one or more counterstains that stain the rest of the cell one or more different colours.

For example, the staining technique may use basophilic and acidophilic staining.

Acidic dyes (e.g. eosin) react with cationic or basic components in cells. Most proteins, and many other components in the cytoplasm are basic, and will bind to acidic dyes. This includes, for example, cytoplasmic filaments in muscle cells, intracellular membranes, and extracellular fibres.

Basic dyes (e.g. haemotoxylin) react with anionic or acidic components in cells. Nucleic acids are acidic, and therefore bind to basic dyes. For example, DNA (heterochromatin and the nucleolus) in the nucleus, and RNA in ribosomes and in the rough endoplasmic reticulum are both acidic, and so binds to basic dyes. Some extracellular materials (e.g. carbohydrates in cartilage) will also bind to basic dyes.

For the purposes of the present invention, in one preferred embodiment, the staining used is a staining system called H&E (Haemotoxylin and Eosin). H&E contains the two dyes haemotoxylin and eosin. Eosin is an acidic dye: it is negatively charged, and it stains basic (i.e. acidophilic) structures red or pink. This is also sometimes termed 'eosinophilic'. Haematoxylin can be considered as a basic dye, and it is used to stain acidic (i.e. basophilic) structures a purplish blue. Accordingly, when histological samples are stained with the H&E system the nucleus, and parts of the cytoplasm that contain RNA will be typically stained in one colour (purple), and the rest of the cytoplasm will be typically stained a different colour (pink).

However, it will be appreciated that the present invention is not limited with respect to the use of any particularly staining technique. For example, numerous other acidic and basic dyes are known in the art. Examples are shown in the following table:

Exemplary Histological Stains other than H&E can include:

| Basic dyes | |
|---|---|
| Methyl green | Green |
| Methylene blue | Blue |
| Pyronin G | Red |
| Toluidine blue | Blue |
| Acidic dyes | |
| Acid fuschin | Red |
| Aniline Blue | Blue |
| Eosin | Red |
| Orange G | Orange |

For basic dyes, the reaction of the anionic groups of cells (these include the phosphate groups of nucleic acids, sulphate groups of glycosoaminoglycans, and carboxyl groups of proteins) may depend on the pH at which they are used.

For acidic dyes, the dye in question can often in addition be selective for particular acidophilic components. For example, the well-known technique called the Mallory staining technique uses three acidic dyes: aniline blue, acid fuschin and orange G, which selectively stain collagen, cytoplasm and red blood cells respectively.

Further stain techniques for use with the present invention, as contemplated herein, include:

Periodic acid-Schiff reaction (PAS), in which the Schiff reagent is a bleached basic fuschin that reacts with aldehyde groups. This reaction results in a deep red colour in the section. It is the basis of the PAS stain. PAS stains carbohydrates and carbohydrate rich macromolecules a deep red colour (magenta). PAS will therefore stain up: glycogen the intracellular storage form of carbohydrate in cells, mucus in cells and tissues, Basement membranes, and Brush borders of kidney tubules and small and large intestines Reticular fibres (i.e. collagen) in connective tissue and cartilage.

Masson's trichrome, which is often used to stain connective tissue. The term "tri-chrome" means that the technique produces three colours. Nuclei and other basophilic structures are stained blue, cytoplasm, muscle, erythrocytes and keratin are stained bright-red. Collagen may be stained green or blue, depending on which variant of the technique is used.

Alcian blue is a mucin stain that stains certain types of mucin blue. Cartilage is also stained blue. It can be used with other staining systems, such as H&E, and with van Gieson stains.

The van Gieson technique stains collagen red, nuclei blue, and erythrocytes and cytoplasm yellow. It can also be combined with an elastin stain that stains elastin blue/black. It is often used for blood vessels and skin.

The reticulin stain technique stains reticulin fibres blue/black. It may be used with other staining techniques, for example with H&E The azan stain causes nuclei to be stained bright red, collagen, basement membrane and mucin to be stained blue, and muscle and red blood cells to be stained orange to red. This technique can be particularly appropriate for staining connective tissue and epithelium.

The giemsa staining technique is usually used for staining blood and bone-marrow smears. Nuclei are stained dark-blue to violet, cytoplasm pale blue, erythrocytes pale pink.

Toluidine blue is a basic stain that stains acidic components various shades of blue. It is usually used for thin acrylic or epoxy sections.

Silver and gold methods may be used to demonstrate fine structures such as cell processes in neurones. This technique produces a black, brown or golden stain.

Chrome alum/haemotoxylin is a less commonly used technique, which stains nuclei blue, and cytoplasm red. It may be particularly useful with samples from the pancreas, in which glucagon secreting cells are stained pink and insulin secreting cells are stained blue.

Isamin blue/eosin is a staining technique like H&E, but the blue is more intense.

Nissl and methylene blue is a staining technique that may be used, for example, as a basic dye to stain the rough ER in neurones.

Sudan Black and osmium are dyes that stain lipid-containing structures, such as myelin, a brownish-black colour.

Immunohistochemical (IHC) techniques may also be used (alone, or in combination with any one or more of the foregoing techniques). Immunohistochemical techniques are well know in the art. Typically, primary antibodies are used that specifically label a protein (or other specific target), and then a labelled secondary antibody (e.g. fluorescently-labelled) may be used to bind to the primary antibody, to show up where the first (primary) antibody has bound. The label may be detected by any suitable means. For example, in the case of a method that uses fluorescently-labelled antibodies, a light microscope (or equivalent imaging apparatus), equipped with fluorescence, may be used to visualise the staining. The fluorescent antibodies are excited at one wavelength of light, and they then emit light at a different wavelength. Using the right combination of filters, the staining pattern produced by the emitted fluorescent light can be observed.

IHC techniques may be increasingly useful in the context of the imaging of samples containing, or suspected of containing, cancer. In such techniques, the primary antibody may, for example, be targeted to tumour markers. Tumour markers are molecules whose levels are considered as signals, symbols, or representatives of tumour cells, and which may be increased in cancerous conditions. Tumour markers can include, without limitation, proteins, patterns of gene expression, and DNA changes. Tumour markers visualised by IHC can include enzymes, oncogenes, tumour-specific antigens, tumour suppressor genes and tumour proliferation markers, amongst others.

3. Ground-Truths

As discussed in more detail in section 1 of the present application, and as further defined by the present claims, the present application describes a computer implemented system (100; 200; 300) for determining a classifier (118;318), or an overall-classifier (232; 332), for a source-histological-image (102; 202; 302), which may be a source-histopathological-image.

As also discussed in more detail in section 2 of the present application, in the training phase, in which the system (100; 200; 300) can be used for training machine learning algorithms within the system (100; 200; 300), the source-histological-images used for training are images of histological specimens obtained from sources for which a ground-truth is known. Each of the source-histological-images are then labelled with the associated truth-data representing the ground-truth for each source from which each histological specimen was obtained.

A "ground-truth" in this context can be any information of interest that is associated with the, or each, source-histological-image. Any useful measure that can be associated with each of the images can be applied as a "ground-truth". It will be understood that the selection of the ground-truth is an important feature for determining the functionality and utility of the subsequently trained machine learning algorithm.

For example, an algorithm that is trained using source-histopathological-images of histopathological specimens for which the ground-truth associated with each image is a known diagnosis for (for example, the presence or absence of) a particular pathological condition, then the subsequently trained algorithm will be suitable for use in the diagnosis of that pathological condition (and/or, risk of developing that pathological condition) in microscopic images of histological specimens taken from subjects of unknown diagnosis ('test subjects'), and consequently therefore will also be suitable for use in the diagnosis of that pathological condition in test subjects.

In another example, an algorithm that is trained using source-histopathological-images of histopathological specimens for which the ground-truth associated with each image may be a known prognosis for a particular pathological condition, and then the subsequently trained algorithm will be suitable for use in the prognosis of that pathological condition in microscopic images of histological specimens taken from subjects of unknown prognosis ("test subjects"), and consequently therefore will also be suitable for use in the prognosis of test subjects.

In the examples described herein, the histological specimens were obtained from cancer patients, and the ground-truth related to the categorisation of each patient into a prognostic group.

In one embodiment described herein, the histological specimens may be obtained from patients with one or more types of cancer, and the ground-truth related to the categorisation of the stage and/or grade of the cancer present within each patient, in particular in which the stage and/or grade is correlated with a defined prognosis.

For example, the subsequently trained algorithm may then be suitable for use in automatically identifying the stage and/or grade of the cancer present within microscopic images of histological specimens taken from one or more subjects of undetermined stages and/or grades of cancer and/or unknown prognosis ("test subjects"), and consequently therefore can optionally also be used in the prognosis of the cancer(s) in the test subjects.

In an additional or alternative option, the subsequently trained algorithm may then be suitable for use in automatically and directly predicting a cancer-specific prognosis (e.g. survival) in the test subject(s) and, optionally used for making one or more further treatment decisions (such as the decision to engage in further treatment and/or the selection of the type of treatment) by identifying subjects at low risk who may have a good prognosis and who therefore may not be likely to benefit from further treatment and/or identifying subjects at high risk who are much more likely to benefit from further therapy, such as more intensive treatment regimes.

Optionally, the one or more histological specimens may be from one or more subjects test subject(s) that have already received a surgical treatment for cancer (e.g. tumour resection), and that trained algorithm may be used to automatically and directly predict a cancer-specific prognosis (e.g. survival) in the test subject(s) and, optionally be used for making one or more further adjuvant treatment decisions.

Any of the cancers described herein can suitably assessed, although a cancer of particular interest is colorectal cancer as exemplified herein.

More generally, by way of example, the training phase may involve the use of source-histological-images of histological specimens that comprise biological material obtained from healthy subjects, and/or from pathological subjects (which may include, without limitation, those pathologies discussed above in section 2. 3 of this application, and in an embodiment of particular interest, may be a form of cancer such as discussed above in section 2.3.1 of this application), wherein the ground-truth associated with each of the source-histological-images is known and can be provided during in the training phase, to the system (100; 200; 300) that is used for training a machine learning algorithm within the system (100; 200; 300).

The ground-truth associated with each of the source-histological-images is entirely at the discretion of the user and is not limited by the present invention.

However, for example, in the context of a training phase involving source-histopathological-images derived form a pathological subject, then the ground-truth may be optionally selected from one or more of:

(a) the presence or absence of the pathological condition in the subjects;
(b) the type, grade and/or stage of pathological condition in the subject (e.g. distinguishing between different stages and/or grades of cancer);
(c) the progression (or lack thereof) of the pathological condition in the subjects over a period of time following a defined event;
(d) the period of survival of the subjects following a defined event (typically excluding any deaths not related to the specified pathological condition); and/or
(e) the recurrence (or absence of recurrence) of the pathological condition of the subject following any earlier treatment (e.g. a surgical or non-surgical treatment) for that pathological condition;
wherein the "defined event" may, for example, be the time of taking the biological material from the subjects from which the source-histological image(s) were created, or the time of some previous treatment (e.g. a surgical or non-surgical treatment, such as a treatment as discussed above in section 2.3.2 of this application) for the pathological condition.

Optionally, the pathological condition may be a condition as described above in section 2.3 of this application, for example in a tissue, organ or other body part as described in section 2.2 of this application. In an embodiment of particular interest, the pathological condition may be a cancer, such as a cancer as described above in section 2.3.1 of this application, for example a solid cancer (e.g. carcinoma), of which a representative example is CRC as shown in the examples. Optionally, when the pathological condition is a cancer, then the "defined event" may be the time of some a previous treatment for the cancer, such as a treatment as defined in section 2.3.2 of this application, for example, surgery (such as a surgical resection of a tumour).

The period of time following a defined event can be any period of time of interest. In one embodiment, it may be between 0 to 24 hours, such as about 1, 2, 3, 4, 5, 6, 7, 8, 9, 10, 11, 12, 13, 14, 15, 16, 17, 18, 19, 20, 21, 22, 23 or 24 hours. In another embodiment, it may be between 0 to 28 days, such as about 1, 2, 3, 4, 5, 6, 7, 8, 9, 10, 11, 12, 13, 14, 15, 16, 17, 18, 19, 20, 21, 22, 23, 24, 25, 26, 27 or 28 days. In another embodiment, it may be between 0 to 12 months, such as about 1, 2, 3, 4, 5, 6, 7, 8, 9, 10, 11 or 12 months. In another embodiment it may be 1 or more years, and/or between 0 to 20 years, such as between 0 to 10 years, 0 to 9 years, 0 to 8 years, 0 to 7 years, 0 to 6 years, 0 to 5 years, 0 to 4 years, 0 to 3 years or 0 to 2 years, for example about 1, 2, 3, 4, 5, 6, 7, 8, 9, 10, 11, 12, 13, 14, 15, 16, 17, 18, 19 or 20 years.

Accordingly, in one embodiment, in the context of a training phase involving source-histopathological-images derived from pathological subjects, then the ground-truth is the progression (or lack thereof) of the pathological condition (such as cancer) in the subjects over a period of time following a defined event selected from the time of taking the biological material from the subjects from which the source-histological image(s) were created, or the time of some previous treatment for the pathological condition, and wherein the period of time is a period of time as indicated above.

In another embodiment, in the context of a training phase involving source-histopathological-images derived from pathological subjects (such as subjects with cancer), then the ground-truth is the period of survival of the subjects following a defined event, wherein the defined event is selected the time of taking the biological material from the subjects from which the source-histological image(s) were created, or the time of some previous treatment for the pathological condition (such as cancer), and wherein the period of time is a period of time as indicated above.

In the case that the algorithm is trained using source-histopathological-images of histopathological specimens for which the ground-truth associated with each image is a known prognosis for a particular pathological condition (such as cancer), then the ground-truth prognosis may take into account, for example:

(i) any pathological condition-specific (e.g. cancer-specific) death within the define period of time; and/or
(ii) the recurrence of the pathological condition (e.g. cancer) in the subject within the defined period of time.

The defined period of time for (i) and (ii) may be the same or may be different.

It may be suitable for the truth-data associated with the ground-truth to be representative of a 'category' of ground-truths. For example:

any ground-truth prognostic information which passes a first predefined threshold (e.g. pathological condition-specific survival for longer than a first predetermined period and/or non-recurrence of the pathological condition for a second predetermined period) may be considered to be associated with a "good prognosis" as the truth-data for that sample;

any ground-truth prognostic information which fails to pass a second predefined threshold (e.g. pathological condition-specific survival for less than a third predetermined period and/or recurrence of the pathological condition within a fourth predetermined period) may be considered to be associated with a "poor prognosis" as the truth-data for that sample;

and further the first and second predefined thresholds may be the same or different and, when they are different, then a third category of truth-data is possible, in which the ground-truth prognostic information passes the second predefined threshold but fails to pass the first predefined threshold, and this may be considered to be associated with a "non-distinct prognosis" as the truth-data for that sample.

In the training examples described herein, the histological specimens were obtained from cancer patients, and the ground-truth related to the categorisation of the known outcome for each patient into a prognostic group. Distinct prognostic group patients comprised patients with a good, poor, or indistinct prognosis. A patient was defined as having good prognosis if aged less than 85 years at surgery, had more than 6 years follow-up after surgery, and had no record of cancer-specific death and no record of recurrence during those 6 years. A patient was defined as having poor prognosis if aged less than 85 years at surgery and if they suffered cancer-specific death between 100 days (inclusive) and 2.5 years (exclusive) after surgery. Patients not satisfying either of these criteria were categorised as a non-distinct prognostic group.

4. Applications of the Systems of the Present Invention

As also discussed above, a computer implemented system of the present invention (100; 200; 300) can be used to process one or more source-histological-images (102; 202; 302), such one or more a source-histopathological-images, for which the outcome ("ground-truth") is not known.

In which case, the system can apply the machine learning algorithms that were configured using the training-histological-images (such as the training-histopathological-images), such that the output of the system is a classifier (118; 318), and/or an overall-classifier (232; 332), for the received source-histological-image 102.

It will be appreciated that the nature of the classifier and/or overall-classifier will be dependent on the nature of the ground-truth used during training, as discussed further in section 3 of this application.

For example, the classifier and/or overall classifier may give a diagnostic or prognostic determination for the subject from which the histological image(s) are obtained.

Accordingly, the present invention also provides a computer implemented method of processing one or more histological images by a method of the present invention as further described above, wherein the method is a method of producing a diagnostic and/or prognostic determination for a subject, wherein the method comprises receiving one or more source-histological-images (202; 302) obtained from one or more histological samples obtained from the subject, and wherein the method comprises:

determining a classifier (118; 318) for the one or more source-histological-images (102; 302) according to of the present invention as further described above; and/or determining the overall-classifier (232; 332) for the one or more source-histological-images (202; 302) according to of the present invention as further described above, and optionally, attributing a diagnostic and/or prognostic evaluation to the classifier and/or overall-classifier.

The subject may be any biological source, such as a biological source as described in section 2.1 of this application, and in one preferred embodiment is a human.

The one or more histological samples may be obtained from a subject that has, is suspected of having, is being treated for, has been treated for, and/or has previously had, a pathological condition, for example a pathological condition as described in section 2.3 of this application. In one embodiment of particular interest, the pathological condition is cancer, such as a cancer as further described in section 2.3.1 of this application.

The one or more histological samples may be obtained from any tissue type, organ or other structure of interest, for example, from any tissue type, organ or other structure of interest in the subject, as described in section 2.2 of this application.

Optionally, the or each histological sample obtained from the subject is, or are, obtained from the part of the subject's body that has, is suspected of having, is being treated for, has been treated for, and/or has previously had, a pathological condition, for example a pathological condition as described in section 2.3 of this application, and more particularly a cancer such as a cancer as further described in section 2.3.1 of this application.

In one preferred option, the method comprises assessing a plurality of source-histological-images (202; 302) obtained from a plurality of histological samples obtained from the subject. Optionally, the subject has, is suspected of having, is being treated for, has been treated for, and/or has previously had, a pathological condition, such as cancer, and further optionally the plurality of histological samples are samples that were obtained from to a plurality of locations within the body of the subject, which locations have, are suspected of having and/or have previously had, biological material including a pathological condition and/or are locations that are being treated for and/or or have been treated for the pathological condition, such as cancer, For example, wherein the pathological condition is cancer, the plurality of histological samples may comprise or consist of a plurality of samples taken from the same tumour in the subject, in which case the method can optionally permit an evaluation of tumour heterogeneity.

In one embodiment, the method comprises combining the determined classifier (118; 318) and/or overall-classifier (232; 332) with one or more further diagnostic and/or prognostic markers for a pathological condition of interest.

For example, the pathological condition may be a cancer, and the method may comprise combining the determined classifier (118; 318) and/or overall-classifier (232; 332) with one or more further diagnostic and/or prognostic markers for the cancer. For example, in the instance that the cancer is CRC, then one or more of the additional markers discussed in the examples of the present application may be used.

Where such one or more further diagnostic and/or prognostic markers are assessed, then the step of attributing a diagnostic and/or prognostic evaluation to the classifier (118; 318) and/or overall-classifier (232; 332) may include an assessment of the or each of the results of the assessment of the or each further diagnostic and/or prognostic markers.

These methods may be used, for example, to assist in making a diagnosis, in making a prognosis, in stratifying patient groups, in making a treatment decision for the subject on the basis of the diagnostic and/or prognostic evaluation of the stratified patient group, in a method of monitoring the progress or effect of an ongoing and/or previous treatment (such as a surgery and/or therapy), and/or in methods of treating subjects that have been assessed.

5. Methods of Treatment

The present invention further provides a method of treating a subject in need thereof, wherein a diagnostic and/or prognostic evaluation has been attributed to the subject by a method according to the present invention, the method comprising treating the subject by a method of surgery and/or therapy.

To put it another way, the present invention provides a surgical procedure, and/or a therapeutic treatment (such as a pharmaceutically-acceptable composition comprising one or more therapeutic agents), for use in a method of treatment of a subject in need thereof, wherein a diagnostic and/or prognostic evaluation has been attributed to the subject by a method according to the present invention.

Such methods of treatment can include, for example, therapeutic and/or prophylactic methods. Such types of treatment can include, for example, one or more forms of treatment as discussed above in section 2.3.2 of this application.

Preferably, the diagnostic and/or prognostic evaluation that has been attributed to the subject is in respect of a pathological condition, for example a pathological condition as described in section 2.3 of this application. In one embodiment of particular interest, the pathological condition is cancer, such as a cancer as further described in section 2.3.1 of this application.

The subject may be any organism, such as an organism as described in section 2.1 of this application, and in one preferred embodiment is a human.

The subject may be a subject that has, is suspected of having, is being treated for, has been treated for, and/or has previously had, a pathological condition, for example a pathological condition as described in section 2.3 of this application. In one embodiment of particular interest, the pathological condition is cancer, such as a cancer as further described in section 2.3.1 of this application.

Accordingly, the method of treatment may be a method of a treating a pathological condition as described in section 2.3 of this application. In one embodiment of particular interest, the pathological condition is cancer, such as a cancer as further described in section 2.3.1 of this application.

In an embodiment of particular interest, the pathological condition is cancer, and the subject that is to be treated is a subject that has previously been treated for the cancer (e.g. by surgery and/or a non-surgical therapy), prior to a diagnostic and/or prognostic evaluation being attributed to the subject by a method according to the present invention. In this way, for example, the subject can be stratified, and the likely benefit of further treatment (e.g. adjuvant treatment, and/or further surgical and/or non-surgical treatment) can be determined before a treatment modality is adopted for that subject.

The method of treatment can optionally comprise adapting one or more parameters of the surgery and/or non-surgical therapy in view of the diagnostic and/or prognostic evaluation has been attributed to the subject. Optionally, the one or more parameters of the surgery and/or non-surgical therapy are selected from the group consisting of the nature of the surgery and/or non-surgical therapy, the timing of the surgery and/or non-surgical therapy, period of the surgery and/or non-surgical therapy, the dosage of the non-surgical therapy, the route of administration of the non-surgical therapy, and the site(s) in the body that is targeted by the surgery and/or non-surgical therapy.

In one option, the diagnostic and/or prognostic evaluation of the subject includes the assessment of the effect on the subject of an earlier, or ongoing, treatment by therapy and/or surgery, for example, in order to monitor the progress and/or effect of such treatment, and further optionally wherein the method includes the step of making a further treatment decision, such as the cessation, continuation, repetition or modification an earlier, or ongoing, treatment and/or the implementation of a different treatment modality, and further optionally includes the step of implementing that treatment decision in respect of the patient.

The present invention is further described by the following examples that should not be construed as limiting the scope of the invention.

Example 1

Methods
Training and Tuning Cohorts

Four training cohorts were utilised in this study consisting of: (i) 160 stage I, II or III colon cancer patients treated between 1988 and 2000 at Akershus University Hospital, Norway as described in Bondi et al., *J Clin Pathol,* 2005; 58:509-14; (ii) 576 stage I, II or III CRC patients treated between 1993 and 2003 at Aker University Hospital, Norway as described in Danielsen et al., *Ann Oncol* 2018; 29:616-23; (iii) 970 stage I, II or III CRC patients treated between 1988 and 1996 in the Gloucester Colorectal Cancer Study, UK as described in Petersen et al., Gut, 2002; 51:65-9 & Mitchard et al., Histopathology, 2010; 57:671-9; and (iv) 767 stage II and III CRC patients treated between 2002 and 2004 in the VICTOR trial, UK as described in Kerr et al., *N Engl J Med,* 2007; 357:360-9 & Midgley et al., *J Clin Oncol,* 2010; 28:4575-80. These cohorts are further described sections 1 of the present application.

Patients were categorized into distinct or non-distinct prognostic groups depending on age at surgery and follow-up data. Distinct prognostic group patients comprised patients with good or poor prognosis. A patient was defined as having good prognosis if aged less than 85 years at surgery, had more than 6 years follow-up after surgery, had no record of cancer-specific death and no record of recurrence. A patient was defined as having poor prognosis if aged less than 85 years at surgery and suffered cancer-specific death between 100 days (inclusive) and 2.5 years (exclusive) after surgery. Patients not satisfying either of these criteria categorized as a non-distinct prognostic group.

The training cohort constituted of 1652 WSIs from the 828 patients with distinct prognosis in the four cohorts, while the tuning cohort constituted of 3280 WSIs from the 1645 patients with non-distinct prognosis. The WSIs were prepared by laboratory personnel at the Institute for Cancer Genetics and Informatics (ICGI), Norway. The demographics of training and tuning patients are summarized in Table 1, below.

Test Cohort

The test cohort consisted of 1824 WSIs prepared in Cheltenham, UK, from 920 patients in the Gloucester Colorectal Cancer Study. The WSIs were acquired from different formalin-fixed, paraffin-embedded (FFPE) tumor tissue blocks than those used in the training and tuning cohorts. The demographics of test patients are summarized in Table 1, below.

Validation Cohort

The validation cohort consisted of 2234 WSIs prepared at ICGI from 1,122 patients recruited to the QUASAR 2 trial (Kerr et al, *Lancet Oncol,* 2016; 17:1543-57).

The open-label, randomised, controlled QUASAR 2 trial (ISRCTN registry number ISRCTN45133151) enrolled 1952 patients with histologically proven stage III or high-risk stage II colorectal cancer between April 2005 and October 2010 from 170 hospitals in seven countries (Australia, Austria, Czech Republic, New Zealand, Serbia, Slovenia and the UK), of whom 1,941 had assessable data (Kerr et al, 2016, supra).

The trial was designed to investigate whether bevacizumab improved disease-free survival after potentially curative surgery of primary tumour. All patients received adjuvant chemotherapy in the form of capecitabine, but none received neoadjuvant treatment. No significant difference was observed between the treatment arms and the investigators concluded that the addition of bevacizumab to capecitabine should not be used in this adjuvant setting (Kerr et al, 2016, supra).

Through encouraging, but not requiring blood samples and tumour samples from primary resections, FFPE tissue blocks were collected from 1,251 of the QUASAR 2 trial patients with stage II or III colorectal cancer. These patients were representative for the whole trial population in terms of clinical and pathological characteristics (Kerr et al, 2016, supra). Pathologists at the participating hospitals in the trial performed the pathological evaluations. All patients provided written informed consent for treatment and the use of tissue samples. The West Midlands Research Ethics Committee (no. 04/MRE/11/18) and the Regional Committees for Medical and Health Research Ethics (REK) in Norway (no. 2015/1607) approved the study.

Figure 18:
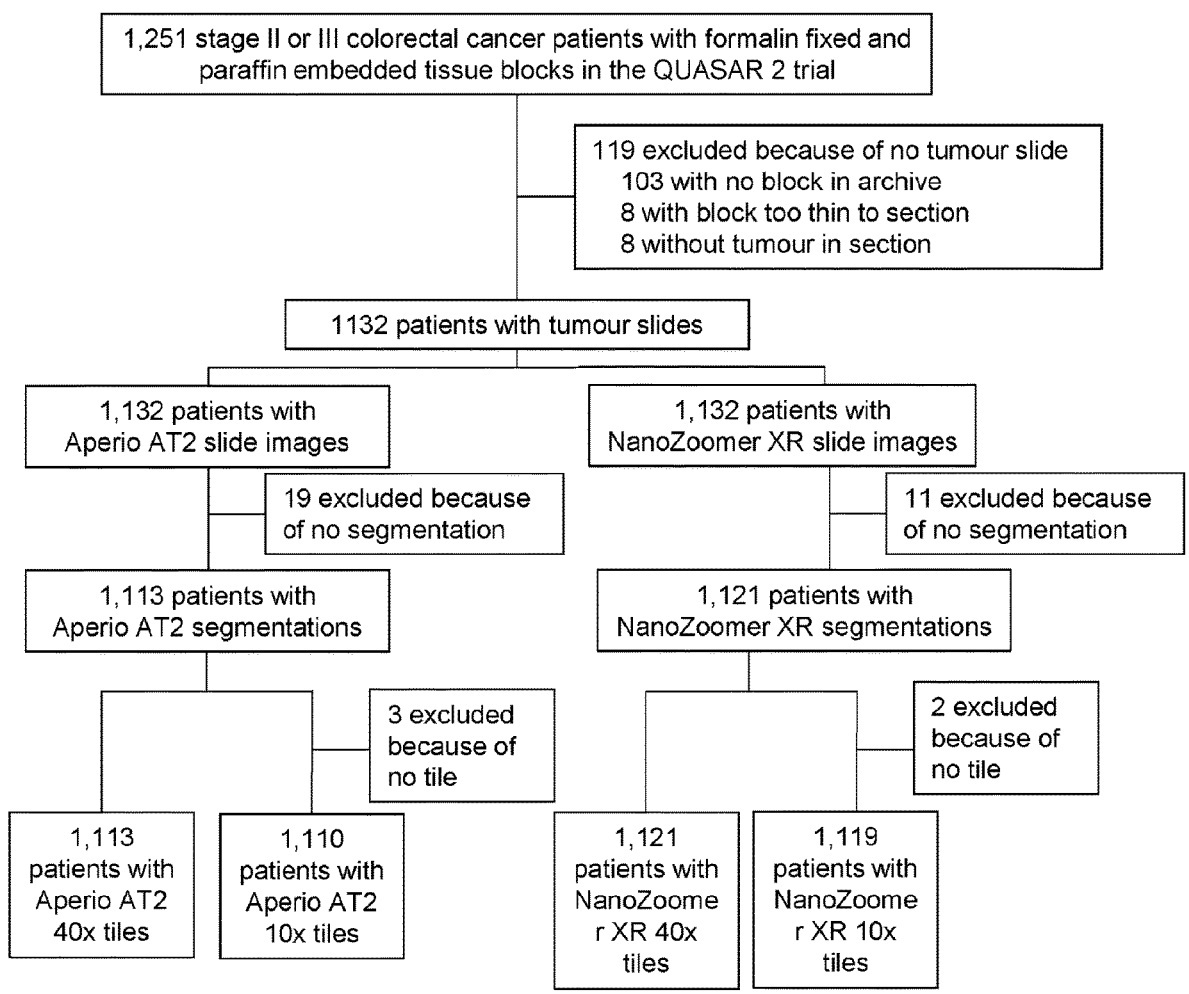
FIG. 18 shows a diagram specifying inclusions and exclusions of patients, slides and slide images from the QUASAR 2 cohort.

Tissue blocks from 1,140 patients were received, sectioned and prepared as 3 μm H&E-stained tissue slides by laboratory personnel at ICGI (FIG. 18). A local pathologist blinded to clinical outcome ascertained the presence of tumour in each tissue section. Digital images of the 1,132 sections with tumour were acquired using the same two scanners as in the training cohorts, i.e. an Aperio AT2 and a NanoZoomer XR. The previously developed segmentation model was blindly applied to automatically identify regions with tumour, giving 1,113 patients with Aperio AT2 segmentations and 1,121 patients with NanoZoomer XR segmentations (FIG. 18). The slide images where tiled as in the training cohorts, but no 10× tile could fit inside the automatic tumour segmentation for 3 Aperio AT2 segmentations and 2 NanoZoomer XR segmentations (FIG. 18). The QUASAR 2 cohort was defined as the 40× tiles from the Aperio AT2 slide images (available for 1,113 patients), the 10× from the Aperio AT2 slide images (available for 1,110 patients), the 40× tiles from the NanoZoomer XR slide images (available for 1,121 patients) and the 10× tiles form the NanoZoomer XR slide images (available for 1,119 patients).

The QUASAR 2 cohort is representative for patients eligible for the QUASAR 2 trial. An eligible patient had to satisfy all of the following inclusion criteria (originally described by Kerr et al, 2016, supra):

Aged 18 years or older.
Colorectal adenocarcinoma.
Histologically proven R0 M0 stage III or high-risk stage II colorectal cancer, where high-risk was defined as the presence of one or more of the following adverse prognostic features: stage T4, lymphatic invasion, vascular invasion, peritoneal involvement, poor differentiation and preoperative obstruction or perforation of the primary tumour Primary resection between 4 and 10 weeks prior to randomisation.

World Health Organisation (WHO) Performance Status 0 or 1.

Life expectancy of at least 5 years when taking into account comorbidities, but excluding cancer risk.

Additionally, an eligible patient could not satisfy any of the following exclusion criteria (originally described by Kerr et al, 2016, supra):

History of cancer other than treated in-situ carcinoma of the cervix, basal or squamous-cell carcinoma or if the disease-free interval after a previous cancer was greater than 10 years.

Inflammatory bowel disease and/or active peptic ulcer requiring treatment in the last 2 years.

Lack of physical integrity of the upper gastrointestinal tract, malabsorption syndrome or inability to take oral medication.

Moderate or severe renal impairment (creatinine clearance <30 mL/min).

Any of the following blood abnormalities:
  Absolute neutrophil count <$1.5 \times 10^9$/L.
  Platelet count <$100 \times 10^9$/L.
  Total bilirubin concentration >1.5 times the upper limit of normal (ULN).
  Alanine aminotransferase, aspartate aminotransferase or alkaline phosphatase concentration >2.5 times the upper limit of normal (ULN).

Proteinuria >500 mg per 24 hours.

Previous chemotherapy, immunotherapy or infra-diaphragmatic radiotherapy (including neoadjuvant therapy to the rectum) or patients who are expected to require radiotherapy to these sites within the next 12 months.

Use of any investigational drug or agent/procedure within 4 weeks of randomisation.

Chronic use of full-dose anticoagulants, high-dose aspirin (>325 mg/day), anti-platelet drugs or known bleeding diathesis (low-dose aspirin was allowed).

Concomitant treatment with sorivudine or its chemically related analogues.

History of uncontrolled seizures, central nervous system disorders or psychiatric precluding informed consent or interfering with compliance for oral drug intake.

Clinically significant cardiovascular disease, i.e. active or <12 months since e.g. cerebrovascular accident, myocardial infarction, unstable angina, New York Heart Association (NYHA) grade II or greater congestive heart failure, serious cardiac arrhythmia requiring medication or uncontrolled hypertension.

Known coagulopathy.

Known allergy to Chinese hamster ovary cell proteins or other recombinant human or humanised antibodies or to any excipients of bevacizumab formulation.

Women who were pregnant or lactating, or premenopausal women not using contraception.

The demographics of validation patients are summarized in Table 1, below.

TABLE 1

Patient characteristics in the training, tuning, test, and validation cohorts.

| Characteristic | Training cohort (N = 833) | Tuning cohort (N = 1652) | Test cohort (N = 925) | Validation set (N = 1132) |
|---|---|---|---|---|
| Median age (IQR)-yr | 69 (61-75) | 70 (61-77) | 71 (64-78) | 65 (59-71) |
| Sex-no. (%) | | | | |
| Female | 404 (48%) | 692 (42%) | 423 (46%) | 480 (42%) |
| Male | 429 (52%) | 960 (58%) | 502 (54%) | 652 (58%) |
| Stage-no. (%) | | | | |
| I | 101 (12%) | 103 (6%) | 71 (8%) | |
| II | 322 (39%) | 798 (48%) | 355 (38%) | 405 (36%) |
| III | 410 (49%) | 751 (45%) | 499 (54%) | 727 (64%) |
| Pathological N stage-no. (%) | | | | |
| N0 | 420 (50%) | 893 (54%) | 427 (46%) | 405 (36%) |
| N1 | 241 (29%) | 494 (30%) | 259 (28%) | 512 (45%) |
| N2 | 167 (20%) | 242 (15%) | 239 (26%) | 185 (16%) |
| Missing | 5 (1%) | 23 (1%) | 0 (0%) | 30 (3%) |
| Pathological T stage-no. (%) | | | | |
| T1 | 26 (3%) | 30 (2%) | 6 (1%) | 18 (2%) |
| T2 | 110 (13%) | 138 (8%) | 66 (7%) | 72 (6%) |
| T3 | 467 (56%) | 1037 (63%) | 413 (45%) | 585 (52%) |
| T4 | 224 (27%) | 426 (26%) | 439 (47%) | 408 (36%) |
| Missing | 6 (1%) | 21 (1%) | 1 (0%) | 49 (4%) |
| Histological grade-no. (%) | | | | |
| 1 | 77 (9%) | 196 (12%) | 134 (14%) | 46 (4%) |
| 2 | 572 (69%) | 1155 (70%) | 493 (53%) | 852 (75%) |
| 3 | 178 (21%) | 283 (17%) | 298 (32%) | 170 (15%) |
| Missing | 6 (1%) | 18 (1%) | 0 (0%) | 64 (6%) |

TABLE 1-continued

Patient characteristics in the training, tuning, test, and validation cohorts.

| Characteristic | Training cohort (N = 833) | Tuning cohort (N = 1652) | Test cohort (N = 925) | Validation set (N = 1132) |
|---|---|---|---|---|
| Location-no. (%) | | | | |
| Rectum | 226 (27%) | 507 (31%) | 314 (34%) | 166 (15%) |
| Distal colon | 262 (31%) | 536 (32%) | 281 (30%) | 454 (40%) |
| Proximal colon | 308 (37%) | 459 (28%) | 330 (36%) | 458 (40%) |
| Missing | 37 (4%) | 150 (9%) | 0 (0%) | 54 (5%) |
| Median follow-up time (IQR)-yr | 6.4 (1.7-8.2) | 4.0 (2.2-5.2) | 2.4 (1.0-4.6) | 4.6 (3.3-5.1) |

*Percentages may not total 100 because of rounding.
IQR denotes interquartile range.

Sample Preparation

A 3 μm FFPE tissue block section was stained with hematoxylin and eosin (H&E) and a pathologist (M.P.) ascertained it contained tumor.

WSIs were acquired at the highest resolution available (referred to as 40×) on two scanners, an Aperio AT2 (Leica Biosystems, Germany) and a NanoZoomer XR (Hamamatsu Photonics, Japan).

Areas with high tumor content were identified by an automatic segmentation method (as described in section 1 of this application). A WSI on 40× resolution typically contains an order of 100,000×100,000 pixels, multiple orders of magnitude larger than images currently feasible for classification by deep learning methods. To preserve prognostic information contained at high-resolution, WSIs were partitioned into multiple non-overlapping image regions called tiles at 10× and 40× resolutions, where each pixel at 40× represents a physical size of approximately 0.24×0.24 μm².

Classification

Five convolutional neural networks were trained on the 634,564 10× tiles and five convolutional neural networks on the 11,591,555 40× tiles in the training cohort with the patients' distinct prognoses as ground-truth. All networks were DoMore v1 networks, a purpose-built network for classifying supersized heterogeneous images, comprised of a MobileNetV2 (Sandler et al, 2018, supra) representation network, a Noisy-AND pooling function (Krauss et al, 2016, supra), and a fully-connected classification network (FIG. 3).

Conventional classification networks are trained on images, where each image has an associated label. One approach is to let each tile inherit the label of its WSI, but due to spatial heterogeneity a tile does not necessarily contain prognostic information reflecting the WSI. Using ideas from multiple instance learning, we instead train on collections of tiles from a WSI, where each collection is labelled with the label of the WSI. Using a novel gradient approximation method, we are able to train the network end-to-end with an increased number of tiles representing each WSI during training.

The networks were trained beyond convergence and evaluated at 21 equidistant positions in the training progression, resulting in 21 models per training run. The performance of the models on the tuning cohort was used to select a single model from each training run, resulting in five models for each resolution.

To evaluate a WSI, each of the five selected models provides a prediction of the probability of poor prognosis, and the average predicted probability was defined as the predicted probability of the ensemble model. A suitable threshold for the predicted probability of each of the two ensemble models (one for 10× and one for 40×) was determined by evaluating the tuning cohort, resulting in two ensemble markers predicting either good or poor prognosis.

The performance of the two ensemble markers and some other candidate markers were evaluated on the test cohort, which led to the selection of the combination of the two ensemble markers for the primary analysis on the validation cohort. The combination, termed the DoMore-v1-CRC marker, predicted good prognosis if both ensemble markers predicted good prognosis, uncertain prognosis if the ensemble markers predicted differently, and poor prognosis if both ensemble markers predicted poor prognosis; the prediction was not defined if an ensemble marker could not be assayed because of no tiles.

Primary Analysis

We predefined a primary analysis of the DoMore-v1-CRC marker (which is embodied as the overall-classifier (232, 332) in FIGS. 2 and 3) for both scanners in the validation cohort. The selected metric for measuring model performance was the hazard ratio (HR) with 95% confidence interval (CI) of patients predicted as uncertain prognosis and patients predicted as poor prognosis relative to patients predicted as good prognosis, where the two HRs and their corresponding CIs were computed by analyzing a Cox proportional hazard model with the DoMore-v1-CRC marker as the only variable (the DoMore-v1-CRC marker was included as a categorical variable, i.e. the model consisted of the two indicator variables for uncertain prognosis and poor prognosis) and cancer-specific survival (CSS) as endpoint (Efron's method were used for tied events).

The selected test for assessing whether the DoMore-v1-CRC marker predicts CSS was the two-tailed Mantel-Cox logrank test using significance level 0.05. Time to CSS was calculated from date of randomization to date of cancer-specific death or loss to follow-up. The primary analysis is an unbiased evaluation of the DoMore-v1-CRC marker's ability to predict CSS in the target population of patients that received adjuvant chemotherapy (specifically capecitabine) and satisfied the eligibility criteria of the QUASAR 2 trial (as described above).

Statistical Analysis

Figure 16:
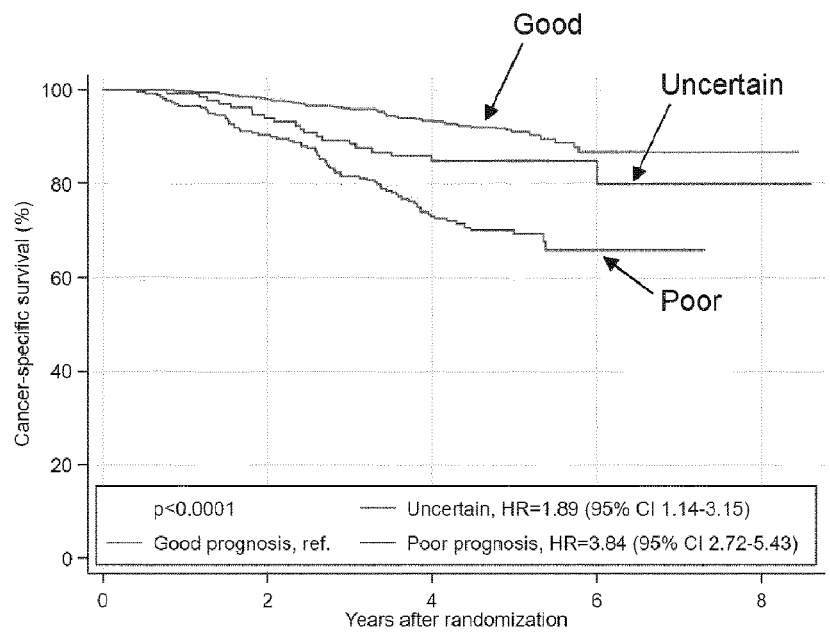
FIG. 16 shows the primary analysis and stage-specific analysis of the DoMore-v1-CRC marker in the validation cohort, wherein: (A) shows the results for all patients evaluated using Aperio AT2 images; (B) shows the results for all patients evaluated using NanoZoomer XR images; (C) shows the results for stage II evaluated using Aperio AT2 images; (D) shows the results for stage III evaluated using Aperio AT2 images; (E) shows the results for pN2 evaluated using Aperio AT2 images; and (F) shows the results for PT4 evaluated using Aperio AT2 images.
Figure 16:
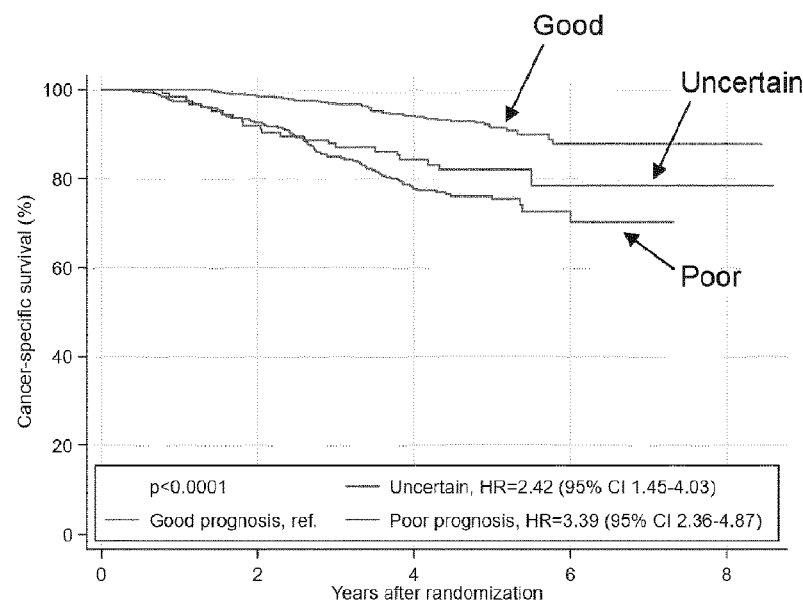
Figure 16:
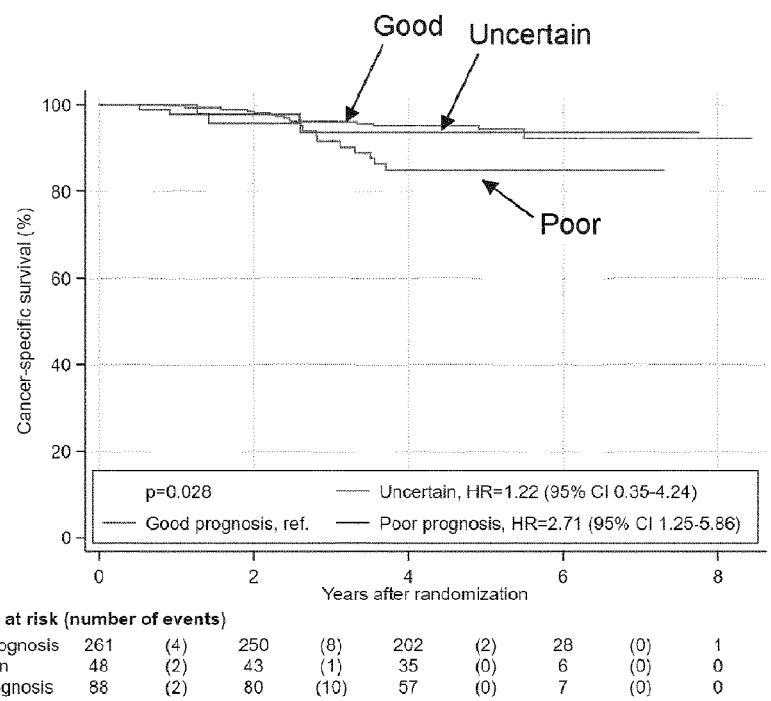
Figure 16:
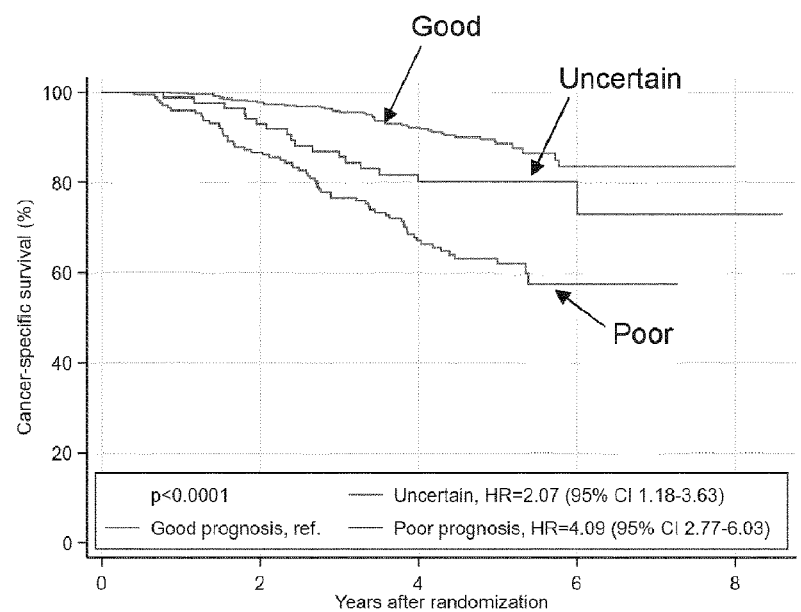
Figure 16:
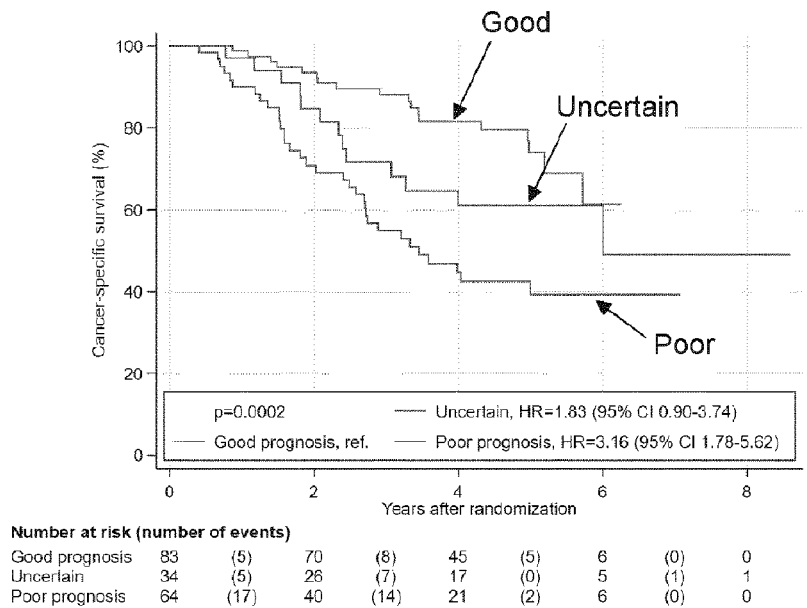
Figure 16:
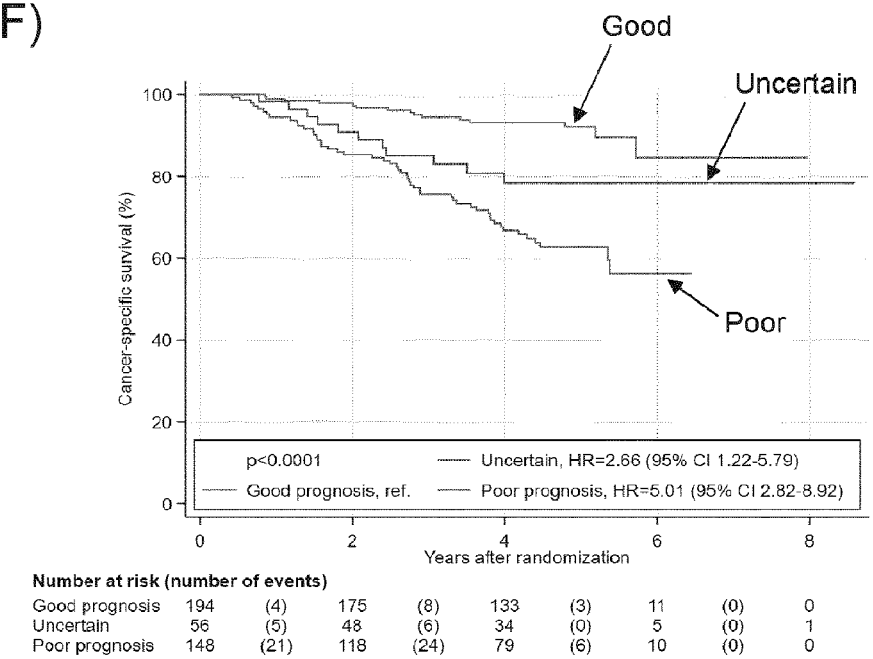

Primary and secondary analyses were planned in advance of evaluation on the validation cohort and described in the protocol. Markers were included in the multivariable model if available at the time of analysis and significant in univariable analysis of CSS. The confidence level of all reported CIs is 95%. Two-sided $p<0.05$ was considered statistical significant. Survival analyses were carried out in Stata/SE 15.1 (StataCorp, TX).
Results DoMore-v1-CRC was a statistically significant marker of CSS in the primary analysis of the validation cohort for both the Aperio AT2 scanner (HR for patients with uncertain prognosis prediction, 1.89; CI, 1.14-3.15; HR for patients with poor prognosis prediction, 3.84; CI, 2.72-5.43; p<0.0001; FIG. 16A) and the NanoZoomer XR scanner (HR for patients with uncertain prognosis prediction, 2.42; CI, 1.45-4.03; HR for patients with poor prognosis prediction, 3.39; CI, 2.36-4.87; p<0.0001; FIG. 16B). In the following, results from the Aperio AT2 scanner are presented. The corresponding analyses based on the NanoZoomer XR scanner as well as results based on 10×- and 40×-resolution levels for the two scanners were also significant (data not shown).

DoMore-v1-CRC significantly predicted CSS after adjusting for the covariates pN stage, pT stage, lymphatic invasion, and venous vascular invasion in multivariable analysis (HR for poor vs. good prognosis prediction, 3.04; CI, 2.07-4.47; Table 2). DoMore-v1-CRC was correlated with a number of established prognostic factors such as age, pN stage, pT stage, histological grade, location, sidedness, BRAF mutation, and microsatellite instability, but was not associated with sex, lymphatic invasion, venous vascular invasion or KRAS mutation (Table 3).

TABLE 2

Cancer-specific survival analyses in the validation cohort with the DoMore-v1-CRC marker evaluated on Aperio AT2 slide images.

| Variable | Group | Univariable analysis HR (95% CI) | p | Multivariable analysis HR (95% CI) | p |
|---|---|---|---|---|---|
| DoMore-v1-CRC | | | <0.0001 | | <0.0001 |
| | Good prognosis | ref. | | ref. | |
| | Uncertain | 1.89 (1.14-3.15) | | 1.56 (0.92-2.65) | |
| | Poor prognosis | 3.84 (2.72-5.43) | | 3.04 (2.07-4.47) | |
| pN stage | | | <0.0001 | | <0.0001 |
| | pN0 | ref. | | ref. | |
| | pN1 | 1.49 (0.95-2.32) | | 1.84 (1.13-2.98) | |
| | pN2 | 6.18 (4.00-9.54) | | 5.94 (3.71-9.52) | |
| pT stage | | | <0.0001 | | 0.0058 |
| | pT1 | n/a | | n/a | |
| | pT2 | 1.34 (0.66-2.71) | | 1.86 (0.90-3.86) | |
| | pT3 | ref. | | ref. | |
| | pT4 | 2.19 (1.56-3.07) | | 1.75 (1.22-2.51) | |
| Lymphatic invasion | Yes | 1.87 (1.22-2.89) | 0.0037 | 1.66 (1.07-2.56) | 0.023 |
| Venous vascular invasion | Yes | 1.48 (1.07-2.05) | 0.018 | 1.07 (0.76-1.51) | 0.71 |
| Age at randomization | 1-year increment | 1.01 (0.99-1.03) | 0.19 | | |
| Sex | Male | 1.12 (0.81-1.55) | 0.49 | | |
| Histological grade | | | 0.24 | | |
| | 1 | ref. | | | |
| | 2 | 1.23 (0.50-3.02) | | | |
| | 3 | 1.72 (0.66-4.45) | | | |
| Sidedness | Right | 1.24 (0.89-1.72) | 0.20 | | |
| KRAS | Mutated | 1.09 (0.77-1.54) | 0.64 | | |
| BRAF | Mutated | 1.54 (0.99-2.39) | 0.054 | | |
| Microsatellite instability | No | 1.53 (0.84-2.76) | 0.16 | | |

TABLE 3

Associations between the DoMore-v1-CRC marker evaluated on Aperio AT2 slide images and different patient characteristics in the validation cohort.*

| Characteristic | DoMore-v1-CRC good prognosis (N = 704) | DoMore-v1-CRC uncertain prognosis (N = 136) | DoMore-v1-CRC poor prognosis (N = 270) | Spearman's correlation p (95% CI) | p |
|---|---|---|---|---|---|
| Median age at randomization (IQR)-yr | 64 (58-71) | 65 (60-71) | 66 (60-72) | 0.07 (0.01 to 0.13) | 0.024 |
| Age at randomization-no. (%) | | | | 0.03 (−0.03 to 0.09) | 0.38 |
| ≤72 yr | 568 (81%) | 112 (82%) | 209 (82%) | | |
| >72 yr | 136 (19%) | 24 (18%) | 61 (18%) | | |
| Sex-no. (%) | | | | −0.02 (−0.08 to 0.04) | 0.59 |
| Female | 297 (42%) | 53 (39%) | 122 (39%) | | |
| Male | 407 (58%) | 83 (61%) | 148 (61%) | | |
| Stage-no. (%) | | | | 0.04 (−0.02 to 0.10) | 0.20 |
| II | 261 (37%) | 48 (35%) | 88 (35%) | | |
| III | 443 (63%) | 88 (65%) | 182 (65%) | | |

TABLE 3-continued

Associations between the DoMore-v1-CRC marker evaluated on Aperio
AT2 slide images and different patient characteristics in the validation cohort.*

| Characteristic | DoMore-v1-CRC good prognosis (N = 704) | DoMore-v1-CRC uncertain prognosis (N = 136) | DoMore-v1-CRC poor prognosis (N = 270) | Spearman's correlation ρ (95% CI) | p |
|---|---|---|---|---|---|
| Stage with substage-no. (%) | | | | 0.15 (0.09 to 0.21) | <0.0001 |
| IIA | 143 (21%) | 19 (14%) | 28 (14%) | | |
| IIB | 110 (16%) | 27 (20%) | 54 (20%) | | |
| IIIA | 67 (10%) | 2 (2%) | 6 (2%) | | |
| IIIB | 269 (40%) | 51 (38%) | 104 (38%) | | |
| IIIC | 83 (12%) | 34 (26%) | 64 (26%) | | |
| pN stage-no. (%) | | | | 0.10 (0.04 to 0.16) | 0.0008 |
| pN0 | 261 (38%) | 48 (36%) | 88 (36%) | | |
| PN1 | 339 (50%) | 53 (39%) | 111 (39%) | | |
| pN2 | 83 (12%) | 34 (25%) | 64 (25%) | | |
| pT stage-no. (%) | | | | 0.26 (0.21 to 0.32) | <0.0001 |
| pT1 | 15 (2%) | 0 (0%) | 2 (0%) | | |
| pT2 | 61 (9%) | 3 (2%) | 6 (2%) | | |
| pT3 | 402 (60%) | 75 (56%) | 100 (56%) | | |
| pT4 | 194 (29%) | 56 (42%) | 148 (42%) | | |
| Lymphatic invasion-no. (%) | | | | 0.04 (−0.02 to 0.10) | 0.20 |
| No | 599 (91%) | 122 (92%) | 220 (92%) | | |
| Yes | 62 (9%) | 10 (8%) | 33 (8%) | | |
| Venous vascular invasion-no. (%) | | | | 0.05 (−0.01 to 0.11) | 0.11 |
| No | 409 (61%) | 74 (56%) | 145 (56%) | | |
| Yes | 257 (39%) | 58 (44%) | 112 (44%) | | |
| Histological grade-no. (%) | | | | 0.14 (0.08 to 0.20) | <0.0001 |
| 1 | 27 (4%) | 7 (6%) | 8 (6%) | | |
| 2 | 565 (85%) | 88 (69%) | 186 (69%) | | |
| 3 | 76 (11%) | 32 (25%) | 59 (25%) | | |
| Location-no. (%) | | | | 0.15 (0.09 to 0.21) | <0.0001 |
| Rectum | 118 (18%) | 21 (16%) | 23 (16%) | | |
| Distal colon | 301 (45%) | 46 (35%) | 100 (35%) | | |
| Proximal colon | 246 (37%) | 64 (49%) | 138 (49%) | | |
| Sidedness-no. (%) | | | | 0.14 (0.08 to 0.20) | <0.0001 |
| Left | 419 (63%) | 67 (51%) | 123 (51%) | | |
| Right | 246 (37%) | 64 (49%) | 138 (49%) | | |
| KRAS-no. (%) | | | | −0.06 (−0.12 to 0.00) | 0.069 |
| Wild-type | 410 (65%) | 86 (73%) | 169 (73%) | | |
| Mutated | 224 (35%) | 32 (27%) | 73 (27%) | | |
| BRAF-no. (%) | | | | 0.22 (0.16 to 0.28) | <0.0001 |
| Wild-type | 588 (93%) | 89 (75%) | 190 (75%) | | |
| Mutated | 47 (7%) | 29 (25%) | 56 (25%) | | |
| Microsatellite instability-no. (%) | | | | −0.10 (−0.16 to −0.04) | 0.0018 |
| Yes | 66 (10%) | 26 (21%) | 40 (21%) | | |
| No | 595 (90%) | 99 (79%) | 213 (79%) | | |
| Median follow-up time (IQR)-yr | 4.8 (3.7-5.1) | 4.9 (3.1-5.1) | 4.1 (2.8-5.1) | −0.10 (−0.16 to −0.04) | 0.0006 |

*Percentages may not total 100 because of rounding.
IQR denotes interquartile range.

DoMore-v1-CRC was a significant predictor of CSS in stage II (HR for poor vs. good prognosis prediction, 2.71; CI, 1.25-5.86; FIG. 16C) and stage III (HR for poor vs. good prognosis prediction, 4.09; CI, 2.77-6.03; FIG. 16D).

It also significantly identified patients at increased risk of cancer-death in stage IIIA, IIIB, and IIIC (data not shown), and when stratified by pN stage (FIG. 16E and additional data not shown) or pT stage (pT1-3 vs. pT4; FIG. 16F and additional data not shown). A binary DoMore-v1-CRC marker provided close to the same HRs as poor vs. good prognosis prediction of the ordinary DoMore-v1-CRC marker (data not shown).

Inception v3, a state of the art convolutional neural network, was trained, tuned, and evaluated with the same study setup as DoMore-v1-CRC (see the discussion in section 1 of this application) and provided a statistically significant marker of CSS with only slightly worse performance than DoMore-v1-CRC (data not shown).

Figure 17:
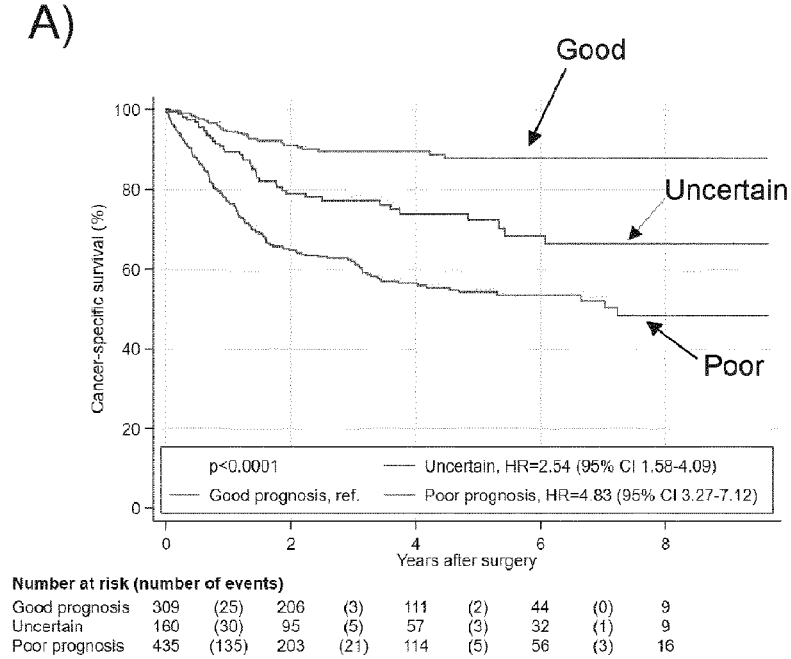
FIG. 17 shows the results for DoMore-v1-CRC markers evaluated on Aperio AT2 slide images in the test cohort. The ordinary DoMore-v1-CRC marker was evaluated in A, C, and D; wherein A) relates to all patients evaluated by DoMore-v1-CRC; C) relates to stage II evaluated by DoMore-v1-CRC, and D) relates to stage III evaluated by DoMore-v1-CRC. The binary DoMore-v1-CRC marker evaluated in B was made by averaging the predicted probability of the two ensemble models (one for 10× and one for 40×) of the DoMore v1 network, and thresholding the average at 0.58; the threshold was computed using the same method as applied to create the two ensemble markers from the two ensemble models (see the classification section of Example 1)
Figure 17:
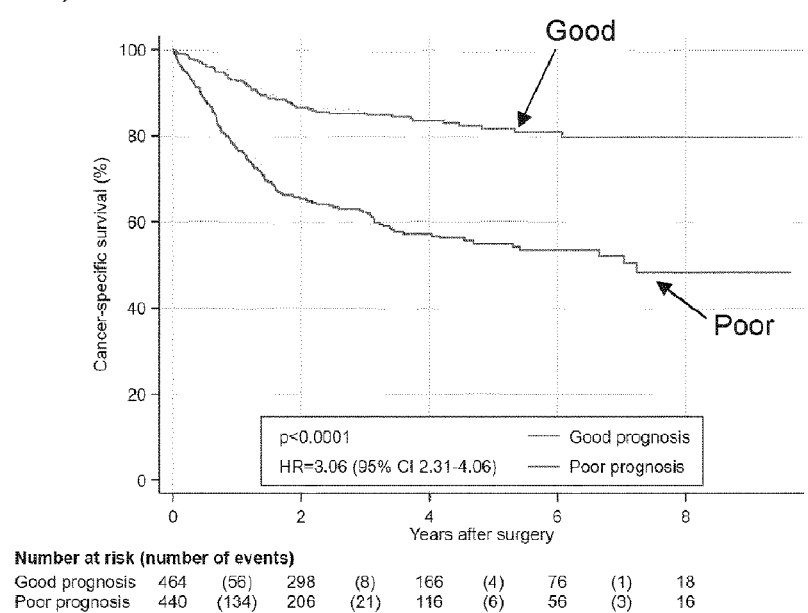
Figure 17:
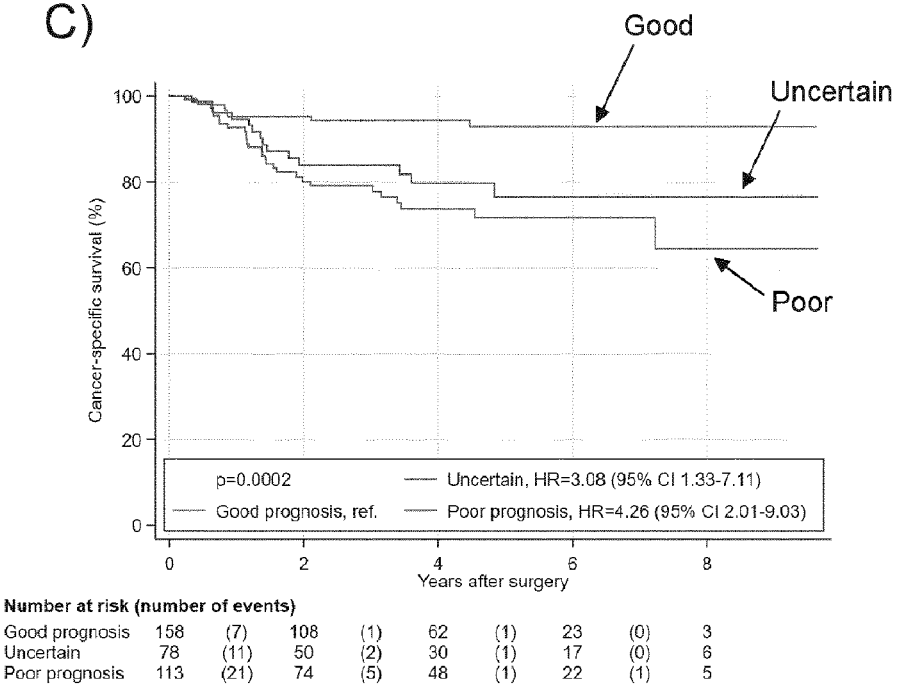
Figure 17:
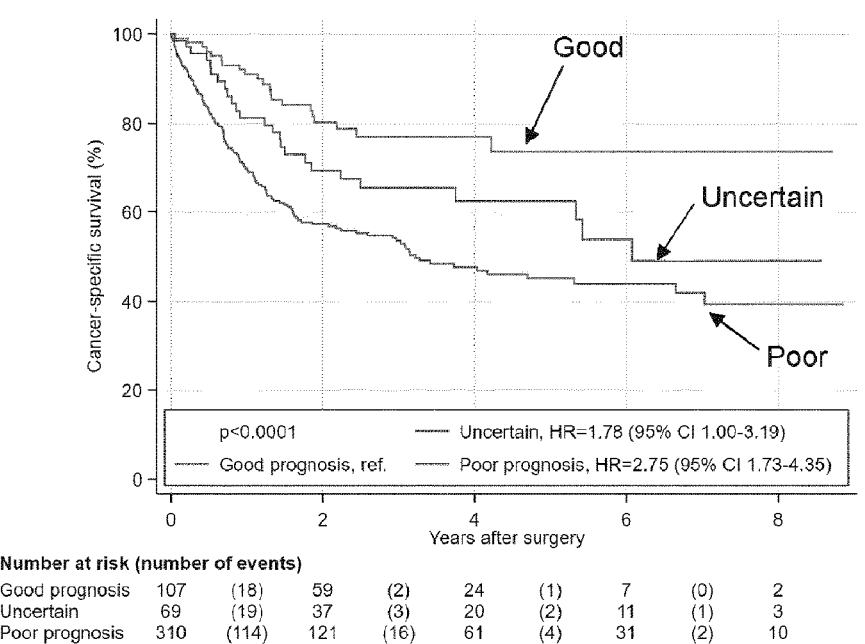

In the test cohort with sections from new tumor blocks prepared at a different hospital, DoMore-v1-CRC significantly identified patients at increased risk for cancer-death (HR for poor vs. good prognosis prediction, 4.83; CI, 3.27-7.12; FIG. 17A).

The robustness to laboratory preparation was evident also when analyzing DoMore-v1-CRC in stage II and III (FIGS.

17C-D). Dichotomizing DoMore-v1-CRC also provided a significant predictor of CSS (FIG. 17B).

It is important to remember that all patients in the QUASAR 2 validation cohort received adjuvant chemotherapy with capecitabine (the addition of bevacizumab did not affect disease-free or overall survival) which explains the observation that survival curves are generally better as only a minority of patients received chemotherapy in the test cohort.

Discussion

Building on recent developments in machine learning (LeCun et al., *Nature*, 2015; 521: 436-44), we have developed a fully-automated system for predicting the outcome of a patient, such as a cancer patient with CRC, using standard laboratory H&E stained histological sections. The method first outlines pathological (e.g. cancerous) tissue in the image and then stratifies the patients into prognostic categories; in the validation these differed 3-4 times in HR for disease-specific mortality.

Deep learning has already been shown to be suitable for detection and delineation of some tumor types (Ehteshami Bejnordi et al., *JAMA*, 2017; 318: 2199-210), and various cancer classifications have been reported (Coudray et al., *Nat Med*, 2018; 24: 1559-67). However, we have not yet seen validated systems for directly predicting the outcome of a patient based on histological images.

Automated prognostication procedures reduce human intervention, which could increase objectivity and reproducibility of the prognosis. Moreover, accompanied by increased robotization of wet-lab procedures, higher analytic throughput will allow decisions based on multiple samples from a tumor. This may reduce the challenge of tumor heterogeneity, which may be a key to improved accuracy of prognosis.

The majority of existing prognostic markers such as MMR status (Sinicrope, *Nat Rev Clin Oncol*, 2010; 7: 174-7; Mouradov et al., *Am J Gastroenterol*, 2013; 108: 1785-93), stroma estimation (Danielsen et al., *Ann Oncol*, 2018; 29: 616-23), lymphatic invasion (Akagi et al., *Anticancer Res*, 2013; 33: 2965-70), RNA profiles (Salazar et al., *J Clin Oncol*, 2011; 29: 17-24; Gray et al., *J Clin Oncol*, 2011; 29: 4611-9) and mutational burden (Mouradov et al., *Am J Gastroenterol*, 2013; 108: 1785-93) may be biologically plausible, but do not function as well as DoMore-v1-CRC, which outperforms these markers in terms of HRs and provides a more clinically useful stratification and distribution of patients among risk groups.

The DoMore-v1-CRC is technically simple to apply and can be delivered at standard pathology laboratories everywhere. Note that, whereas training the networks is resource demanding, the application of the DoMore-v1-CRC marker on slide images for new patients is a much smaller computational task and can be performed in a clinical setting in under ten minutes using consumer hardware. The clinical utility of the marker is that it can guide discussion with patients on the pros and cons of different treatment options (chemotherapy dose/schedules). Although the number of drugs used in the adjuvant setting is currently limited to fluoropyrimidines±oxaliplatin, there are recent data demonstrating that 3 months treatment achieves approximately the same survival outcomes as 6 months for the majority of stage III patients, while high risk patients (pT4 and pN2) might benefit from prolonged therapy (Grothey et al., *N Engl J Med*, 2018; 378: 1177-88; Iveson et al., *Lancet Oncol*, 2018; 19: 562-7).

The proportional reduction in the HRs for recurrence and death from CRC following adjuvant treatment is remarkably consistent at 20% across most well-designed clinical trials. However, this translates into quite different absolute survival improvements for low and high-risk subgroups. There are no prospective adjuvant trials for these risk stratified groups, but this should not prevent clinicians from interpreting existing trials data and applying these to individuals demonstrated to be at low or high risk of recurrence.

Taking FIG. 16C as example, one could interpret these data to suggest that those individuals with stage II disease in the poor prognostic group (approximately 20%) would benefit from single agent fluoropyrimidine e.g. capecitabine, whereas the better prognostic groups have a high likelihood of being cured by surgery alone. Stage III, pN2 and pT4 patients have more divergent survival curves (FIGS. 16D-F), and one could conclude that for patients who are not fit enough for combination chemotherapy in the good, and perhaps uncertain, survival groups have very reasonable survival with single agent capecitabine, whereas the poor prognostic groups are likely to benefit more from combination chemotherapy for 3 or 6 months (absolute survival benefits of around 8-10%). Clearly these survival curves are indicative and will be used by clinicians and patients to make joint and more informed decisions on adjuvant chemotherapy choices.

In summary, it has been possible to develop a clinically useful prognostic marker using a deep learning technique allied to digital scanning of conventional H&E stained, FFPE tumor tissue sections. The assay has been extensively evaluated in large, independent patient populations, correlates with and outperforms existing molecular and morphological prognostic markers, gives consistent results across tumor and nodal stage and can be used by clinicians to support decision making over adjuvant treatment choices.

We have also shown that a deep learning approach as described herein can be used to predict cancer-specific survival fully automatically and directly from scanned histopathology images (as exemplified using haematoxylin and eosin stained, formalin-fixed, paraffin-embedded tumour tissue sections). Independent validation of the classifier demonstrated that the exemplified system stratified stage II and III colorectal cancer patients into distinct prognostic groups, supplementing established prognostic markers, and outperforming most existing markers in terms of hazard ratios. The selection of adjuvant treatment after resection of cancerous tissue (e.g. colorectal cancer) could be improved by using the system to identifying patients at very low risk who may have been cured by surgery alone, as well as patients at high risk who are much more likely to benefit from more intensive regimes.

Accordingly, the present application describes an approach that is capable of delivering fully-automated deep learning systems for prediction of patient outcome from conventional histopathology images, stratifying those individuals, and enabling enhanced treatment decisions to be made.

Example 2

This example provides additional supporting data, showing preliminary results of the application of the method of the present invention to the assessment of lung cancer.

An experiment similar to the one described in section 1.3 and Example 1 was conducted using whole slide images of lung tissue from patients with lung cancer collected at Oslo University Hospital. As for the example from colorectal cancer, we used a single tissue block per patient, from which a single section was scanned on two scanners (Aperio AT2 and NanoZoomer XR) to produce two whole slide images per patient.

The method and experiment are exactly as described in section 1.3 and Example 1 with the following exceptions:
   All patients are from the same cohort
   The test cohort consist only of patients with either distinct good or distinct poor outcome
   Manual tumour segmentation used to define the area for tiling

TABLE 4

Number of patients used in the experiment

| Outcome | Training | Tuning | Test | Total |
|---|---|---|---|---|
| Distinct good | 146 | 0 | 58 | 204 |
| Distinct poor | 95 | 0 | 30 | 125 |
| Non-distinct | 0 | 451 | 0 | 451 |
| Total | 241 | 451 | 88 | 780 |

Figure 19:
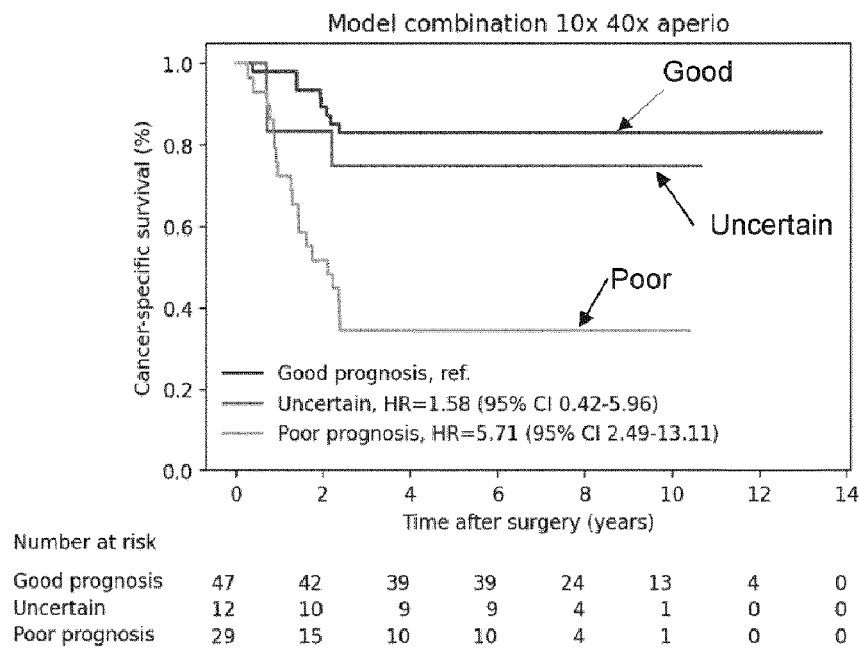
FIG. 19 shows Kaplan-Meier curves with Hazard ratio for patient groups predicted as Good prognosis, Uncertain prognosis, and Poor prognosis. A) results with scans from Aperio AT2; B) results with scans from NanoZoomer XR. Note: The cancer-specific survival is not in percent, despite the (%) in the label.
Figure 19:
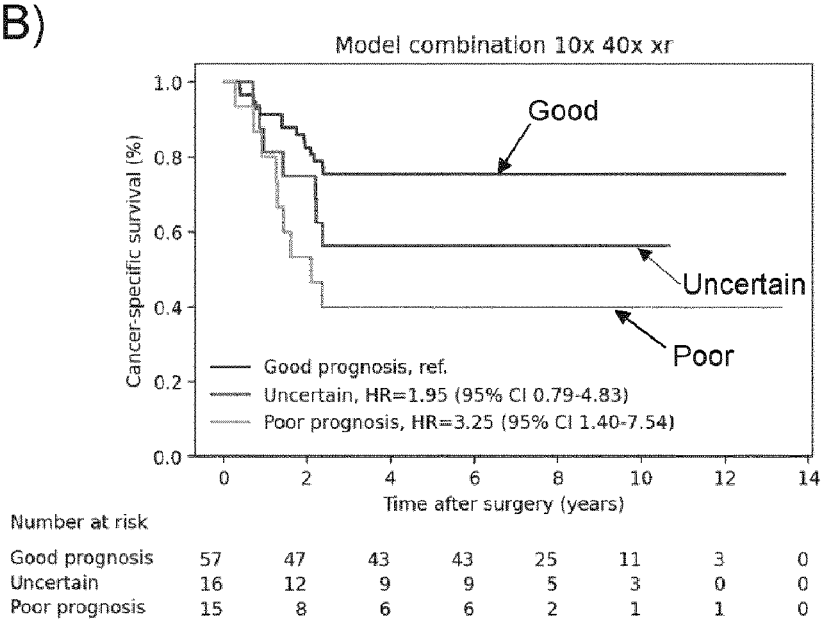

Survival analysis of the result on the test cohort is provided in FIG. 19, one Kaplan-Meier plot for each of the two scanners included in the experiment. This is the same format as the analysis presented in FIG. 16 for the colorectal cancer experiment. The plots illustrate cancer-specific survival, i.e. survival without lung cancer death for the three predicted outcome groups. The estimated survival probability can be read from the y-axis, whereas the x-axis represents time after surgery. As can be seen from the plots, the difference in cancer-specific survival is large when comparing the predicted Good prognosis group with the Poor prognosis group. The Uncertain group has a cancer specific survival in between the Good prognosis group and the Poor prognosis group.

It should be noted that the number of test patients is fewer than in the experiment from Example 1 (see Table 4). It is also noted that, unlike Example 1, the test patients are from the same cohort as the training patients, and so the weight that can be attributed to these result might be further confirmed in future assessments by selecting test patients and training patients from different cohorts. On the other hand, compared to Example 1, fewer patients were used in training, and all originated from the same cohort, whereas the use of a larger, and more diverse training cohort, could additionally improve the results.

As such, although it would be optimal to take further steps for validation on independent cohorts in order to critically assess the performance of this method on lung cancer samples, the preliminary results provided in this Example give a clear indication that the method can additionally be used to predict the outcome of patients with forms of cancer other than CRC, including lung cancer.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A computer implemented system for determining an overall-classifier of one or more source-histopathological-images, wherein each source-histopathological-image has been obtained from one or more histopathological samples obtained from one or more subjects, and wherein each subject has been diagnosed as having, is suspected of having, is being treated for, has previously been treated for, and/or has previously had, cancer, the system comprising:
   a first tile generator configured to generate a plurality of first-tiles from the one or more source-histopathological-images, wherein each of the plurality of first-tiles comprises a plurality of pixels that represents a region of the one or more source-histopathological-images having a first-area and a first-resolution;
   a second tile generator configured to generate a plurality of second-tiles from the one or more source-histopathological-images, wherein each of the plurality of second-tiles comprises a plurality of pixels that represents a region of the one or more source-histopathological-images having a second-area and a second-resolution, wherein:
      the first-area of the first-tiles is larger than the second-area of the second-tiles; and
      the second-resolution of the second-tiles is higher than the first-resolution of the first-tiles;
   a first machine-learning network configured to process the plurality of first-tiles in order to determine a first-classifier for the one or more source-histopathological-images, wherein the first machine-learning network (311) comprises:
      a first-neural-network configured to process the plurality of first-tiles in order to determine a tile-feature for each of the plurality of first-tiles;
      a pooling-function configured to combine subsets of the tile-features to generate a bag-feature for each of the subsets; and
      a second-neural-network configured to process the bag-features in order to determine a first-classifier for the one or more source-histopathological-images, wherein the second-neural-network is a classification network;
   a second machine-learning network configured to process the plurality of second-tiles in order to determine a second-classifier for the one or more source-histopathological-images, wherein the second machine-learning network comprises:
      a first neural-network configured to process the plurality of second-tiles in order to determine a tile-feature for each of the plurality of second-tiles;
      a pooling-function configured to combine subsets of the tile-features to generate a bag-feature for each of the subsets; and
      a second-neural-network configured to process the bag-features in order to determine a second-classifier for the one or more source-histopathological-images, wherein the second-neural-network is a classification network; and
   a classifier combiner configured to combine the first-classifier and the second-classifier to determine the overall-classifier for the one or more source-histopathological-images.

2. The system of claim 1, wherein the classifier combiner is configured to:
   apply a thresholding function to the first-classifier in order to determine a thresholded-first-classifier;
   apply a thresholding function to the second-classifier in order to determine a thresholded-second-classifier; and combine the thresholded-first-classifier and the thresholded-second-classifier to determine the overall-classifier.

3. The system of claim 1, wherein:
the first machine-learning network is configured to process the plurality of first-tiles in order to determine a plurality of first-classifiers for the one or more source-histopathological-images;
the second machine-learning network is configured to process the plurality of second-tiles in order to determine a plurality of second-classifiers for the one or more source-histopathological-images; and
the classifier combiner is configured to:
apply a statistical function to the plurality of first-classifiers in order to determine a combined-first-classifier;
apply a statistical function to the plurality of second-classifiers in order to determine a combined-second-classifier;
combine the combined-first-classifier and the combined-second-classifier to determine the overall-classifier.

4. The system of claim 1, wherein the classifier combiner is configured to perform a logical combination of the first-classifier and the second-classifier to determine the overall-classifier for the one or more source-histopathological-images.

5. The system of claim 1, wherein the first machine-learning network, the second machine-learning network, or both the first and second machine-learning networks-further comprise:
a loss-function configured to:
compare the classifier that is determined by the second-neural-network with a ground-truth that is represented by truth-data, and
set trainable parameters for the first-neural-network, the pooling-function, and the second-neural-network based on the result of the comparison.

6. The system of claim 1, further comprising:
a segmentation block that is configured to apply an image segmentation method to a whole-slide-image-histopathological image in order to provide a source-histopathological-image.

7. The system according to claim 1, wherein the first tile generator and the second tile generator are configured to generate their respective tiles independently of one another.

8. The system according to claim 1, wherein:
at least one of the first machine-learning networks and second machine-learning networks have been trained using training-histopathological-images and associated ground-truths, and
the one or more training-histopathological-images has been obtained from one or more histopathological samples obtained from one or more subjects, and wherein each subject has, has been diagnosed as having, is suspected of having, is being treated for, has previously been treated for, and/or has previously had, cancer.

9. The system of claim 1, wherein the cancer is selected from the group consisting of carcinoma, sarcoma, myeloma, leukemia, lymphoma and a mixed type of cancer.

10. The system of claim 9, wherein the cancer is a colorectal cancer, or lung cancer.

11. A computer implemented method of determining an overall-classifier for one or more source-histopathological-images, the method comprising:

generating a plurality of first-tiles from the one or more source-histopathological-images, wherein each of the plurality of first-tiles comprises a plurality of pixels that represents a region of the one or more source-histopathological-images having a first-area and a first-resolution;
generating a plurality of second-tiles from the one or more source-histopathological-images, wherein each of the plurality of second-tiles comprises a plurality of pixels that represents a region of the one or more source-histopathological-images having a second-area and a second-resolution, wherein:
the first-area of the first-tiles is larger than the second-area of the second-tiles; and
the second-resolution of the second-tiles is higher than the first-resolution of the first-tiles;
applying a first machine-learning network to the plurality of first-tiles in order to determine a first-classifier for the one or more source-histopathological-images, wherein applying the first machine-learning network comprises:
applying a first-neural-network to the plurality of first-tiles in order to determine a tile-feature for each of the plurality of first-tiles;
combining subsets of the tile-features to generate a bag-feature for each of the subsets; and
applying a second-neural-network to the bag-features in order to determine a first-classifier for the one or more source-histopathological-images, wherein the second-neural-network is a classification network;
applying a second machine-learning network to the plurality of second-tiles in order to determine a second-classifier for the one or more source-histopathological-images, wherein applying the second machine-learning network comprises:
applying a first-neural-network to the plurality of second-tiles in order to determine a tile-feature for each of the plurality of second-tiles;
combining subsets of the tile-features to generate a bag-feature for each of the subsets; and
applying a second-neural-network to the bag-features in order to determine a second-classifier for the one or more source-histopathological-images, wherein the second-neural-network is a classification network; and
combining the first-classifier and the second-classifier to determine the overall-classifier for the one or more source-histopathological-images.

12. The computer implemented method of processing one claim 11, and wherein the method further comprises:
attributing a diagnostic and/or prognostic evaluation to the classifier and/or overall-classifier.

13. The computer-implemented method of claim 12, wherein the subject is a human.

14. The computer-implemented method of claim 12, wherein the one or more histopathological samples obtained from the subject is, or are, obtained from the part of the subject's body that has, is suspected of having, is being treated for, has been treated for, and/or has previously had, cancer.

15. The computer-implemented method of claim 12, wherein the method comprises assessing a plurality of source-histopathological-images obtained from a plurality of histopathological samples obtained from the subject in order to determine a plurality of classifiers and/or overall-classifiers, and: optionally attributing the diagnostic and/or prognostic evaluation to the plurality of classifiers and/or overall-classifiers.

16. The computer-implemented method of claim 12, wherein the method comprises assessing one or more further diagnostic and/or prognostic markers for the cancer, and wherein the step of attributing a diagnostic and/or prognostic evaluation to the classifier and/or overall-classifier includes an assessment of the or each of the results of the assessment of the or each further diagnostic and/or prognostic markers.

17. The computer-implemented method of claim 12, wherein the method further comprises making a treatment decision for the subject on the basis of the diagnostic and/or prognostic evaluation, optionally wherein the treatment decision is in respect of a diagnosed or prognosed cancer condition, for example a cancer selected from the group consisting of carcinoma, sarcoma, myeloma, leukemia, lymphoma and a mixed type of cancer, and optionally wherein the cancer is a colorectal cancer or lung cancer.

18. The computer-implemented method of claim 17, wherein the diagnostic and/or prognostic evaluation of the subject includes the assessment of the effect on the subject of an earlier, or ongoing, treatment by surgery and/or non-surgical therapy, for example, in order to monitor the progress and/or effect of such treatment, and further optionally wherein the method includes the step of making a further treatment decision, such as the cessation, continuation, repetition or modification an earlier, or ongoing, treatment and/or the implementation of a different treatment modality, and optionally, implementing that further treatment decision in respect of the subject; wherein: the diagnostic and/or prognostic evaluation, the treatment and/or the treatment decision is in respect of a cancer condition, for example a cancer selected from the group consisting of carcinoma, sarcoma, myeloma, leukemia, lymphoma and a mixed type of cancer, and optionally wherein the cancer is a colorectal cancer.

19. The computer-implemented method of claim 12, the method comprising treating the subject by a method of surgery and/or non-surgical therapy; wherein the treatment for the diagnosed or prognosed pathological condition is for the treatment of cancer, for example a cancer selected from the group consisting of carcinoma, sarcoma, myeloma, leukemia, lymphoma and a mixed type of cancer, and optionally wherein the cancer is a colorectal cancer or lung cancer.

20. The computer-implemented method of claim 19, wherein the subject is a human.

21. The computer-implemented method of claim 19, wherein the subject: (a) has, has been diagnosed as having, is suspected of having, is being treated for, has previously been treated for, and/or has previously had, cancer; and/or (b) wherein a diagnostic and/or prognostic evaluation of a cancer condition has been attributed to the subject by a method according to any of claims 10 to 17.

22. The computer-implemented method of claim 21, wherein the pathological condition is a cancer selected from the group consisting of carcinoma, sarcoma, myeloma, leukemia, lymphoma and a mixed type of cancer, and optionally wherein the cancer is a colorectal cancer or lung cancer.

23. The computer-implemented method of claim 19, wherein the method comprises adapting one or more parameters of the surgery and/or non-surgical therapy in view of the diagnostic and/or prognostic evaluation that has been attributed to the subject by a method according to any of claims 10 to 17, and optionally wherein the one or more parameters of the surgery and/or non-surgical therapy are selected from the group consisting of the nature of the surgery and/or non-surgical therapy, the timing of the surgery and/or non-surgical therapy, period of the surgery and/or non-surgical therapy, the dosage of the therapy, the route of administration of the non-surgical therapy, and the site(s) in the body that is targeted by the surgery and/or non-surgical therapy.

\* \* \* \* \*